(12) United States Patent  
Feinberg et al.

(10) Patent No.: US 7,985,550 B2  
(45) Date of Patent: Jul. 26, 2011

(54) METHODS OF ISOLATING METHYLATED CPG ISLANDS

(75) Inventors: Andrew P. Feinberg, Cleveland, OH (US); Liora Strichman-Almashanu, Baltimore, MD (US); Shan Jiang, Trumbull, CT (US)

(73) Assignee: The Johns Hopkins University, Baltimore, MD (US)

( * ) Notice: Subject to any disclaimer, the term of this patent is extended or adjusted under 35 U.S.C. 154(b) by 183 days.

(21) Appl. No.: 12/350,159

(22) Filed: Jan. 7, 2009

(65) Prior Publication Data

US 2010/0273658 A1    Oct. 28, 2010

Related U.S. Application Data

(63) Continuation of application No. 11/084,085, filed on Mar. 17, 2005, now Pat. No. 7,488,815, which is a continuation of application No. 09/861,893, filed on May 22, 2001, now Pat. No. 6,960,434.

(60) Provisional application No. 60/206,161, filed on May 22, 2000, provisional application No. 60/206,158, filed on May 22, 2000.

(51) Int. Cl.  
*C12Q 1/68* (2006.01)

(52) U.S. Cl. .......................................................... 435/6

(58) Field of Classification Search .................. 435/6  
See application file for complete search history.

(56) References Cited

U.S. PATENT DOCUMENTS

| 6,251,594 B1 | 6/2001 | Gonzalgo et al. |
| 6,300,071 B1 * | 10/2001 | Vuylsteke et al. ................. 435/6 |
| 6,617,434 B1 * | 9/2003 | Duffy .......................... 530/387.9 |

FOREIGN PATENT DOCUMENTS

| WO | WO 00/04187 | 1/2000 |
| WO | WO 00/26401 | 5/2000 |

OTHER PUBLICATIONS

Arima et al., "A novel imprinted gene, HYMAI, is located within an imprinted domain on human chromosome 6 containing ZAC", *Genomics*, 67, 248-255 (Aug. 1, 2000).

Feinberg, "Methylation meets genomics", *Nature Genetics*, 27:9-10 (2001).

Gregorova et al., "PWD/Ph and PWK/Ph Inbred mouse strains of Mus m. musculus subspecies: A valuabl3e resource of phenotypic variations and genomic polymorphisms", *Folia Biologica*, 46(1):31-42 (2000) Abstract.

Hayward et al., "Bidirectional impriting of a single gene: GNAS1 encodes maternally, paternally, and biallellically derived proteins", *Proc. Natl. Acad. Sci.*, 95:15475-15480 (1998).

(Continued)

*Primary Examiner* — Kenneth R. Horlick  
(74) *Attorney, Agent, or Firm* — DLA Piper LLP (US)

(57) ABSTRACT

Provided is a method for isolating methylated CpG islands. The method includes identifying an imprinted gene adjacent to the methylated CpG island, and identifying a disease which is preferentially transmitted by one parent and which is genetically linked to region of genomic DNA which contains the imprinted gene, whereby the imprinted gene is thereby indicated as a candidate gene involved in transmitting the disease.

13 Claims, 41 Drawing Sheets

OTHER PUBLICATIONS

Labosky et al., "Mouse embryonic germ (EG) cell lines: transmission through the germline and differences in the methylation imprint of insulin-like growth factor 2 receptor (Igf2r) gene compared with embryonic stem (ES) cell lines", *Development*, 120:3197-3204 (1994).

Lee et al., "Isolation and Genetic Transformation of Primordial Germ Cell (PGC)—Derived Cells from Cattle, Goates, Rabbits and Rats", *Asian-Australasian Journal of Animal Sciences*, 13(5):587-594 (2000).

Matsui et al., "Derivation of Pluripotential Embryonic Stem Cells from Murine Primordial Germ Cells in Culture", *Cell*, 70:841-847 (1992).

Mitsuya et al., "Epigenetic reprogramming of the human H19 gene in mouse embryonic cells does not erase the primary parental imprint", *Genes to Cells*, 3:245-255 (1998).

Ogawa et al., "Relaxation of insulin-like growth factor II gene imprinting implicated in Wilms' tumour", *Nature*, 362:749-751 (1993).

Overall et al., "Genomic Imprinting in the Rat: Linage of Igf2 and H19 Genes and Opposite Parental Allele-Specific Expression During Embryogenesis", *Genomics*, 45:416-420 (1997).

Sutcliffe et al., "Deletions of a differentially methylated CpG island at the SNRPN gene define a putative imprinting control region", *Nature Genetics*, 8:52-58 (1994).

Uejima et al., "Hot-stop PCR: a simple and general assay for linear quantitation of allele ratios", *Nature Genetics*, 25:375-376 (2000).

Labosky et al., "Mouse embryonic germ (EG) cell lines: transmission through the germline and differences in the methylation imprint of insulin-like growth factor 2 receptor (Igf2r) gene compared with embryonic stem (ES) cell lines", *Development*, 120(11):3197-204 (1994).

Matsui et al, "Derivation of pluripotential embryonic stem cells from murine primordial germ cells in culture", *Cell*, 70(5):841-847 (1992).

Szabó & Mann, "Biallelic expression of imprinted genes in the mouse germ line: implications for erasure, establishment, and mechanisms of genomic imprinting", *Genes Dev.*, 9(15):1857-1868 (1995).

Toyota & Issa, "CpG island methylator phenotypes in aging and cancer", *Semin. Cancer Biol.*, 9(5):349-57 (1999).

Xin et al., "The developmental fate of green fluorescent mouse embryonic germ cells in chimeric embryos", *Cell Res.*, 9(3):201-208 (1999).

\* cited by examiner

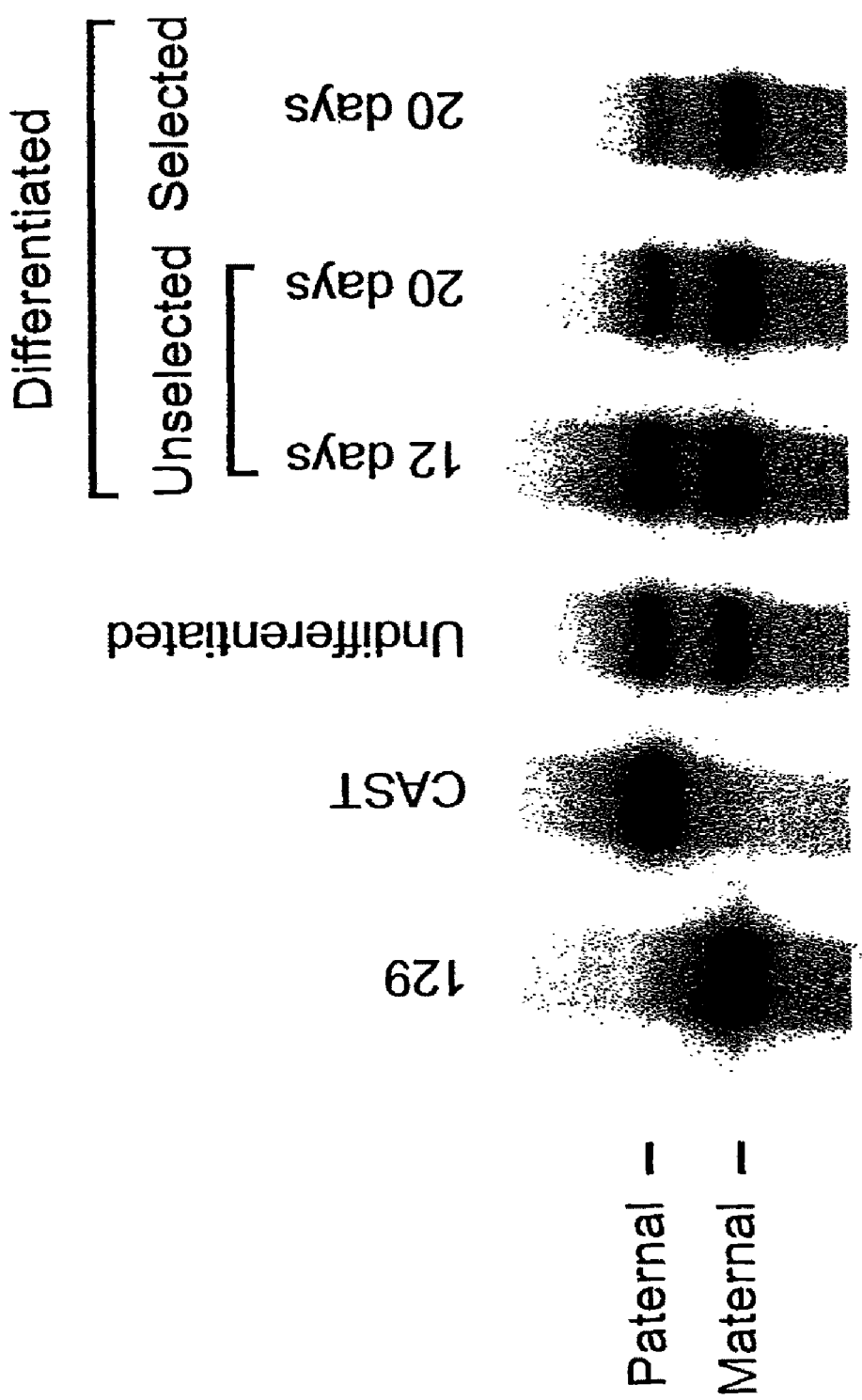

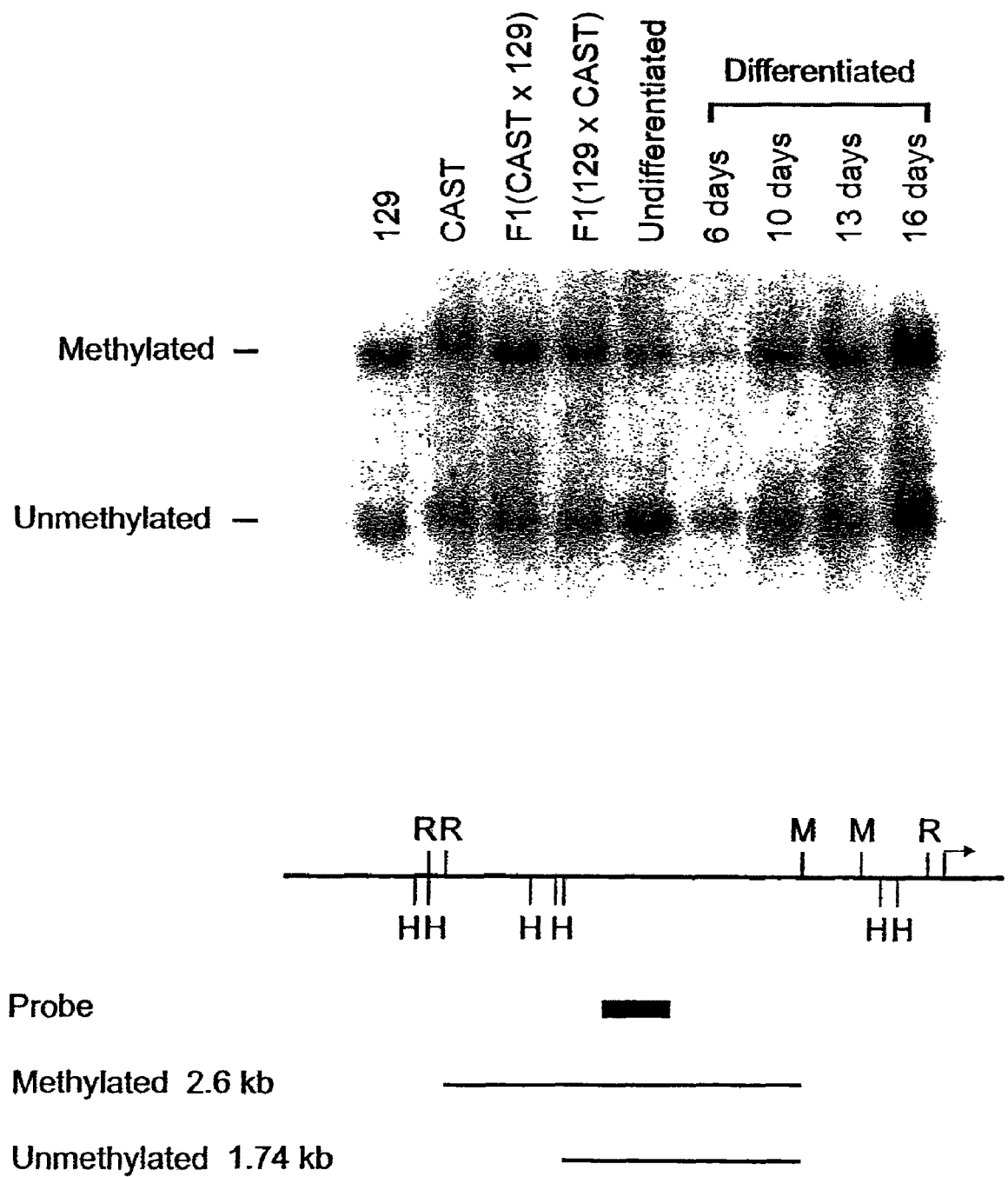

FIG. 14-1
Sequences not available in public databases

*1-5*

CGGGCTCGGGGTCAGGGTGGGCAGTGGACACTCACGCAACATGGAGGACC

TACAGCCGCGGGCTCGGGGTCAGGGCAGGCAGTGGACGCTCACACACAGA

GGACCTACAGCCGCGGGCTCAGGGTCAGGGCGGACAGTGGATGCCCACAC

AACACAGAGGACCTACGGCCACAGGCTCGGGGTCAGGGCGGGCAGTGGAT

GCCCACACAACACGGAGGACCTGCGGCCG

*1-12*

CGGCCGTGTGGGCATCCGTGTCAGAGTGCTGTGTGCCGGGCGACGCTCAG

GGCGGCTGTGCGGGCATCTGTGTCAGAGTGCTGTGTGCCGGGCGACGCTC

AGGGCGGCCG

*1-13*

CGGCCGTGGCTTCTACCGTGCTGCGGGGCTGCGGGTCCCGGGTGGGCCCA

TTGCCCGGTCACACTCGGATCTTGGAATAAAATGTGGGCGTCCATGTGAG

GCCGAAGCAGTGGCTGTGACGCCCACGCGGGGTGCGATCTCTGCGGGAG

CCGGCCG

*1-20*

CGGCCGCAGCCACGCGCAGGGAGGAGCCCGGGGCACCATAGCACAGCGCC

GGCCTCACACACACCCTCGAGGCCCCTCTCGAGCCCCGCGGAGCCCTCC

GCGGCCG

*1-22*

CGGCCGTGGGAAGTACGCGAGGCAGGGGGTGGCCGTGGGAGGGACGCGA

GGCAGGGGGCGGCTGTGGGAGGGACTTGAGGCAGGGAGGTGGCCCTGGGA

GGGACTTGAGGCAGGGGGTCGGCCG

CGGCCGGGCCCACGCCCGACAGTTGCAGCAGTTGCGGCGATTGCAGCGCG

CCGGCGCACAGGATCACCTCGCGGCGGGCGCGCAGGGTGCGCACCTGGCC

GTCCTGGCGATAGCGCACGCCGCAGGCGCGGCTGCCCTCGAACAGGATCG

CCATGGCGTGCGCGCCGGTCTCCACCCGCAGGTTGGCGCGGCCG

*2-6*

TGTTCCTTGCTGTAGCCGAAACCCTGGAGGGTGCTGTGCGGCCTGGCCTG

GGAGCCCATGCCTGCAGAGGGTCCTCCGTTAGCAGCAAGCCGGCCCCAC

CCTCGGCCCTGCCCACGGATGGCACAGACACCCAGGACACTCAAGGAGGC

AGAAACCAGGTGCCAGAGCTGGACACGGTCCCCTCAGTCACCTACCTGTG

GCAGGCGGGGTCCCCAGAGGCTGGGAGGGAGCCAGCGGCAACACGGTGTC

CGAGAACAGGGTGCTCCCCAAGTCCTACAGGGGGAGGCGAAGGCCCTCAG

TGTCCTCACACCAGGGCCTGCTGTACTCACCCTGCCACCCATATCAGCTC

CGTTCTGTCCCCGGACACTTCTCCTGAGCCACTCAGCTGGACACAGGCT

CTGTGTCCACCAGCAAGGAGCAGAGGCAGGGTCCCGGATGGGAGAACTG

CAAACCCCCAGCTGACATCCTGGCCCCAATCCCACCCCTCTACAGGAGG

AGGGGCACCCCGCAGAGCGACACTGCTCCTGGGCTCACCTGCGCGGCCG

*2-22*

CGGCCGCCGGTTCTGGTCAGGGACCCCTGCCCGGCAATGAAGGCCGAGCC

TCAGAGGGCCCTGGGCTGCCGGGAGGGTGTTCGAGGACCCTGCCCAGGGC

AAGGCTTGAGGTCCTCCTCGCTGAGGCCTTGCATCCTCGATGGCCATCCT

GTCTCCTGCTCCCACGTTTCCTGAGGACGTGGCCCAGTGGCGCCTTCTA

CCACAGCAGGGCTGGCCCTGAGGGGCAGGTTTGGTCTGGCAGAGGCGCT

GGTGCGTGACTCCCGCACAACACAGGTGTGGGTTTTGTGGGCGTCTGCTG

FIG. 14-3

CCTGCCCCGGCCCCAAGCCTGTGGCTGCAGGTCCTCTGAGTATGGGCGTC

TGCTGCCCGCTCTGACCCCGAGCCCGCGGCCG

*2-42*

CGGCCGGGGGGCCCCTGGGGAGCTAGGCCGGGCTCGGGCACAGGCACCGG

CACGGGCACTGGCACCGGCACCGGCACGGGCAAGGGCACCGACCCGACGG

CGGTGGGCGCGGGCCGGGAGCCGCTGCCGCTCTCGGTCAGCACCGTCCGC

TTGAGCGGCCCAGGCGCCTCGAGGCGCAGTGGCCCGGCGGCGGGCGGGCG

GTCCCCGGGGGCTTGCGCGCGGTGCGAGGGCCGGCGGCGCAGCTCGG

ACGTGAGCTCGTGCTTGAGGAAGCGGAACACCTCCTTGGCTGGGCCGCGG

CGCTCGGGCTCCAGGGCCAGTAAGCGCTGGAACATGCGCAGCGCGGGCTC

GGTGAAGCGGCGCCACTGCGAAGGCAGCCCCGGCAGGCGGCCCCGCTGCC

AGCGCACGAACTCCTCGAAGAAGGCGTCGGCGCCCGACGCCGCCTCCCAC

GGAAGTTGCCGGTGAGCACGCAGAAGATGAGCACGCCGAAGGCCCACACG

TCCACGCCCGTGTCCACCGCCAGCCCGTCGGCGCGGCCCGCCTGGCACAC

CTCAGGCGCCGTGTAAGGGATGGTGCCGCTCACGCGCTTGACGCGGCAGC

CCACGCGGCGCGTCATGCCGAAGTCGGCCAGCTTTACGCGGCGGCACTCG

CGGTCGAACAGCAGCACGTTCTCGGGCTTGATGTCGCGGTGCACCAGCTG

CCGCCCGTGCATGAAGTCCAGCGCCAGGCCCAGCTGCTGCACACAGCGCT

TCACCGTGTCCTCAGGGAGCCCCACCTGCGGGCGGCCG

*2-48 (BpH)*

TAAACCAATTTCACAGGCAAGTTTCCCTTGAAAAACAACTCCTTGCCATA

ATCATCACATTCATTGAGTGACCATCTACCAAATGCTTTACTCCCATGAT

TTCATGTAATATTGACATTCACCCTACAAAGTAGATGGTATTACAGTGTC

TGTTTTACAAGTGAGAAATCCGAGGAACAGGAAGTCAATTTGCCAAGTGT

FIG. 14-4

```
TGCACAGCTAAATCGAGATTCCAGAGAATGTCACCTCAAAGCTTCTAGTG
GGGCTGTCATGTAGGTTGTGGTCGCTTTGGATAACAGGAGACGCTAAGGA
AAATCAGTACTGGTTACTGAGGATGGAAGAGGCGCARATATTTCACCACA
GGCGACGAAAACCCCACTTTTAGGCTGGCCACACAGGAGCCCCGAGGAAA
CTATGCGTCCCCTTCCTCCCCGCCCCACACTGCCCTGGCCTGGCGGAGC
AGCGGCCGCAAGTGTAACTGYTGTTGCCCAGATCGAACCAAGCCCGGTCC
CAGTGACGAGCAGCGGCCTGCGGGGCCAGAGCGTCTGGGAGCCTTTCATG
ACCCCAAAGCCCAGGGAGGTCCCCGCACCATCGGGCCCCGCGCCCTAGCT
CGGTCCGCCGTCGAGGGTGCCTGAAGTCCCTGCGGGCGCCGGGGAGAAA
GCCCGGGGCTTAGCCTCCTCCATCCCCAGCCATCTGTCACCGCCTCCTAG
GCCCCGGCTGGAGCCCCATGGGCGCCTCCCGCGCCTACCAAGGAGCCAGG
GAGACAAGGATCCCGGAGACCTCTGGGGCGCCCTCCAGCTGAGGATTCCG
CCGCGGCTCCCGCAGCCGCTTCTCCCCATTCGGTGCAGCCCACCTGGCCC
AGCTCTCGGCCGGTCTCCCTCGGAGGTCCGAAAAGGGAGAGGGCGGGCCA
GGGCTCCCCGCTGGCCGGAGCCGCAGCCCCTTTCCCCCTCCCCACCCAG
GGACCCTTCCCGGACCCTCCTGGGCGCAGCCCTCACCTGCTGCCCGCACC
GCCTCCGAGGAAGGCCCTCGGGCTCCACCTGGCCTCATCACCGCTTCCCT
TATCCGGGAGGAGGAGGAAACTCAACCCTCTAGGCCAGGCCCTGTGCTCA
CTTTAGATACTTTATTTCGTTTAATTCTTAGGGTTTTAACCCCTGAGTTT
AAGGCGAAGGATCCGAGGTTCCGAAAAGCCATGCAGWGCAGGGAGGATTC
AAACAGCCAAACCTGCTGGTCTCCGTGCTCTTGGKAGCGGNAAAGAGATT
TWGRKGGAGWAAGTCGTTTTWTAGYTATACTCYCTCTGTGWAAACATAAT
WAAAASTGSMCCACCMCCTTSTGGAAAGAARGGCATGSTGSACARCACAR
GGKCTTTTATGAARGGSWCTAARGGAAGATAGCATACCCCCAGCCCTCGT
```

FIG. 14-5

```
CTAAGCTTGGTAATTCTCATTTGCCTTTGAACGTTAACMAGAAATTCCAG
GCTCAGTAACCAGTTTCAGGAAAATGCTGTGCGTGAATACAAGAGGAGGC
GCCTTGGCATAGGGRAAGCATTCTGTCCTCTTGATGGACAAGATCCTCCA
CTCCCGTCTTGGCCTGTGACACAAACACCTTGAGTTGTAAATTCCTCGAG
CAAAGTGAGGCATTTTGGCATTTGCCAGGGGTGGTGACTGACACACAGGG
AGCCTCAGTACTGTTTATTTGGTGTCTCCATACCTAGCAGACCACATTTT
CCAGGCCCCAAGTAGGGGGTGGGAGGGATCTCATTTTAAAGAGATCAGTT
GATATTTCTCTTGGCAAATCTAGCACAGGACTTTTGTCCCCAAAGACTTC
TGTTCTCACTGCTTGCCCACATGCCTGGGCAGCCTAATGCTCTCTACGCC
CATCTTTCYTTCAGGAATGAGTTCCCATCTCTTTCTCAACAGTGGACACC
ACTCCAGTGTTCCTCCCACCACCTTTAACTGAAAAAACAAACTGCCTTTA
CAGAACACTGTGCACACAGGTCAGCCTGGCTCCTGGAAATGCAAACTGGA
GTTTCAAAAGATGAAAACATTCCTGRAGAATTTTTGGTGTTTTGGAGAG
TGCCTCTGGGCAGATCACACACTTGTGACAAGTTCCTCAATTGTGAAAAT
TCAATCATGCTTTCCACAAAGAACTGACTTTTCACACTTAACACTGGAGG
TTGCTCATTTTCCCCCAAATCTTGAAGTGGATTTGGGATTAAGATACCAA
AGCAAATGCATAGTTCTTTGAGCACTGCTCCTATCTCATGGTGTCTGCAT
ACTGGCAGACAGACACAGGCAGGAAGTAGGGGGCCTCTGCTGATGGTTTC
CTTGGAGTTAGAAAGGTTTGACACATCCAGCCCAGAGAAGGCAGAGGCTC
CTGTAACCCCACCCTGCTGCCAGCTGTCAGTAGAAGAAAAACAGCTGGAG
GAGGGGGGAGATCTCNACACTCCAGTCTCCCTTAATTTGGMAKGGCTTTT
CTGCTAGCAAACTGTATTCTTTCCTTYTTAAAATTATTGGTAATCACAAA
TTCTCATTATTAGGGACATGGGACATTGGGAGAGGAGGAAMCMCTTTATA
TTWAAAAATTTCCGCTTGGTTCCAAGATGGCCGAWTAGGAACAGCTCCAG
```

FIG. 14-6

TCTGCAGCTCCCAGCGTGATCGACACAGAAGACGGGTGATTTCCGCATTT

CCAACTGAGGTACCTGGTTCATCTCATTGGGACTGGTTGGACAGTGGGTG

CAGCCCACAGAGGGTGAGCCAAAGCAGGGCAGGGCATCACCTCACCCAGG

AAGCCCAAGGGGTCAGGGGATTTCCCTTTCCTAGCCAAGGGCAGCCATGA

CAGACTGTGCCTGGAAAAATGGGACACTCCCGCCTAAATACTACACTTTG

CCAATGGTCTTAGCAAATGGCACACCAGGAGATTATATCCCGCGCCTGGC

TTGGCGGGTCCCACGCCCACGGAGCCTTGCTCACTGCTAGCGCAGCAGTC

TGAGATCGACCTGTGAGGCAGCAGCCTGGCAGCGGCAGGGGCGTCCGCCA

TTGCTAAGGCTTGAGTAGGTAAACAAAGCAGCTGGGGAAGCTT

*2-52*

CGGCCGCTCCAGGCCCGGCTCCTGCCCCTCGGCCTCCTCTCCAGGCCCAG

AACTGGTTCCCGTCGGCCTCTCCAGGCCCAGCTCTCCCGGCCACCTCCAC

GGGCCCAGCTCCTGCCTCACGACAACCACGTTCGGCCCAGCTCCTGCCCA

GCTCCTGGCAGCCGTTGTAGGCCCCAGGCTTCCCTGCGTTCAGGCCTCCC

GGACCCACCTTCGGCTTTCCGGCGGCCCTGAGAGACCCGGCTCCTGCCTG

CCAGCGGCCTCTCCCGGCCCAGCTGCGGCCTCACGTCGGCCTCCCCAGGC

CACGTTTCCGCCTGCCTCACGGCAGCCCCGGCAGGCCCGGCTCCGCCTG

CCGGGGCCTCTTGAGGAGGCTCATCTCGTGCCCGGCCG

*2-59*

CGGCCGCGACCCCGCCATCTCTGAGCCACGCCCCTAGCCAGGGCCGCCC

ACCCACTATCACTGAGGCCCACACCTGCTGAGACCCACACCTGCCGAGGC

CCACACCTGCCCAGGCCCACCCATTATCACCGAGGCCCACACCTGCCGAG

GCCCACACCTGGGGGATGGGCAGTCGGGGAGGACGAGTGGTGCCGAGGG

TCTGGGGGGCCCCTGAACCACCAGGGCGAGGTTCCCGGCTGGGGAGACGC

FIG. 14-7

AGAGCCAGGGCTCTGCACAGGGGGTGCCCTGGGGAGCAGGCATGAGAGCC

ACTTCTGCGAGGTGAGGTCACGAGACAGACGTCAACAAGGGCTGGCCAGA

GAGAAGAGCCGGTCACCCAGGGCCTCGGAGGGAAGGAAGGCTCAGGGACC

CGCGGGACGAAGGCTTGGAGAAGCCCCTGGGGAGCAGCTTGAGCACAGCG

AGCTCTGGGACAATGGCCAGTGTCCAGCGACAGGGTGTTCAGAGACGGGG

TGTCCAGCGACAGGATGGGTCCCGGGGACAAGCGGCCG

*2-71*

CGGCCGAAGATCGTGACCGACACGCGCACCTTGGATTTGTCGTAGTTGAC

TTCCTCGACCGAGCCGTTGAAGTCGGTGAAGGGGCCTTCCTTGACGCGCA

CGACCTCGCCGACCGTCCACTCGACCTTGGGCCGGGGCTTCTCGACGCCC

TCCTGCATCTGGTTGACGATCTTCATGACCTCCGCCTCCGAGATCGGGGC

CGGGCGGTTCTTGGCGCCGCCGACAAAGCCCGTCACCTTGGAGGTGTGCT

TCACCAGATGCCAGGACTCGTCGTCCATGAACATCTCGACCAGCACGTAG

CCGGGGAAGAAGCGGCGCTCGGTAACGGCCTTCTTGCCGTTCTTCAGCTC

GACGACCTCTTCGGTAGGCACCAGGATGCGGCCG

*2-75*

CGGCCGCCAGCCCGCCCAGAAGCCACAGACAAGACATAGGTAGCCGTAGT

TGGACTGACGGGCAGGGCCGGCGGGGCAGCCCCCTCCGCGTCCCCGGCCG

*3-2*

CCCCACACCCTCCTCAGCATTTGCCGTCTGTGTCCACGCGACTGCCCCAC

GCCCTCCTTAGCATTTGCCATCCATGCCCATGTGGCCGCCCCACGCCCTC

CTCAGCATTTGCCCTCTGTGTCCCTGCGGCTAGCCAATGCCCTCCTCAGC

ATTTGCCCTCTGTGTCCACGTGGCCGCCCCACACCCTCCTCAGCATTTGC

CCTCTGTGTCCATGCAGCCGGCCCACGCCCTCCTCAGCATTTGCCCTCTG

FIG. 14-8

TGTCCACGCAGCCGGCCCACGCCCTCCTCAGCATTTGCCCTCTGTGTCCA

TGCAGCCGGCCCACGCCCTCCTCAGCATTTGCCCTCTGTGTCCACGCAGC

CGGCCCACGCCCTCCTCAGCATTTGCCCTCTGTGTCCACGCAGCCGGCCA

CGCCCTCCTCAGCATTTGCCCTCTGTGTCCACATGGTCGCCCACGCCCT

CCTCAGCATTTGCTGTCTGTCCACGTGGCCGCCAAGCCCTCCTCAGCA

TTTGCCTGTGTCCACGCAGCCGGCCACGCCCTCCTCAGCATTTGCCCTCT

ATGTCACGTGGCCGCCCACGCCCTCTCAGAATTTGCTGCTGNGACACGTG

GCACCCCATGCCCTCTTAAGATTTGCATNCATGCCCACGTGGCACCCCAC

GCCCTTCTTAAGATTTGC

*3-4*

CAGCTGCTCAGCCGAGGCCGATGCTTCCCACTTTCCCCATGCCCAGGATG

CCACGTCACCTGCAGGTCGCCACGTCACCTGCAGGTCGCCATGTCACCCG

CACGCCACCACATCACCCACAGGTCGTCACGTCACCCGCATGCCGCCACG

TCACCCACAGGTCGCCACGTCACCCACACGTCGCCACGTCACCCGCACGC

CTGGCTGTGGAGGGGGAGTGAAGCCTGTGCTTCCTGCCCATGCCCTCAAC

GCGAAGCAGGTCCCTCCCTCTTCTCTCCTAACTCCTTCCCACTGGCCAGA

AGGCACAATGTCACTTTTAGCTCTGAGCTTCAGATCTGGGTGGAGGGTGG

CAGAACAGCAAGACCCTGGGTTTGGTCCTGGCCACCACAGAGCTGCCTCG

CCACTCGCCGGACCACACACTGGGGCTGTTCATGGAAAGCCGCATCTCCC

ACTGTCCAAGCCCACATGCTGAGCCGTGCAACATGGAACGCAGGTGTCAA

CCTGGGAGTGGCCTGCACTCAGAAACGGAGCAGGCGTGGGGGAAATCATG

GGCGGAATTGGGAAGGAAGGAAGCGCTGAGGAGTGCTGGGCGTGAGCCGT

FIG. 14-9

GCCCACATCAGGGCTGGCGGGGAAGGCACAGAAGGCACAGCCAGAGGGGT

GGGGAAATCTGGGAAGGGGCAGGACACGAAAGCCAGGAGAAGGTTCCCTG

GGACGGAGAGCTCCACAGAGCCACGGCCG

*3-12*

GCGGCCGGGGACCCACGCCATGGTGCCGGGCTATGGGTGTGGGGTCAGCC

AGGGACCCACAACATCGCACTGGCCTGTGGGGTCGGCCG

*3-20*

CGGCCCGCGTTATATGACATTCCACGTTATGTGACATTCCGGTGTGCCGG

CGTGTGGCCGCGTTATATGACATTCCACGTTATGTGACATTCCGGTGTGC

TGGCGTGCGGCCG

*3-30*

CGGCCGTTCTCTGTTACCTCTCTCTGGAGACCCCGGCTTCTCCCCTGAAG

GCCTGGGAGCCTCACCCACGGCCTGGCCCGGAGAGCGGTCGTGATGAGGA

TCAAAAGAAGCAAGGCTGTGGCTGGGACAGGGCACTGCTCGGAGGCCCGC

CCTGGAGGCAGGCGGCCACCAGCCTTCTCTCTCCTTCCCGCACTTTCTCC

GGGCCCCGGTCGCAGGGACCAGCGGGCAGCCTTGGCTCTGGGGCGCCCTC

CTTTCTCCCTGCAGCCCCAGGCGGGCTTCCGGGGGCTGCGCTTCCTCCCC

AGCCAAGGACAGCGCTCACCCGCGCCCCAGTCCCCACGCACCAGCTGTGC

AGCCGCCGCCGCCTCTCTCGTCTCCGTCCAGTGAGTTCTCCGCACTGCAG

AGGGCGAGATCCCGAAGGCCTGGATCCGCGCAGAAGCAGGGAGCACCTTC

CATGGCCGCCGCCATCCTCAGCACCGTCCCGCGGCTGCCGCCATCCTCAG

CACCGGAAGGAAAACCAGGCCGCCGCCATCCTCAGCACCGGAAGGAAAAC

CAGGCCGCCGCCATCCTCAGCACCGGAAGGAAAACCGGGCCGCAGCACGG

FIG. 14-10

CCTTGTTGGGCTCCCTCCGAGCTCTCTGCCGCCTTCATGATCCAGCCCCG

GTCTGACCCCCGCCTCCTTTCTGGCCTTTGTTCCACCCCCTGTCTGAGCC

TTCCCCAGTCCGGACTCGAGGCCGCTCTGTGCAATGCCACCCTTCGCTAC

CCCGCCTGGTCCAGCGGATCCGCCCCAGCCTCTCCAGGCCGGCGCCTCC

TCTACCGGGACTCAGCTGCGCGCTCCTCAACGGGCCTCCCCGGCGGCGTC

TGCGCTGCTGGAGTCGGCGTCCGGCTCCTCCCGAGCACCGGGGCTCCTGC

GGGCTCCGCGGCCG

*1-102*

CGGCCGACNAGGTGTGCGGCACGGGGCCNCGCCAGACTGCAAATGTCATT

ATCTGTTATTTACCACAACAGAGGACGAGAGGCTGCACAAAATTACCGCA

CTTGGCAACGGCCG

CGGCCGGCCCTGCCCACTGGCTCTGCCGTCCCTAGGCAGTGAGGGGCTTA

GCACCTGAGCCAGCAGCTGCGGAGGGTGCTTTGGGTCCCACAGCAGTACC

GACCCAAAGGCGCTGCGCTCGATTTCTCCAGGCGCCTTAGCTGCTACCCC

AGGGACTAGGGCTCGGGACCCGCACCCCGCCATGCCTGCGTCCCAGCCCA

CCCCTTGCCGTGGGCTCCTGTGCGGCCG

*1-c1*

CGGCCGCCANNGGGCCGNCCATGCCGGCCCCGGTGAGCGCGGCATCGCCC

TGCTGGAGTTCGCGGGCGGNACAAGCTTTNGTTCCNGAGCACCAGGCCGC

GNTTCGTCGGGNACCTTGNGCGCNTTANNTGGTTAGGGGCTTNNCNNGAG

GNGGCCCNGGTNCCAGNCNGTNNTTTCATCTCTGNTNNGGTNANCCGGCT

CTNTCCTTGGGACGGGNCGN

*1-e2*

CGGCCGNTGTGGCCACCACGCTCAATGGGAACTCTGTGTTCGGAGGCGCG

GGGGCCGNCTCGGCTCCCACCGGGACGCCCTCGGACAGCCGCTGGCGGT

GGCCCCAAGCCTNGGCTCGTCNCCACTGGTCCCGGCGCCCAACGTGATCC

TGCATCGCACACCCACGCCCATTCAGCCCAAGCCCGCGGGGGTGCTGCCC

GCCCAANCTCTACCAGCTGACGCCCAAGCCGTTTGCGCCCGCGGGCGCCA

CGCTCACCATCCAGGGCGAGCCGGGGCGCTCCCGCAAGCANCCCAAGGC

CCCGCANAACCTGACGTTCATGGCGGCGGGGAAGGCGGNCCAAGAACGTG

GTGCTGTCGGGGCTTCCCCGCNCCTGCGCTGCAAAGCGAACNTNTTCAAN

CAGCCACCGGGCACCANCACCGGAGCGGCCCCGCCGCAAGCCCCCGCGGG

GCCCTTGAANANAACCCATGATCNTTCCACCTTTCTTGAACCCAAGGNAA

GCAGNATTTGTCATTCCCCCGCCCAANNAACATNCCTGTCCGGGCCAAAA

FIG. 14-12

CNCAATTTTNCTACTGNTCTTGGGCACCCCNGGCGGNTGCAGCTTTCCT

GCAGNATTCTTTTAANCNCTTNCCCGGGNCAACNNTGGGGCCGGGNAANA

ACCTNGGCGGGCNGCTTTTTAAAAANTAAGTNGGATTCCCCCGGGGCCTG

GTAAGGAAATNNTNAAATTNNANAGNCTTTATTN

*1-g6*

CGGCCGCCATCTCGCCGTCGTCCGCGGGGTGCCCGGGGCGTTGCTCAGG

CCGGCCACGGCGCCGGGGGAGCTCTTCGGCAACCCGTCCATGTCGCCCGA

GCCCAGGGATCCGCTTACGTGGTGAGGCTCCATCGCGCTCATGGCGGCCA

TGGGGCCCTCCGGGCCAGGGCCGAGCGGGAAATTAGCCCTGCCGGCACCC

GGCCCGATGGGGTTCATGATAGTGTACATGTTTTCACTGGAGTTGGTAGA

ATCTCCAGGGCTAGGCATGATGAGGTGTTCCAGGGGCCCACCTCCTCCT

GGGGGTCCCGTGTAGCTGCCAGGGGATGAGGAGGAGTAGGGGATCGAGTT

TCCACTGGGGCTGGCCCACGGGCCACGAACTCCTGGGCCCATGTTCATGG

CAGGCAGGCCTGGGCCGGCAAGGGAGTTGGGTGGGGTCGCATGCCGCTC

ATAGCTNTGGGGCCCCACGCTGGCATGCCGCGAGGAGGCGTCACCCTNCG

CATTGGGCCGCCATGCTTCGGATGCCCCTTGGGTTCGTGGGGAGGGCTCC

ATGGCGCCAGGGAGGAAGGGATGGGAACCCGGGAGGCCTGCNGGAGCTGA

CTTAACATNCGCAGGGNGGGNCCGGGACCCCCTGGGAAGCGCCGTNACAT

TAAAGGCTNNCCCGTGAAGGCCCATNACGGGGCATTTGG

*2-109*

CGGCCGGAGCATGGGCTTTGCTAATGGTTGGTCGAGGGTTGTGCCCGCCT

CCACCTCAGTAGGCAACTCTGATAAGACACAGAATTGAAGACTCGCGGGC

GGGCTGGGGCCTGCGCAGGCTTCTCCTTCCCAGAGAGATGAACGCGAACG

TCCACAGAAATAAATGGATGGACGCGGCGTTGAAGCTGGAGTATACACAA

FIG. 14-13

TGCCCGCTGTGGAAGCAGCTCACAGTTGTCCTCCAGCGATGGGTGGGTGC

ATGGACCACTGTGGCCGCCGTACAGTGGAGTGGGGTTCAGCCCGAGAGAG

GAGCGACACGCTGGCACGCCGCAGCACCATGCTGTGTGGAAGAGTCAGAC

ACGCAGGAACAGATGCTGTCCCTCTCCTGTGCAGAGCACACGGCAGCAAG

TCCAGAGGGACGGAAAGGAGTTCAGAGGCTGCAGGGCGCGGCGGGGAAT

GCGCGGTGACTGCCGTGGGCGCGGAAGGGGGAATGCGCGGTGACTGCCGT

GGGCGCGGAGGGCGGAATGCGCGGTGACTGCCGTGGGCGCGGANGGGGA

ATGCGGAATGCNCCGTGACTGCCCTGGGCCCCGGANGGGGGAATGCCCGG

TGACTGCCGTGGGCNCGGANGGGGGAATGCCCGGTGACTGCCCTTGGGCC

NCGGAGGGCGGAATGCCCCGTGACT

*2-a2*

CGGCCGCCCGCTCCGGAACACGGCGGCAGCTCATCTGAATTCAAATTACC

CCGGGAGCCGCGCGATGCCAGCCATAACTCAGCCTGCGGAGGAGTGCGGC

CG

*2-c5*

CGGCCGATGTCGGCATCGCGATCGGCACCGGCACCGACGTGGCCGTGGAA

GCCGCCGACGTGGTGCTGATGTCCGGCAGCCTGCAGGGCGTGCCGAATGC

GATTGCGCTGTCCAAGGCCACCATGGGCAACATCCGGCAGAACCTGTTCT

GGGCCTTTGCCTACAACACGGCGCTGATCCCCGTGGCCGCCGGCGCGCTC

TATCCCGCGTATGGTGTCCTGCTGTCGCCGATTTTTGCGGCCG

*2-d10*

CGGCCGGGCTNTTTGATTGGCTGCCGCGTCGGCGATCCACGCCACAATTG

TTCCCTAAGACCGTCTGCCGCCAGCGAGCGCCAGGTGCGGAGCGGGCGTT

AGAAGTTGCTGGCAGTCAGAGGCAGGGGAGCTGTCACTCGCGGCGAGCCG

FIG. 14-14

GGCGGCGGCCAGGGCGCAAAGTTGAGAGCAGTCTCTAGTCTGAGCCTTTC

AGTCGCCTTCCAGTATCATCAGTACCACGGGCTCCACCTTGCTGCGGCCC

CTCAGCAACCCAGTGCACCTGCCACTCGACCAGGTAGGTAGGCCGAGGCA

CCCGGGCGTCGGTCATCGCGCCTTCGCCGCCCTTTGCGGCCG

*2-e12*

CGGCCGAGGTGGTCGGAGTCGCAGGGCCCGTGGAAGGCCTCGGGGAGGAG

GAGGGTGAGCAGGCGGCAGGCCTGGCCGCAGTCCCCCAGGGCGGGAGCGC

CGAGGAGGACTCAGATATCGGGCCCGCGACGGAGGAAGAGGAGGAGGAGG

AAGAGGGGAACGAGGCGGCCAACTTCGACTTGGCGGTGGCCACCCGTCGG

TACCCGGCGGCGGGCATTGGCTTCGTGTTCCTGTACCTGGTCCACTCCCT

TCTCCGCCGCCTCTATCACAACGACCACATCCAGATAGCGAACCGTCACC

TCAGCCGCCTGATGGTGGGGCCCCACGCTGCTGTGCCCAACCTCTGGGAC

AACCCTCCCCTGCTGCTGCTGTCCCAGAGGCTGGGTGCAGGGCTGCAGC

CCCAGAAGGCGAGGGCCTCGGCCTGATCCAGGAGGCTTGCGTCGGTCCAG

GAGGCCGCGTCGGTCCCAGAGCCTGCAGTGCCAGCTGACCTGGCCGAGAT

GGCCAGGGAGCCCGCGGAGGAAGGCCGCAAATGAAAAACCCCAAAAGAA

GGCCGCAGAGGAAGAACTCACAGAGGAGGCCACAGANGAACCGGCCCG

*2-e3*

CGGCCGGCAAGGCTCAGGACCTGCAGGCCATGGAGTGGCGAGGCTGCCAT

GGAGTGGCGAGGCTGCCGTGGAGCGCGGAGGCCGGGTACGCCTGCGCGTG

GAGCGCGAAGGCCGGGTACACCTGCGCGTGGAGCGCGGAGGCCGGGTACA

CCTGCGCGTGGAGCGCGGAGGCCGGGTACACCTGCGCGTGGAGCGCGGAG

GCCGGGTACACCTGCGCGTGGAGCGCGGAGGCCGGGTACACCTGCGCGTG

GAGCGCGGAGGCCGGGTACATCTGCGCGTGGCACGCGGAGGCCGGGTACA

FIG. 14-15

CCTGCGCTCATCGCACACCAGCGCCCACGCCCAGACGTACTCGCGGGAAG

GACAGCNTTTTNTANCNAAAAANCGAATGGTCAACCCGNTTTANTTAACA

CGGGCCANCCCGGAAACAGCCCGACACGGACCGNGACGGGCCG

*3-100*

CGGCCGGCCCAGCCCTGCCATGCCCGCCTCCTCAGGGGAGTACGCCCGCG

CATCGGTGCCGGAGAGGGGAGCCAGGCTGGCCTGCCGGCCG

*3-110*

CGGCCGCATTTTATAGTCAGACACAACCACAACATGGTTGTGACCGGGCA

GTCGAACCCTCAGGATCGACCCAAGAGACATGAAACTACCCACACAAGG

CTGCTATGGGAACATGCACGACACTCCTCCTTCCTAATAGCCAAAACACG

GCCG

*3-e11*

CGGCCGCCTCCAGAGTTTCAATATGGACCTCCGAAGGAGGCACCTCCAC

CTCCATGCCAGTGCTGGTCTCCTGACAAGAGAGGGTTCGCCTACTAACTG

GCATTAGGTGGAACTGTGGCACAGAGGACACGGCCTTCTGACAAGGTTCA

AAGCTGGACGTGAGAGAGAGAGTGGCAGATACACCCTCACTGACGTGAGC

CCCTGGCAGGCAAACGTTTTCCAAAGGCTCGGCTTGGGGAAGCTCCCTTC

CTATTGGCCTTGGCCCTGAGTCTGAGAGAATGGATGCCCAGTGGCTCAAG

AAGGGGCATACAGAGGCAAGGCCTAGGAGGAGAGCAGCCTGCCCTCCCAT

TTCAGAGCGAGGCCCCTGCGTCTTGCCAGCCCTCCTAAGCCCTGGGTGTG

GCGGGATTGAGTGCGAGAGCTGCCAGATGAAACACGTCAGCCCGGCCG

*4-b10*

CGGCCGTCCCCAGGAGAGAAAGAAGCCAGAGAGCATGTCCAAATGCAGT

GCTGGGCCTGTGTGGGGCTGGGGCGGCTGCGGCCG

CGGCCGCGTGTGGGGCCAGGCCCCTCACCTCCCTGTGCTGGCAGCACTGA

CCGAGTGCCTGGGCCCCATTCCCTGAGGATGGGCCACCCAGAGACACCTG

GGCTCAGATGTTCACAGTGGCTGAGAATGGGAAGAGGAGAGGGCAGCTGT

CCTGGGGTGGAGTTTCCGCAGATCACAGCAGGTGGGCAGGGGCCAGGCTC

AGGCTTCTTAGGAACTCGGCCTCTGTCCCACAGAGGGATCTGTCATCTG

TGTGCTGGGGTTCATCATGTCCTCGGGGGTGTGTGTGTCCCTGAAATCCC

TGTCCCCTCTGTCCTCCGTCATGCCCTGCTGGCTGTGGTGGCTACCCT

GTCCCTNTGGCCCTGGGTAANCTTGGCAGANNCCGGNTTTCTTTNGCTTC

CAAATAAAGGAATANACCCCAAAGGGTCATTCTCTAACATGGTCAGGAGG

AGGGCTCTGGGAGAGGTGTCGCTGTGACTGTGGGCTCATGACANGCATGA

ACCCCTTGNGGGAAGCGGGGGCCCCCTGTGATCCCTTTCTATTCATTTTC

TTCGTCTTTCCCCACAAAATGCTGTGTGCTGTGGACCCACCTTGGGGNTC

ATGGAGTGGGCCACCGGGGGCCCACCCTAAACACTTGTTGCNCCAANGGT

CGNCCCGCCTTCTGNTTGNGGGTCCCCCGTGCCCCT

*4-c10*

CGGCCGTCTCCAGGAAGGACAGCCTGGCAGGCCCCGGGGGTCCCTTGGCT

TGGAGCCCCCAGCCCAAAGTCCCCTCCTTTCTCCAAGATGGGGTGGCTG

GTAGCCAGGGTGGTGGGTACCTACTGCACACGTAGGGAAACTGAGGCCAG

GGAGGCCCACCCAGACCTTGCCCTGGCCCACTGACCTGTAAGCGTCCACC

GTGAACCCGCTGCCCACTGGCCCCTGTTCCCCCACGGGCCTTCCCTGCC

TAGCCCAGGCCCCACCCAGGCCCCTGTCACCTCAAAGGGCTCCCCCGGGG

CCAGCGGGAAGATGCTAGACACCTGCTCCGGGCCCCAGCGGCCG

CGGCCGCCAAGAAGGCCGCGCCCGCGAAGAAGGGCGTCAGCCGCGTCGTT

GGCAGCAAGACACCGGCCACCAAGACCATCAAGGNCGGCGCGGCCAAGCC

GGTGGCGAAGAAGGCGGCTCCGGCCAAGAAGGCTGCTCCGGCCAANAAGG

CGGCGCCCGCCAAGAAGGTCGTCGCCACGAAAGCCCCGGCCAAGAAGGCT

GCAGCCAAGAAGGGCTGATGCGTCTCCTTCTAGTCGCCGTGGGCCAGCGC

CAGCCGGCCTGGGCCGACACGGCCATGAAGACTTCGCCAAGCGCTTTCC

GCCCGAGCTGAGGCTGGAGCTGAAGGCCGTCAAGGCCGAGACACGCGGCA

GCAAGACGGCCG

*4-g6*

CGGCCGTCAGCCATCGTAATGACATGTCTGTGGGTTGCCCTGTGCCGCCA

GGCTGGGCTGTCGGAAGCACCCAGCGACGTGTCTGTGGGTCCGCCCCGTG

CCGCCAGGCCGGGCCATCGGAAACACCTGCAGTAACCGGAGTGCCCTCGC

TGATAGCCCTTGTTCCGGGGCCTCGTCCTGGGCTGTGCAGAGCTCCAGCC

CTAGCCCCAGCCCCAGCTGCAGGCGGCCG

FIG. 14-18

Clone 2-12 Glioma tumor suppressor candidate gene 19q13.3

TGGACTCACCGCGGTGGCNGCTGACGCCAGCGTCACGGGCTCCGAGGGGC
CAGCCCGCCCGAGGCCAGGTAGCCGCTGACGGGCACCTGCTTGGCCAGGA
GCTGGGAGGTGGGCGTGTTGAGCGCCATGACGGGCTGGCCCACCACCTGG
ATGGGCGCCAGGCCCAGCGTGGCCGCCGTGGCACCCCAGGGCTGCCATT
GGGCAGGCCTTGGAGGCCCGGGATGGGCTGCAGTGTCACATTGCCCAGGC
CCACAGGCTGCAGGAAGGGCTGCACACTCAGGGCCTTGTTGACCACGTCC
TGGGGCGGCACCAGGGCCTGGTGGGTCAGCACGGTGGGCGGGCCCTGCA
GCCCCAGCAGGTCGGTGCTGCTGGGAAGAGGGCTTGGGGCCCCGCAGCCA
C

Clone 2-36 Zn-finger protein and novel arginine vasopressin w/ 9 CpG islands Chr. 20

CCGCGGTGGCGGCCGCCCCGTCTGGGAGGTGGGGAGTGCCTCTGCCCAGC
CGCCACACCGTCTGGGAGGTGAGGAGCGCCTCTACCTGGCAGCCCCATCT
GGGAACTGAGGAGCGCCTCTGCA

Clone 2-37 Relaxin 1 w/ 4 Cpg islands Chr. 9p23-24.3

CGGCCGGGCAGAGGCGCCCACTTCCCAGACGGGGCGGCCAGGCAGAGGC
GCTCCCCACCTCCCAGATGAAGGGCGGCTGGGCAGAGGTGCTCCCCACCT
CCCAGGCGGGG

Clone 1-1 Chr. 7q21.2-q31.1

CGGCCGAGATGCACTCAGATTTATGTTGTGAATTTGTTATGTTCAGGTAAT
TTGATGGTGTATTCTTATGCAATGAGATCTGGATGTCATTTCTGGTTCTGCT
AATTAGAACATCTGTGACCTTGATCAAGCAAGAACTTTCTCTCTTGTGGAC
CTCACATCCTACAATTGTATATTGTCCTGCATGTCCCTCAGACACTTTTCGT
TTTTCTTCAGTCTTTTTTCTTTTTGTCCTTTAGATTGGATAATTTCTGATCTT
CTGAGAATTTTTTTATTATCTGCAACTTGCTGGGTTTTTCTTAGAATTTCAG
TTTATTTTTTGTATTTTTTA

Clone 1-19 Chr. 11

AGGGGTGCCTCTGCGCCCTAAAGAAACCGGGGGAGCCCCACAACCCCTCC
CCCACCAGGACACTAAAAGGCAAGCTTTCGGTACAGTGAGACATCAAAGC
CTCCTAGGCCCTGAGTCAAAGGTATAGCCGTGTAATATCCCAGTGCCAGC
TCTCCGGCTGCGGGGAGCCTGGCGCAAAGCTTCCAAGCCTTCCTTGTTCAA
AAA

Clone 2-16 Chr. 21q section 981105

FIG. 14-19

TGGACTCCCCGCGGTGGATGCCGCCGGGGCAGCCGAGGCGAGGACTGCG
GGGAGCTGACGGGTGAGTAGGGCANGGACGGGCAGATGCAGCGTNCGTT
CATGTCCAGGCTGCCACCGGCTGCCAGCCCACCCTGGGACCGCTCTTGCA
GAGACAGCTTGCGACCGGAGAGGTGGGGCCGGGCCTGGGACCCGGAGGA
GTCAAGGGGGACCTCTTGGCCATCGGCCTCCAGGGGCCGGCCACCTGCAG
TTTTGGGGCCCAGCTGGAGGTCAGCAGGGTGGACTCACAACCCCCTGAGT
TCAGGTACAGGGAGCTGTGGAGACAGGCCCACCCAGGCTGACCTTCCCCA
NAGCCTTGCTGTCACGGAGAGGAGGGGCGTTGGAGGAANGGCCACAAA
TGCNNGAGAGGGGCAATGGCCTGNACAAGATGGAGAACAGCCACCCG
TTCCCCAGTACAGCCAGGTCANGACACGGATCCANCAAGCCCTTTGGAT
GGGGAGACTGAGGTACAGCTGATGACTCACCCTATGTGATACCAGCTGTG
AGAGCCGGAGTGGGGATGCANACACGGAGGTGGCCAGTGGNCACCTNCN
AAGACTCAACATCCANGGCGATGACGCCAAACAGTCAAGGCGTNAGAAC
CCCCNANANNAAGAGTGAGTGNCATTCACCTAATA

Clone 2-2 Chr. 1qtel 1920-c104t3

CGGCCGGGCGGAGGGGCTCCTCACTTCTCAGACAGGGCATTCGGTCAGAG
ATGCTCCTCACACCCCAGACGGGGCGGTGGGGCAGAGGCGCTCCCCACAT
CCCAGACGATGGG

Clone 1-12 Chr. 16 clone LA16-305F3 (2CpG islands)

CGGCCGCGGACCCCCGACCTCGACCCAAACTGCATGCGGCTGAGGACCCC
CAAGCCAGGCAGACGCCAATCCAGACCCCACGNNNNNNNNNNAAGANCG
GTTTTTTTGCCCTTTTGACGTTTGGGAGTCCCACGTTCTTTTAATAGTGGGA
CCTCTTTGGTTNCAAAAANNGGNAANAT

Clone 1-7 Chr. 16 clone LA16-361A3 ( 2 CpG islands)

CGGCCGGTGCCAAAGGTCCTGTGTGCCCAGAAGAAGTGAATGGTTTNGGC
CAGGTCAGGCAGAAGGACCTGGTTGTGGCAGCGCTGACAAGAGAGCACC
CCAGATCCATCCCTTACAAAATGATCGAGGGGCTTCTTCCAGAGGGCACC
GTCTGGTTCCCTGAGGGGAGTGCAGCAGCCCTGACATAGCCTTCAGGAGC
CGTGGCAGAGCTGCAGAGGGGACCCCAGCAGTGGGGCCCTGACAAGGAC
GAGGTGCACCACCATGGGGCTTCCCACTGAACTCTCGGCGCCAGGACGAG
CCAAGGGACGGGGCGGCGCCCANCCCANACTCAAGCTCAGGTCCCTTGG
GTCCCCGCGGGGGACACCTTCGACAGCAGGTTCCTGGGGCCACCTTCTGC
CCCACACCATGAGANAAACATTGCAGGACGAATTNCTNCTTTGCCCCGC
AGCCCACGCCGCCTNTTTCCAAGGTAGGCCCTNGGCCCTGGCCCCATTGA
ACGAACGGGCAAGCCNATTAAGGGCNGGNNTTNTGGGAANNCCTGGGG
GGGCCAANCCCCTTTTTGGNTTTCTTTGGGGCCTGGAAACCTTCNACAAT
NGGGNCCCCTNGGGGGGGCCTTTTTNAAAGGGAACCCTTTTTCGGGGG
GNGGGTTTGGTCTTNGGGGGGGGNCCCCTGGGGGGGGNGGGGGGGAATC
AACTTGGCAAAAACTTCGGGGNAAACCCTNGGGGCTTTTTNGGGCCCGG
TTTTTAAAAACTAAGTGGGGAATCCCCCNGGGCTTGGAGGGAATTCNAT
ATTCAAGNCTTATTGANTACCCGGTCGANCTTGGNGGG

Clone 1-5 KIAA 0614

FIG. 14-20

CAAAACTGGAGCTCCACCGCGGTGGCGGCCCGTCACGCACTCCACATTCT
GCAGCTCCCGCAGCCGCAGGCTCCGGATGGCTGCCGCGTAGATGTCCTTG
TTCTCCCACCTGCCCGGGTGAGGAGCACAGGTGAGGGAGAACACCGCCGA
AGAGGCTGGGTCTGGGGGCCACACCCACTCAGCTGGAGGTCCCGGATCCT
CTCTTGGGAGAGGCCTGGGGCCCAGCCGCCCTGGTCATCCCAGTCCTTTCC
TGCCTCTGGTGCCGCCGCCTCAGAGCTGCTGTTTTCTTAGTAAACCCCTTC
TGCTGAGGACCCTCTTTCTTGGCACCCACCATCCTGCCTCATCTCCCTCTCC
TGGTGAAATCCACCTGTCACCTGACCTAGGTCCTCGTGTCATTGCCCAGGA
ACAGATGCTGCTGTCATACCCTGGCTGGCTGGCCGGGCCAGCCCCTGCCA
GCCCCTGACACGCGCACACACTCACGCCACAAGGATGTGCCGGCCCCGGC
TGACAGCTCCACCTTCTCGCCCGTCATGGTCAGGTAGGTGAACCTGCAGC
AGGGCTTGTTGGGGCTGTCAAGGGCTCTTCCGTGGCCAGGTGCTGGGANG
CGAATCTTANCGCACAAGGGGCCTNCAAGCTTCGGGTCTTAATNATTTGA
ATCTGGGAAGGGGTGGGANGGCAAGAAACCNAGGGCTTTATTTATGAAG
GGCCATNGGGAAGGNGGGAACCCTTGATCCCCCAAGGTNGGGGTNGGGT
AAAT

Clone 2-43 cDNA FLJ12750

CGGCCGCCTTGACCCAGGCTACCCTTAGCCAATATCCTCTGCCCCTGGGTG
GCTGGTGGCTGGGCCTCAGGGTGGGCAACGTTAGGGGTTTGGCGAAAGCC
CGCCCCATGGGATTGAGGGACGGGGCTGCACTCCAACCGTCTGCACCTGC
TCTTCCCCCACCCCTGTGGGACCTCATCTTCACGTGCCATGTGTGCTGAAG
GCCCAGGGCCCAGCAGGGGCAGTGGCACCTGTTGACGGAAAAGGCCGA
GGTGCTTACCAGTGGACCTTCTGGCCCGCCCCTCCCCTGTCACTTGTCGGG
CATCCAGGGCCCCGACCTGTGCCTAGCCGCCAGGGTGACAGAAGGCAGAA
CTGAAGCGGGGTCTGGGCCACGGGCCAGGCCACTGCCTTTTGTCCTCAGT
GACCATACATTCCTGCTCTCGGACTTGAACTCTACTGTAACTGTTTTCTTG
AAATGAAGCTGTACAGGACGATTCACTGCCATGCCAGTCAGGCGGGCTTG
CCATGTTCTGTGAATCTCGAGTGAGCGGTGCCACCCGCCCCCATACCTCCG
CCAC

Clone 2-48 RP11-393 M18 Chr.1

AAANCTGGNCTCCCCGCGGTGGCTGCCCGGGCAGAGGCGCTCCTCACTTC
CCAGATGGGGTGGCTGGGCAGAGGCGCTCCTCACATCTCAGACAATGGGC
GGTCANGCAGAGATGCTCCTCACTTCCTATACAGGATGGCGGCCAGGCAG
AGGCGCTCCTCACTTCCCATTCAGGGCAAGCCGGGCAGAGGCGCTCCTCA
CTTNCTCCCANATGGGGCGGCCCGCTCTTATAACTANTGGATCCCCCGGGC
TTGGAGGAAATTCNATATCAAGCTNATCGATACCGTCGGACCTNAAGGGG
GGGGGCCCGGNTACCCCAAATTCGCCCTATAGGNGAGTTCGGAATTTAC
GCCGCCGCTTAAACTTGGGCCCGNANATNTTTTTACCAAACGGTTCTTTG
NAACCTNGGGGNAAAAAAACCCCNTTGGGGCGGGTTTAACCCCCCAAACC
TTTTNAAATTCCCCNCCTTTGGGCAAGGCNAAANAATTTCCCCCCCCCNTT
TTTTTGGNCCCAAGCCCTTGGGGCCGGTTNAAATTAAACCCCNAAAAAAA
AAGGGCCCCCCGCCAACCCCTTNNTTCCGGCCCCNTTTTCCCCNAAAAC
AAGANTTGGCCGGCCAAAGCCCNTGGNAAATTGGGGCGAAAANTGGGGG
AACCNCCCCCCCCTTGTTAAGCCGGGGCCGNCAATTTNAAANCCGCCNG
GNCGGGGTTGGTTGGNTGGGTTTTACCNCCGCCAANCCGTNGAACCCGCT

FIG. 14-21

TACCAACCTTTGGNCCAGCGGCCCCCTTAACCGGCCCCCNGNTTCCTTTTC
CGCNTTTTCCTTTNCCCTTTTCCTTTTCTTNGGNCCNCNNTTTCCGCCCGGC
TTTTTTNCCCCCTTCNAAGGCTTCTTAAAATCGGGGGGGCTTNCCCTTTTA
AGGGGTTTNCCGAATTTAAN

Clone 2-52 BAC in Chr.14

TGGACTCCACCGCGGTGGCGGCCCGCCCATCGTCTGAGATGTGGGGAGTG
CCTTTGCCCCGCCGCCCCGTCTGGGATGTGAGGAGCGCCTNTGCCCAGTCG
CGACCCCGTCTGGGAGGTGAGGAGCGTCNCTGCCCANCCGCCCCATCTGA
GAAAGGAGGAGACCCTCCGCCTGGCAACCGCCCCGTCTGAGAAGTGAGG
AGACCCTCCGCCCGGCAGTCGCCCCGTCTGAGAAGTGAGGAGCCCCTCCG
CCCAGCAGCCACCCCGTCTGGGAAGTGAGGAGCGTCTCCGNCCGGCAGCC
GCCCCGTCCGGGANGGAGGTGGGGGTCAGCCCCCGCCAGGCCAGCCGCCC
CGTCTGGGAGGGAGGTGGGGGGGTCAANCCCCTTACCGGCCNGTCNTTTC
GTTNTGTNGGTTAGG

Clone 2-64 12 BAC RP11-588G21

TGGGCTCCACCGCGGTGGCNGCCGTGGCTCTGTGGAGCTCTCCGTCCCAG
GGAACCTTCTCCTGGCTTTCGTGTCCTGCCCCTTCCCAGATTTCCCCACCCC
TCTGGCTGTGCCTTCTGTGCCTTCCCCGCCAGCCCTGATGTGGGCACGGNT
CACGCCCAACACTTCTTAAGCGCTTCCTTCCTTCCCAATTCCGCCCATGAT
TTCCCCCACGCCTGCTCCGTTTCTGAGTGCAGGCCACTCCCAGGTTGACAC
CTGCGTTCCATGTTGCACGGCTCAGCATGTGGGCTTGGACAGTGGGAGAT
GCGGCTTTCCATGAACAGCCCCAGTGTGTGGTCCGGCGAGTGGCGAGGCA
GCTCTGTGGTGGCCAGGACCAAACCCAGGGTCTTGCTGTTCTACCACCCTC
CACCCAGATCTGAAGCTCAGAGCTAAAAGTGACATTGTGCCTTCTGGCCA
GTGGGAAGGAGTTAGGAGAGAAGAGGGAGGGACCTGCTTCGCGTTGAGG
GCATGGGCAGGAAGCACAGGCTTCACTCCCCTCCACAAGCCAGGCGTGC
GGGTGACGTGGCGACCTGTGGGGTGACGTGGGCGACCTGTGGGTGACGTT
GGCGGCATTGCGGGTGAACGTGACNACCTTGTGGGTGATGTGGTGGCNTT
CCGGNTGACATTGGCNACCTTCAAGGTG

Clone 2-65 RP11-402B2

CAGTAAAGATTCAATCAAATAAGGAGATATCTGAGAGAGACAGAGAGA
GAGAGAGAGAGAGAGAAACAATAATAAATGTCTCCAAATAAGAAGTCAT
TTATCTAAACTGTTTGAACATCAAATAGCAGGGCTTTTTTTTTTTCCTTTTA
TCTCACAAGACCACTGTCTGCTACCTAAAATTTAGAAGGAATAAAAACTC
TGAACTTAGATTGAGGCTTCCAAACCACAGAGCCAAACCTCAACTTCAG
AAATTCCTGGCAAACTATGTATTAGCTAGTACATGATAAAATGAAACCTC
CATCCTTGTTAATTCCTTACGTGCAGAGCTGTTCATATTAAATAATGTCTCT
TTTGTTTTACTCATGCTTTGTTTTTACTTATACTTACGCATTTCTGAACAA
ACGATAGCAAAGCAAAAAAAACAAAAACAAAAAAAAAACCTTTATTCAG
TTCATCCTAA

Clone 2-70 RP11-349E11 from 7p14-15

FIG. 14-22

TGGACTCCCCGCGGTGGCGGCCGGGCAGAGGCGCTCGTNANTTCCCAGAC
GGGGCGGCCAGNAANAGGGGCTCCTNACATCCCANACGATGGGCAGNCA
GGCAGAGACACTNCTCACTTNCTATACAGG

METHODS OF ISOLATING METHYLATED CPG ISLANDS

CROSS REFERENCE TO RELATED APPLICATIONS

This application is a continuation application of U.S. application Ser. No. 11/084,085 filed Mar. 17, 2005, now U.S. Pat. No. 7,488,815 issued Feb. 10, 2009; which is a continuation application of U.S. application Ser. No. 09/861,893 filed May 22, 2001, now issued as U.S. Pat. No. 6,960,434; which claims the benefit under 35 USC §119(e) to U.S. Application Ser. No. 60/206,161 filed May 22, 2000, now abandoned and to U.S. Application Ser. No. 60/206,158 filed May 22, 2000, now abandoned. The disclosure of each of the prior applications is considered part of and is incorporated by reference in the disclosure of this application.

GRANT INFORMATION

This invention was made with government support under Grant No. CA65145 awarded by the Institutes of Health. The U.S. government has certain rights in this invention.

BACKGROUND OF THE INVENTION

Genomic imprinting is a parental origin-specific gene silencing that leads to differential expression of the two alleles of a gene in mammalian cells. Imprinting has attracted intense interest for several reasons: (i) Imprinting is by definition reversible and may be regulated over a large genomic domain (1). (ii) Imprinted genes and the imprinting mechanism itself are important in human birth defects and cancer (2). (iii) It has been suggested that imprinting cannot be reprogrammed without passage through the germline and thus constitutes a barrier to human embryonic stem cell transplantation (3).

Experimental studies of the timing and mechanism of genomic imprinting have been hampered by the fact that imprinting requires passage through the germline, analysis of which poses a difficult experimental target. Thus, there is a need in the art for an experimental model system which allows direct examination of allele-specific gene silencing in the dynamic process of genomic imprinting.

DNA methylation is central to many mammalian processes including embryonal development, X-inactivation, genomic imprinting, regulation of gene expression, and host defense against parasites, as well as abnormal processes such as carcinogenesis, fragile site expression, and cytosine to thymine transition mutations. DNA methylation in mammals is achieved by the transfer of a methyl group from S-adenosylmethionine to the C5 position of cytosine. This reaction is catalyzed by DNA methyltransferases and is specific to cytosines in CpG dinucleotides. 70% of all cytosines in CpG dinucleotides in the human genome are methylated and prone to deamination, resulting in a cytosine to thymine transition. This process leads to an overall reduction in the frequency of guanine and cytosine to about 40% of all nucleotides and a further reduction in the frequency of CpG dinucleotides to about a quarter of their expected frequency (35). The exception to this rule are CpG islands, that were first identified as HpaII tiny fragments (36), later to be defined as sequences of 1-2 kb with a GC content of above 50% and a frequency of CpG dinucleotides greater than 0.6 of their expected frequency (37). CpG islands have been estimated to constitute 1-2% of the mammalian genome (38), and are found around the promoters of all housekeeping genes, as well as in a less conserved position in 40% of tissue specific genes (39). The persistence of CpG dinucleotides in CpG islands is largely attributed to a general lack of methylation, regardless of expression status (reviewed in ref. 40).

The two exceptions to the rule of CpG islands being unmethylated in normal cells, are on the inactive X chromosome (41) and in association with imprinted genes (42,43). Genomic imprinting is the differential expression of the two parental alleles of a gene, and most imprinted genes are associated with at least one CpG island methylated uniquely on a specific parental chromosome (42). In addition, aberrant methylation of CpG islands has been observed in tumors and cultured cells, and it is thought to be a mechanism to silence tumor suppressor genes (44,45).

Numerous approaches have been used to identify CpG islands that are differentially methylated in specific cell types, such as tumor-normal pairs for cancer-related methylation changes (46-48), or differential parental origin for imprinted genes (49-50). However, there was only one report of a systematic effort to identify CpG islands throughout the genome that might be normally methylated (51) using a methyl-CPG binding column. However, the resulting sequences were mainly dispersed repeats, ribosomal DNA and other repeated sequences with no characterization of unique, methylated CpG island.

There is a need in the art for identification of unique, methylated CpG islands so that imprinted genes can be identified.

SUMMARY OF THE INVENTION

One embodiment of the invention provides a method of forming embryonic germ cells useful as a model system for studying imprinting. A male and a female mammal of the same species are mated to form a pregnant female mammal. The male and the female mammals are sufficiently genetically divergent such that at least 50% of genes in resulting offspring have at least one sequence difference between alleles of said genes. An embryo is obtained from the pregnant female mammal at a stage of embryonic development between when 2-3 somites become visualizable and when gonads are recognizable. The embryo is dissected and cells of the embryo are dissociated. The dissociated cells are cultured to provide embryonic germ cell lines.

According to another embodiment of the invention a method is provided for inducing imprinting in vitro. Mammalian embryonic germ cells are cultured in suspension culture under conditions in which the embryonic germ cells differentiate. Expression of one or more imprintable genes changes from approximately equal biallelic to preferentially uniparental.

One aspect of the invention provides a method of inducing imprinting in vivo. One or more mammalian embryonic germ cells are injected into a nude mouse. The embryonic germ cells differentiate and form a teratocarcinoma. Expression of one or more imprintable genes changes from approximately equal biallelic to preferentially uniparental.

Another aspect of the invention is a method of inducing imprinting in vivo. A mammalian embryonic germ cell is injected into a blastocyst of a mammal. The blastocyst is injected into a pseudopregnant mammal so that the blastocyst develops into a chimeric mammal. Expression of one or more imprintable genes in somatic cells derived from the embryonic germ cell becomes preferentially uniparental.

According to still another aspect of the invention an isolated and purified mammalian embryonic germ cell line is provided. It expresses one or more imprintable genes in a biparental fashion. It forms cells which express one or more imprintable genes in a biparental manner. It differentiates to form cells which express said one or more imprintable genes in a preferentially uniparental fashion.

According to another embodiment of the invention a method of testing substances as candidate drugs is provided. An isolated and purified mammalian embryonic germ cell line as described above is contacted with a test substance. Imprinting of one or more imprintable genes is assayed.

Another embodiment of the invention provides a method of testing substances as candidates drugs. Isolated and purified mammalian embryonic germ cell line as described above are contacted with a test substance. Methylation of one or more imprintable genes is assayed.

According to still another aspect of the invention a method is provided for making a chimeric animal which can be used as a model system for imprinting. A mammalian embryonic germ cell is transfected with a vector which expresses a detectable marker protein. The embryonic germ cell expresses one or more imprintable genes in a biparental manner. The transfected mammalian embryonic germ cells is injected into a blastocyst of a mammal. The blastocyst is implanted into a pseudopregnant mammal. The blastocyst develops into a chimeric mammal. The chimeric mammal expresses the one or more imprintable genes in a preferentially uniparental fashion. The present invention also provides chimeric mammals made by the process.

Still another aspect of the invention provides a method for isolating methylated CpG islands. Eukaryotic genomic DNA is digested with a first restriction endonuclease which recognizes a recognition sequence found in A/T rich regions of DNA or found in CpG island-poor regions of DNA. The eukaryotic genomic DNA is digested with a second restriction endonuclease which recognizes a 4 base-pair sequence in unmethylated C/G rich regions. Fragments of at least 1 kb formed by the step of digesting are isolated and the fragments are inserted into bacterial vectors. Non-methylating, non-restricting bacteria are transformed with the bacterial vectors to propagate the vectors and render the fragments' progeny unmethylated. The unmethylated fragments are digested with a third restriction endonuclease which recognizes a sequence of at least 6 base pair in G/C rich regions. The resulting fragments are isolated and inserted into bacterial vectors to form a library of sequences which are enriched for sequences derived from methylated CpG islands in the eukaryotic genome.

Also provided by the present invention are a library of fragments which are enriched at least 100-fold in methylated CpG islands relative to total genomic DNA.

Further aspects of the invention provide a method for testing substances as candidate drugs. A nude mouse which has been injected with an embryonic germs cell to form a teratoma is contacted with a test substance. A test substance is identified as a candidate drug if it inhibits the growth of the teratoma or causes regression of the teratoma.

The present invention also provides a method of providing an assessment of risk of developing cancer. Methylation status is determined in a sample of a patient for a CpG island selected from the group identified in Table 2 (below). The methylation status of the CpG island is compared to that found in a control group of healthy individuals. The patient is identified as having an increased risk of developing cancer if methylation status of the CpG island is perturbed relative to the methylation status in the control group.

Another aspect of the invention is a method of providing diagnostic information relative to cancer. Methylation status of a CpG island selected from the group identified in Table 2 is determined in a sample of a tissue of a patient suspected of being neoplastic. The methylation status of the CpG island is compared to that found in a control sample of said tissue which is apparently normal. The patient is identified as having an increased risk of developing cancer if methylation status of the CpG island is perturbed relative to the methylation status in the control sample.

According to yet another aspect of the invention an isolated and purified methylated CpG island is provided which is selected from those shown in Table 2.

Still another aspect of the invention provides a method of identifying imprinted genes. A gene is identified which is within about 2 million base pairs of a CpG island identified in Table 2 in the human genome. One determines whether the gene is preferentially uniparentally expressed. The gene is identified as an imprinted gene if it is preferentially uniparentally expressed.

According to another aspect of the invention an isolated and purified methylated CpG island is provided. Surprisingly, the island is methylated in both maternal and paternal alleles of a human.

Another aspect of the invention provides an isolated and purified methylated CpG island which is biallelically methylated in some humans and not biallelically methylated in other humans. The methylated CpG island thus comprises a methylation polymorphism.

The present invention thus provides the art with tools and methods for accessing imprinted genes and using them for detecting birth defects, diabetes, and cancers associated with aberrant imprinting.

BRIEF DESCRIPTION OF THE DRAWINGS

(FIG. 2A) Colony of EG cell line SJEG-1 cultured on a feeder layer of STO cells, viewed by phase contrast microscopy. (FIG. 2B) EG colonies stained positive for alkaline phosphatase. (FIG. 2C) Embryoid bodies formed upon spontaneous differentiation on plastic, viewed by phase contrast microscopy. (FIG. 2D) A rhythmically contracting muscle bundle formed by differentiation of SJEG-1 cells transfected with αmMHCneo vector. (FIG. 2E) Erythrocytes, epithelia, and (FIG. 2F) striated muscles in H&E sections of teratocarcinoma formed after injection of SJEG-1 cells into nude mice. Scale bars: 10 μm in FIG. 2A, FIG. 2B, and FIG. 2D; 100 μm in FIG. 2C, FIG. 2E, and FIG. 2F.

(FIG. 3A) SSCP analysis of allele-specific expression of Kvlqt1, Igf2, and L23mrp. Paternal (Castaneus) and maternal (129) bands are indicated. The upper band is a nonspecific PCR product. (FIG. 3B) Changes in ratio of parental allele expression of Kvlqt1, Igf2, Hl9, Snrpn, Igf2r, and L23mrp. Means and standard deviations are calculated from 4-7 experiments each.

FIGS. 4A and 4B. Independence of imprinting establishment from method of in vitro differentiation. (FIG. 4A)

SNuPE analysis of allele-specific expression of Snrpn. SJEG-1 cells were differentiated with all-trans retinoic acid (RA), dimethyl sulfoxide (DMSO), and in methylcellulose medium. Cells were harvested at 12 and 20 days of differentiation. (FIG. 4B) SSCP analysis of allele-specific expression of Kvlqt1 in αmMHCneo-transfected SJEG-1 cells that were differentiated into cardiac myocytes.

(FIG. 5A) FACS analysis of SJEG-1 and SJEG-1/GFP18-1 cell lines for GFP fluorescence intensity. SJEG-1/GFP 18-1 was derived from SJEG-1 by transfection with pEGFP-N3 vector and injected into the blastocyst of C57BL/6. (FIG. 5B) FACS analysis of spleen cells isolated from a chimeric mouse and a non-chimeric littermate. Cells with fluorescence intensity greater than 40 units were collected, since the fluorescence intensity of >99.9% of cells derived from donor embryos fell below 30 units. (FIG. 5C, FIG. 5D, FIG. 5E) Analysis of allele-specific expression of (FIG. 5C) Kvlqt1 and (FIG. 5D) Igf2 by SSCP, and (FIG. 5E) Snrpn by SNuPE, in GFP+ spleen cells obtained from chimeric mice. Paternal (Castaneus) and maternal (129) bands are indicated. The upper constant band in (FIG. 5D) is a nonspecific PCR product.

FIGS. 6A and 6B. De novo establishment of allele-specific methylation of HI9 and Igf2 in EG cells by in vitro differentiation. (FIG. 6A) Analysis of H19 DMR. Genomic DNA was digested with EcoR I (E), Msc I (M), and Hpa II (H), and hybridized with a 450 by probe, resulting in a 2.6 kb band representing methylated DNA, and a 1.74 kb band representing unmethylated DNA. The ratios of unmethylated to methylated bands were 4.3, 2.3, 1.3, 1.2, and 0.83, at 0, 6, 10, 13, and 16 days, respectively. (FIG. 6B) Analysis of Igf2 DMR2. Genomic DNA was digested with BamH I (B) and Hpa II (h), and hybridized with a 640 by probe resulting in a 2.45 kb band representing methylated DNA, and several lower molecular weight bands representing unmethylated DNA. An unrelated cross-hybridizing band (C) variably appears as described previously (16). The ratios of methylated to unmethylated bands were 4, 4.8, 1.6, and 0.9, at 0, 10, 13, and 16 days, respectively.

(FIG. 7A) Monolayer culture of differentiated human EG cells (LV.EB) obtained from previously reported human EG cultures (21) under phase contrast microscopy. Scale bar, 10 μm. (FIG. 7B) Nearly complete monoallelic expression of IGF2 in differentiated human EG cells. PCR products of genomic DNA were digested with Apa I revealing heterozygosity for A (236 bp) and B (173 bp) alleles. Digestion of RT-PCR products (+RT) shows nearly complete preferential expression of the A allele, with no product in the absence of reverse transcriptase (−RT). (FIG. 7C) Complete monoallelic expression of H19 gene in differentiated human EG cells. Digestion of PCR products with Alu I resulted in both digested (128/100 by doublet) and undigested (228 bp) alleles in genomic DNA, and only the undigested allele (148 bp) in cDNA. (FIG. 7D) Analysis of H19 DMR of differentiated human EG cells. Genomic DNA of differentiated EG cells (LV.EB) and a control tissue was digested with Sma I (H) and Pst I (P) and hybridized to a 1 kb probe, resulting in a 1.6 kb band representing methylated DNA, and a 1.0 kb band representing unmethylated DNA.

FIG. 11A) MCI-S are methylated in blood. FIG. 11B) MCI-S/1-19 is methylated in fetal and adult somatic tissues. FIG. 11C) MCI-S are methylated in uniparental and germline tissues. fCNS: fetal central nervous system; fKI: fetal kidney; fLU: fetal lung; fSK: fetal skin; BR: brain; CO: colon; KI: kidney; LI: liver; OT: ovarian teratoma; CHM: complete hydatidiform mole.

FIG. 12A) MCI-D are methylated in blood. FIG. 12B) MCI-D/2-78 is methylated in fetal and adult somatic tissues. FIG. 12C) MCI-D methylation in uniparental and germline tissues: MCI-D are methylated in maternally derived tissues and germline, unmethylated in sperm and complete hydatidiform mole, and half-methylated in adult testis. fCNS: fetal central nervous system; fGU: fetal gut; fHE: fetal heart; fKI: fetal kidney; fLU: fetal lung; BR: brain; CO: colon; HE: heart; KI: kidney; LI: liver; OT: ovarian teratoma; CHM: complete hydatidiform mole; OV: ovary; fOV: fetal ovary; TE: testis; fTE: fetal testis.

FIG. 14. Sequence of isolated CpG islands are shown which are not available in public databases.

DETAILED DESCRIPTION OF THE INVENTION

We have derived highly polymorphic pluripotent EG cell lines from an interspecific mouse cross, and have shown that these cells lack allele-specific expression and methylation, but acquire these features after in vitro and in vivo differentiation into somatic cell lineages. These results have three important implications. First, these EG cell lines represent the first in vitro model system in which genomic imprinting can be followed dynamically and the two alleles can be distinguished. This system significantly enhances the identification and characterization of trans and cis-acting elements that modify imprinting, and it also confers the advantages of extending such investigations into an in vivo setting.

Figure 8:
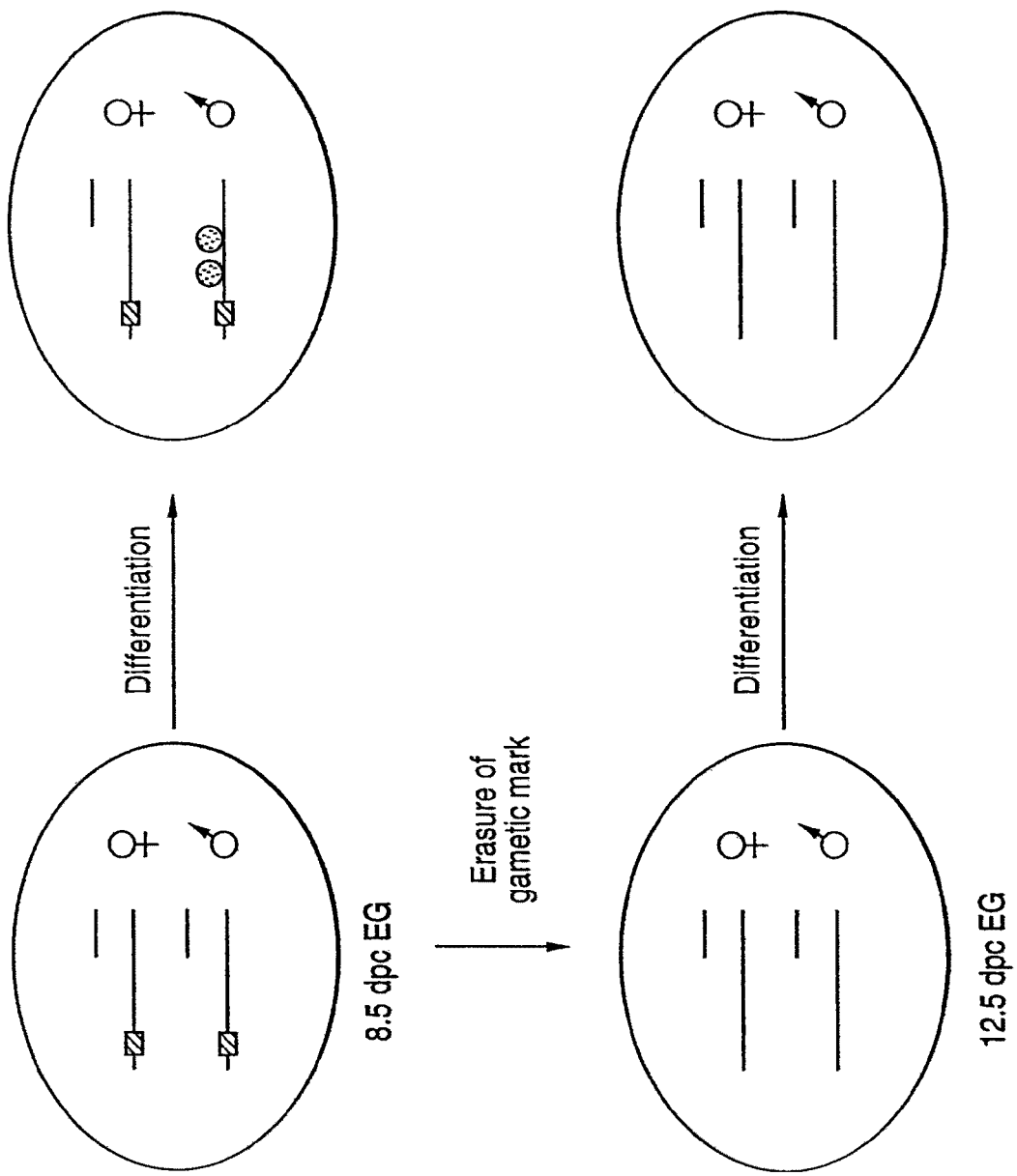
FIG. 8. Model of genomic imprinting in EG cells. For some imprinted genes, EG cells derived from e8.5 embryos retain a gametic memory of the parental origin of the chromosome (colored boxes), although allele-specific silencing and methylation (black dots) are lost. On differentiation into somatic cells, the EG cells re-establish allele-specific silencing and methylation. For EG cells derived from older embryos, this gametic memory has been erased, so that there is no change in biallelic expression (green arrows) or DNA methylation on differentiation into somatic cells.

Second, these results demonstrate that gametic allele memory and allele-specific methylation are separable mechanisms. Our data suggest a model in which undifferentiated EG cells obtained from e8.5 embryos retain a memory of their own parental origin even in the absence of allele-specific silencing and methylation (FIG. 8). On differentiation into somatic cell lineages, this gametic memory becomes manifest (FIG. 8), as imprinted genes acquired allele-specific expression and methylation. In EG cells derived from later stage embryos, this gametic memory is lost (the PGCs from which the EG cells are derived would eventually become reprogrammed according to their own gender), and thus late stage EG cells or PGCs are unable to undergo allele-specific silencing and methylation on differentiation (18). Even in our early stage EG cells, this gametic memory was not preserved for all imprinted genes, as Igf2r was unable to attain imprinting after differentiation. This idea is also consistent with the observation that pre-implantation embryos may not show monoallelic expression of all imprinted genes (24).

This model also has important implications for understanding loss of imprinting (LOI) in cancer (2). We have found that the normal pattern of allele-specific methylation can be restored to at least some tumor cells with loss-of-imprinting (LOI), suggesting that some gametic memory is retained in these cells (25). Similarly, Mitsuya et al. have found that human chromosomes introduced into mouse hybrids by microcell-mediated transfer can lose allele-specific expression but reacquire it after the cells are treated with differentiating agents (26). These observations are consistent with our proposal that a gametic memory is distinct from allele-specific expression and methylation at known DMRs, as we propose here. While the molecular basis of this gametic memory is unknown, candidate mechanisms could include histone acetylation, special chromatin structures, or DNA methylation elsewhere along the chromosome.

Third, since early EG cells did not for the most part lose a gametic imprinting mark, despite biallelic expression in those cells prior to differentiation, we hypothesized that differentiated cell lineages derived from early human EG cells would also show comparatively normal imprinting. This hypothesis was contrary to predictions (19) based on studies of late mouse EG cells or PGCs (18). Our examination of differentiated human EG-derived cells demonstrated normal imprinting at the level of both gene expression and DNA methylation. Thus, genomic imprinting is unlikely to be a barrier to human embryonic stem cell transplantation.

We have also identified methylated CpG islands present in normal tissues (termed MCI). There have been systematic efforts to identify unique CpG islands differentially methylated in tumors (46-48) but no such successful efforts have been described for normally methylated CpG islands. While such sequences may have been suspected, this study represents their first systematic identification in normal tissues, and as such represents a first step toward defining a "methylome", i.e. the distribution of methylation patterns layered on the distribution of genes in the genome.

MCI sequences appear to fall within distinct biological subgroups. We divided the MCI sequences into four categories, based on their copy number and methylation pattern. The first group, MCI-R, is clearly the most abundant, and comprises high copy number sequences such as the SVA element, and the intergenic and internal spacer sequences of ribosomal genes. Methylation of one of these sequences, the rDNA nontranscribed spacer, was previously found after genomic purification from a methyl-CpG binding protein column (51), and one wonders whether the large number of these sequences obscured the identification of unique MCI's. The methylation of high copy number MCI sequences is not surprising, as it is consistent with the hypothesis of that CpG methylation arose as a host defense mechanism (63). This is particularly true of the SVA element, which is a high copy number retroposon.

Of greater interest in this study are the unique CpG islands methylated in normal tissues. There has been great interest in CpG island sequences because of their presumed function in regulation of expression of housekeeping genes (40), their potential involvement in silencing genes in tumors (44,45), and their role in providing a parental origin-specific mark to imprinted genes (42). Our prediction that 1-2% of CpG islands are methylated in normal tissues will likely alter our perspective on CpG islands in general. An important direction of future effort will be to add to the number of known methylated CpG islands. There are several alternative approaches for generating additional second libraries from the Mse I library, although the simplest approach for identifying additional MCIs may be high throughput sequencing of the Mse I library itself. We estimate that the Mse I library contains approximately 77% of the MCI sequences, and we believe that all of the CpG islands within the Mse I library represent such sequences.

We were surprised by the large number of unique methylated CpG islands we were able to identify using a restriction endonuclease-based cloning strategy that eliminated most of the MCI-R sequences from the library. The two largest classes of these unique methylated CpG islands, MCI-S and MCI-D, appear to have different properties, suggesting that they may serve distinct potential functional roles. Specifically, the MCI-S sequences were localized to high isochore regions near the ends of chromosomes, and the MCI-D sequences generally showed a more centromeric localization within low isochore regions. It is remarkable that the MCI-S, which are ubiquitously methylated, even in sperm, retain their high CpG content, which also suggests that they may serve an important role. That role, however, would not appear to be gene silencing, since most of the MCI-S were within the body of transcriptionally active genes.

The MCI-D sequences are particularly interesting for further study, because of their apparent differential methylation in the germline. In particular, these sequences may mark imprinted gene regions, as at least two of these sequences in the Eag I library were found within imprinted genes, namely IGF2R and HYMAI. Furthermore, most imprinted genes appear to lie within low isochore regions (PLAGL1, IGF2R, PEG1 MEST, SNRPN, PEGS, GNAS, unpublished data), like the MCI-D sequences. An intriguing possibility is that a subset of low isochore domains, marked with MCI-D sequences, harbor such genes.

Also surprisingly, most of these unique sequences were not tumor-specific (MCI-T) but were also methylated in normal tissues. We suspect that the MCI-T may represent a comparatively small fraction of the total number of unique methylated CpG islands. One possibility that will be the subject of further study is that the MCI-T may include sequences that are variably methylated in the population, such as MCI-T/2-d10. This is an intriguing idea because it suggests that the methylome might contribute to polymorphic variation in the population, which is consistent with the idea that methylation mutations may be more common in outbred populations than in laboratory strains (64).

Imprinting as used herein is the preferential expression of a specific parental allele, maternal or paternal. Typically it is associated with the modification of a specific parental allele, such as by DNA methylation, histone acetylation, histone phosphorylation, or histone methylation. Imprinting can be assessed using any method known in the art for determining expression from a particular allele. Such techniques include without limitation pyrosequencing for high throughput assaying, MALDI-TOF mass spectrometry, allele specific oligonucleotide DNA microarray, Hot-stop PCR (Uejima et al., Nat. Genet. 2000, 4:375-6), SSCP (single stranded conformational polymorphism assay), QS (quantitative sequencing), SNuPE (Single nucleotide primer extension), and allele-specific ligation assay. Unimprinted genes are typically expressed in an approximately equal biallelic fashion, whereas imprinted genes display preferential expression of a specific parental allele. Approximately equal biallelic expression may be as disparate as about 40%:60%, preferably from about 45%:55%, more preferably from about 47.5%:52.5%. Expression differences greater than this, such as 30%: 70%, 20%:80%, 10%: 90%, and 5%:95% are considered preferential expression of a specific parental allele.

Methylated CpG islands which are repetitive (MCI-R) can be used as portable sites of genetic recombination, as indications of past chromosomal rearrangements or as indications of past insertion element-created mutations. Most CpG dinucleotides within a methylated CpG island contain a methylated 5-position on the pyrimidine ring of cytosine. The methylation level within a CpG island is believed to be quite high, with at least 75%, 80%, 90%, 95%, or even 98% of the cytosine residues being methylated. Functionally, the methylated CpG islands survive the isolation procedure which involves restriction with a restriction endonuclease which cleaves at unmethylated CpG dinucleotides. Methylated CpG islands which are differentially methylated among maternal-derived and paternal-derived tissues (MCI-D) can be used as markers of the locations of imprinted genes. Typically, MCI-D are located within imprinted genes are adjacent to imprinted genes. Adjacency is within $2 \times 10^6$ base pairs, preferably within $1 \times 10^6$ base pairs, more preferably within $0.5 \times 10^6$ base pairs. MCI-S and MCI-T, methylated CpG islands which are expressed similarly in uniparental tissues and those which are differentially expressed in tumors and normal tissues, can be used as methylation polymorphism markers in the population. Thus they can be used as sequence polymorphisms, forensically, diagnostically, and predictively as risk factors for disease traits.

Embryonic germ cells are useful as a dynamic model system for studying imprinting. The ability to induce imprinting permits the analysis of factors which stimulate or inhibit the process. The factors can be endogenous or exogenously applied. It is desirable to use parental animals which are of the same species yet which are sufficiently genetically divergent such that at least 50% of genes in resulting offspring have at least one sequence difference between alleles of said genes. More preferably at least 60%, 70%, 75%, 80%, 90%, or 95% of the maternal and paternal genes in the offspring will be detectably different. This greatly facilitates analysis of imprinting by rendering most genes amenable to analysis of differential allelic expression. Suitable mammals which can be used include without limitation mice, rats, hamsters, guinea pigs, rabbits, goats, cows, sheep, pigs, horses, dogs, and cats.

Embryos are desirably removed from the pregnant female mammal at a stage of embryonic development between when 2-3 somites become visualizable and when gonads are recognizable. In mice, this stage is between day 7 and 10 post conception. Obtaining embryos at such an early stage is believed to be beneficial in obtaining cells which have many genes which are not yet imprinted. Embryos are dissected and cultured, preferably on feeder cell layers. The posterior third of the embryo can be dissected and used to form dissociated cells. Alternatively, the genital ridge of the embryo is dissected out and used to form dissociated cells. Still another alternative method dissects out gonads of the embryo to form dissociated cells.

Once cell lines have been obtained they can be used for various assays and tests. The cell lines express one or more imprintable genes in an approximately equal biparental fashion, form cells which express one or more imprintable genes in an approximately equal biparental manner, and differentiate to form cells which express said one or more imprintable genes in a preferentially uniparental fashion. The assays for imprinting can be done in vitro or in vivo as is desired by the practitioner. In one assay, the mammalian embryonic germ cells are grown in suspension culture under conditions in which the embryonic germ cells differentiate. The differentiated cells may or may not form an embryoid body. Upon differentiation expression of one or more imprintable genes changes from approximately equal biallelic to preferentially uniparental. Differentiation can be induced by growth on plastic in the absence of feeder cells, by growth in the presence of dimethylsulfoxide, by growth in the presence of retinoic acid, by growth on a methyl-cellulose containing medium, or any other method known in the art. According to one particularly preferred method the germ cells contain a selectable marker under transcriptional control of a tissue-specific promoter, and the germ cells are subjected to selection conditions to select germ cells which have differentiated into a lineage which activates the tissue-specific promoter.

A number of techniques are available for inducing and observing imprinting in vivo using the cell lines of the present invention. The mammalian embryonic germ cells can be injected into a nude mouse in which it will form a teratocarcinoma. One or more imprintable genes change from approximately equal biallelic to preferentially uniparental expression upon formation of the teratocarcinoma. Another way to achieve imprinting in an in vivo model is to inject a mammalian embryonic germ cell into a blastocyst of a mammal. The blastocyst is then implanted into a pseudopregnant mammal so that the blastocyst develops into a chimeric mammal, i.e., its somatic cells are not genetically identical. Expression of one or more imprintable genes in somatic cells derived from the embryonic germ cell becomes preferentially uniparental. The germ cells used for formation of teratocarcinomas or chimeric blastocysts can optionally be transfected with a vector which expresses a detectable marker protein. This makes distinguishing among the cells of the mammal a simpler exercise.

Imprinting can be assayed directly in any of the models of the invention by detecting parental allele specific expression. Alternatively, a surrogate for such expression can be used such as cytosine methylation, histone acetylation, histone phosphorylation, histone methylation. Methods for detecting such modifications are known in the art.

Test substances used to contact with the cell lines or chimeric mammals of the present invention can be any natural, synthetic, or semisynthetic substance, whether a pure compound or a mixture of compounds. The test substances can be compounds or drugs which are known to have one mor more biological effects, or substances which are not known to have any biological or physiological effects. If the test animal contains a teratoma, one can identify a test substance as a candidate drug if it inhibits the growth of the teratoma or causes regression of the teratoma. Techniques for assessing the growth of a teratoma or regression of a teratoma are well known in the art.

Figure 9:
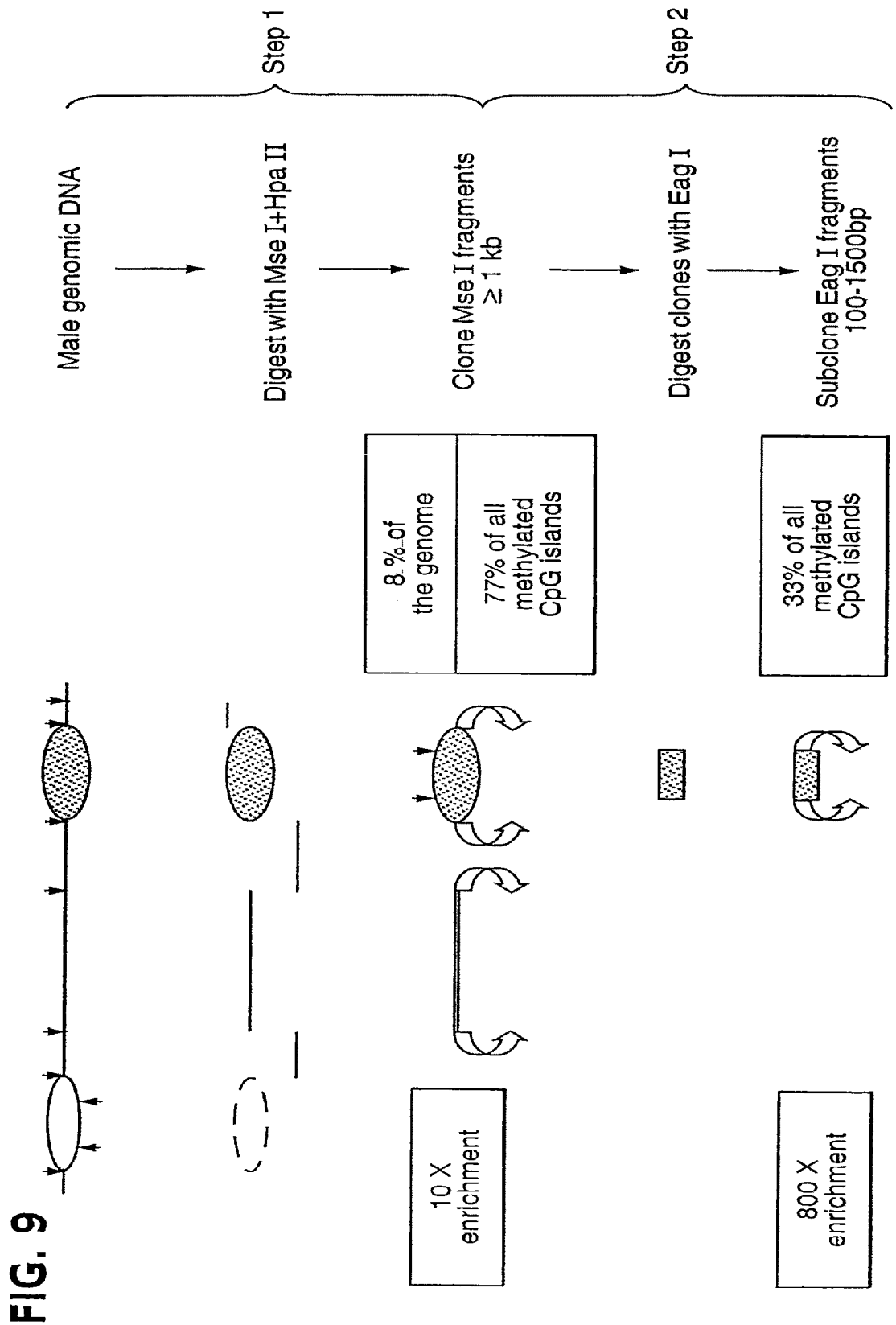
FIG. 9. Overall strategy for cloning methylated CpG islands. Male genomic DNA from a Wilms tumor was digested with Hpa II and Mse I, fragments ≧1 kb in size were subcloned into a modified pGEM-4Z vector and transformed into XL2-Blue MRF', resulting in an expected 10× enrichment for methylated CpG islands, that was confirmed by Southern hybridization. Library DNA was then digested with Eag I, and fragments between 100 by and 1500 by were subcloned into pBC and transformed into XL 1-Blue MRF1 resulting in an expected 800× enrichment for methylated CpG islands. Black ellipse depicts a methylated CpG island, clear ellipse depicts an unmethylated CpG island. In step 1, thick arrowheads above the line depict Mse I sites (TTAA) and below the line depict unmethylated Hpa II sites (CCGG). In step 2, thick arrowheads depict Eag I sites (CGGCCG). Enrichment estimates were based on an in silico analysis of frequencies of Mse I, Hpa II, and other CpG-rich restriction endonucleases including Eag I, in CpG islands vs. non CpG island DNA: Mse I fragments ≧1 kb in size included 77% of CpG islands and 8% of non-CpG island DNA (0.77/0.08=10× enrichment). In the second step, 43% of the set of CpG islands would have been cloned by Eag I and thus for a two-step cloning using Mse I and Eag I, the fraction of methylated CpG islands expected is 0.43×0.77=0.33. The expected 800× enrichment is derived from the expected fraction of CpG islands after an Eag I digest (0.028) divided by the initial estimated fraction of methylated CpG islands based on the only known normally methylated autosomal CpG islands, i.e. those associated with imprinted genes.

Methylated CpG islands can be isolated using a scheme as outlined in FIG. 9. Any restriction endonucleases can be used which have the desired properties specified. The properties are based on the frequency of cleavage sites, and the preference of the cleavage sites for being in G/C or A/T rich regions. The CpG islands can be isolated from genomic DNA from males or females, from tumor or normal cells. Any type of tumor or normal tissue can be used as a source of cells. Once such methylated CpG islands are isolated, they can be used for a number of different techniques. In one, they are tested to identify sequences which are differentially methylated between maternal and paternal chromosomes. In another technique they are tested to identify sequences which are differentially methylated between hydatidiform moles and teratomas. In another technique they are mapped to a genomic region. The CpG islands can be used to identify an imprinted gene adjacent to the methylated CpG island, as methylated CpG islands are markers for such genes. If a CpG island is found to map to the same region as a disease which is preferentially transmitted by one parent, an imprinted gene in the region can be identified as a candidate gene involved in transmitting the disease. The CpG islands can be used to screen populations of individuals for methylation. A sequence which is differentially methylated between individuals is a methylation polymorphism which can be used to identify individuals.

Practice of the disclosed method for isolating CpG islands creates libraries which are enriched at least 100-fold, at least 250-fold, at least 500-fold, or at least 750-fold in methylated CpG islands relative to total genomic DNA. Preferably each library of fragments will contain at least 25, at least 50, or at least 75 distinct members.

The particular CpG islands which have been found using the method of the present invention are disclosed in Table 2. These particular CpG islands can be used to assess risk of developing cancer. Perturbed methylation of CpG islands relative to sequences in a control group of healthy individuals suggests that the individual being tested are at increased risk of developing cancer. Any number of CpG islands can be tested in such a method, but preferably at least 2, 5, 10, or 15 such islands will be tested. An increased risk of developing cancer is determined if at least 1 of 2, 3 of 5, 6 of 10, or 8 of 15 of the CpG islands have perturbed methylation status relative to control group. Similarly aberrant methylation of CpG islands can be determined where the methylation in a suspect tissue sample of a patient is compared to the methylation in an ostensibly healthy tissue sample of the patient.

CpG islands can be used to identify genes which are within about 2 million base pairs of a CpG island identified in Table 2 in the human genome. The genes are preferably within 1 million base pairs, and more preferably within 500,000 base pairs. If the gene is preferentially uniparentally expressed, then it is identified as an imprinted gene.

EXAMPLES

Example 1

Figure 1:
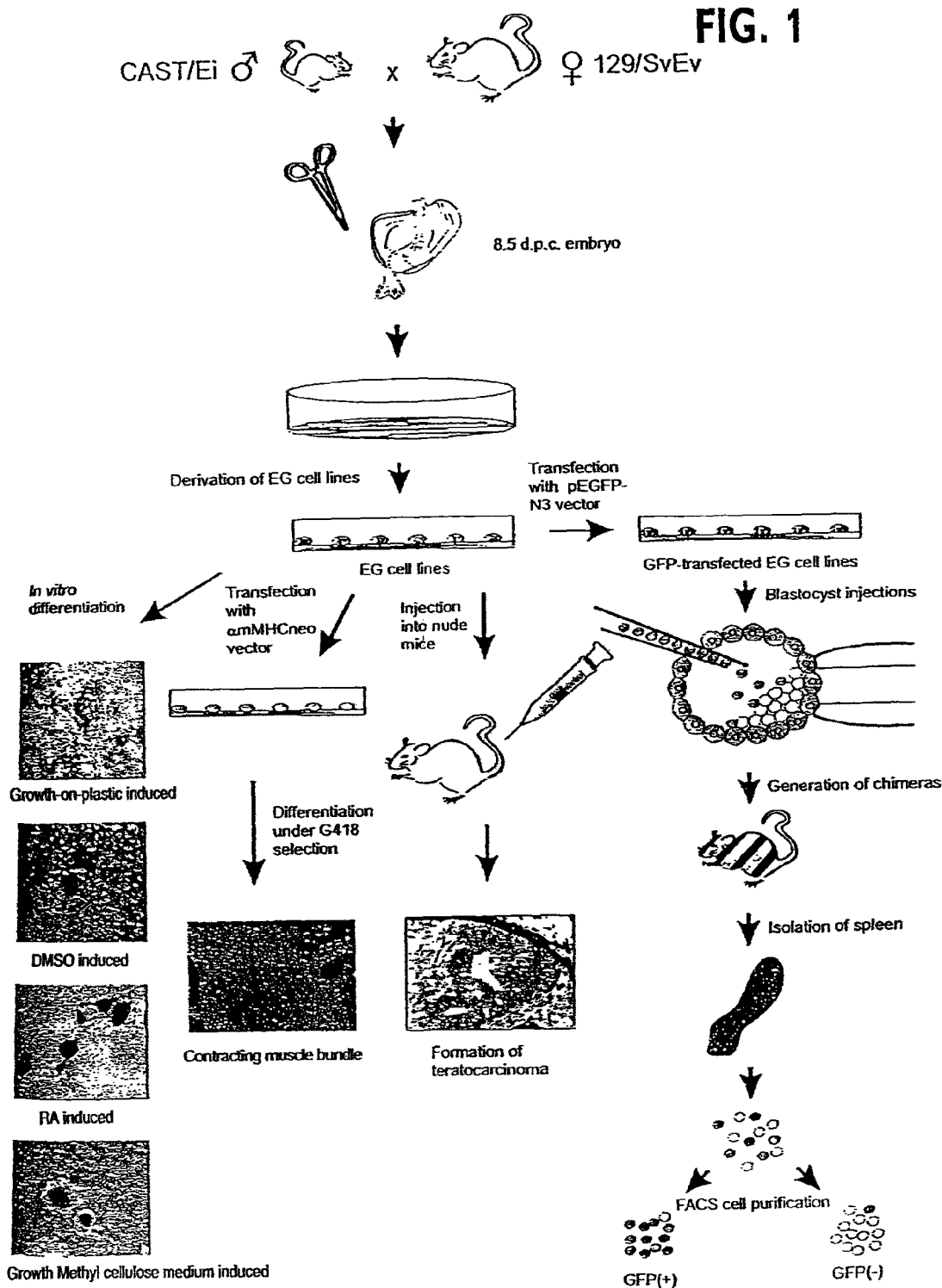
FIG. 1. Experimental design. E8.5 F1 (129/SvEv×CAST/Ei) embryos were dissected near the base of the allantois to initiate PGC cultures from which EG cell lines were established. EG cell lines were differentiated in vitro by either of several methods, injected subcutaneously into athymic nude mice to form teratocarcinoma, or transfected with a GFP vector and injected into the blastocysts of C57BL/6 to generate chimeric mice, from which differentiated cells were purified by FACS.

We used 129/SvEv mice as the mothers in the cross. We chose CAST/Ei (Mus musculus castaneus) mice, separated from 129/SvEv by 5 million years in evolution, as the father in the cross, providing an average of one polymorphic marker per 400 by of transcribed sequence. The experimental strategy is summarized in FIG. 1, and it allows differentiation in vitro by a variety of mechanisms, including targeted differentiation using a selectable construct, and differentiation in vivo using chimeric mice.

Figure 2A:
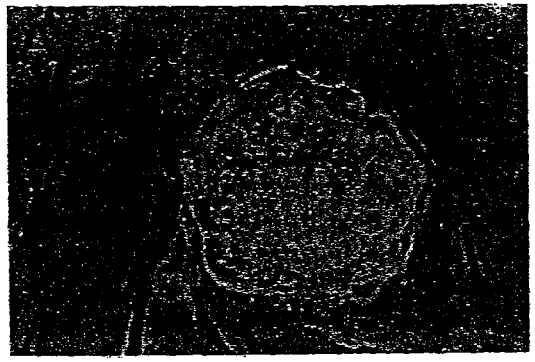
FIG. 2A-2F. Characterization of mouse interspecific EG cell lines.
Figure 2B:
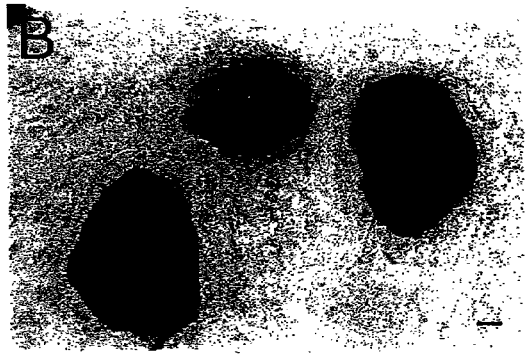
Figure 2C:

Forty EG cell lines were derived from primordial germ cells (PGCs) of 8.5 day embryos (4), as determined by colony morphology and positive alkaline phosphatase staining (FIG. 2A, B), and four of these lines were characterized in detail (termed SJEG-1, 2, 7, and 15). These EG cell lines formed embryoid bodies after in vitro differentiation (FIG. 2C, D), teratocarcinomas in nude mice (FIG. 2E, F), and generated chimeric mice when injected into the blastocyst of C57BL/6 mice (5). One male line was also used for subsequent germ-line transmission (5). Most of the imprinting studies were done on lines SJEG-1, 2, and 7.

Example 2

Partial establishment of imprinting in vitro. In order to distinguish the two alleles of imprinted genes in these EG cell lines, we identified transcribed polymorphisms distinguishing 129/SvEv and CAST/Ei in 5 imprinted genes, Kvlqt1, Snrpn, Igf2, H19, and Igf2r, as well as the nonimprinted gene L23mrp as a negative control. For each gene, an assay for allele-specific expression was then developed, as described in Table 1.

TABLE 1

Transcribed polymorphisms and assay methods for allele-specific gene expression of EG cells derived from mouse interspecific cross.

| | Polymorphism | | Assay | |
|---|---|---|---|---|
| Gene | CAST/Ei[1] | 129/SvEv | Position[2] | Method |
| Kvlqt1 | TCCCTGC | TCCATGC | 1823 | SSCP[3] |
| Igf2 | GCAATTC | GCAGTTC | 111 | SSCP[3] |
| H19 | CTTGGAG | CTTTGAG | 1593 | QS[4] |
| Snrpn | CTATAAT | CTACAAT | 915 | SNuPE[5] |
| IgOr | ATCGATG | ATCAATG | 1549 | SNuPE[5] |
| L23mrp | ACCCGAG | ACCTGAG | 407 | SSCP[3] |

[1]Polymorphisms were identified by direct sequencing of CAST/Ei genomic DNA. 129/SvEv sequence was identical to known *Mus musculus musculus* sequence in GenBank, except that Kvlqt1 sequence was unavailable and done here.
[2]From first nucleotide of cDNA
[3]Single strand conformation polymorphism (27).
[4]Quantitative sequencing (28).
[5]Single nucleotide primer extension (29).

Figure 3A:
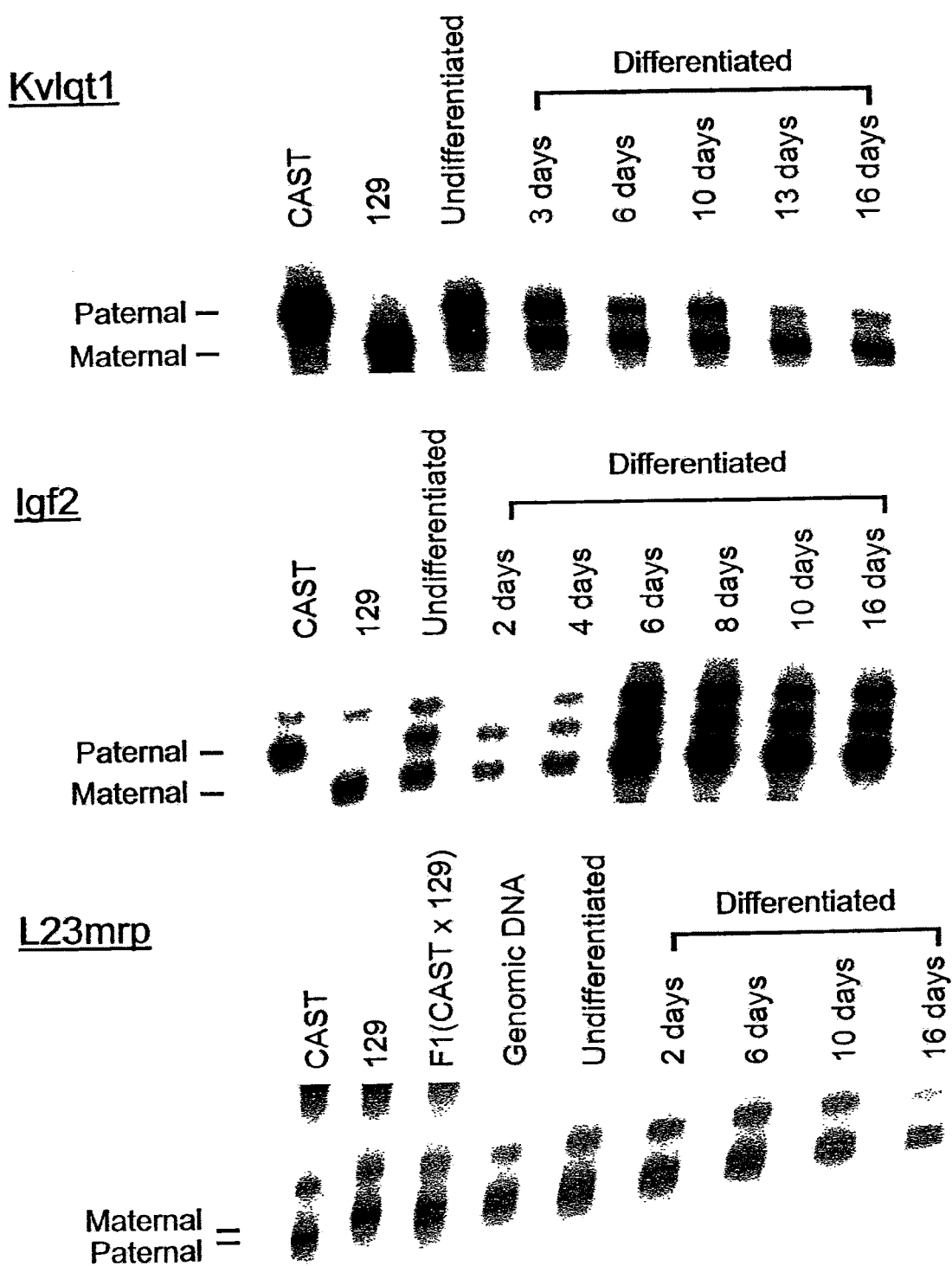
FIGS. 3A and 3B. Partial imprinting establishment of EG cells induced by spontaneous in vitro differentiation on plastic. RNA and DNA were prepared at varying times during differentiation.
Figure 3B:
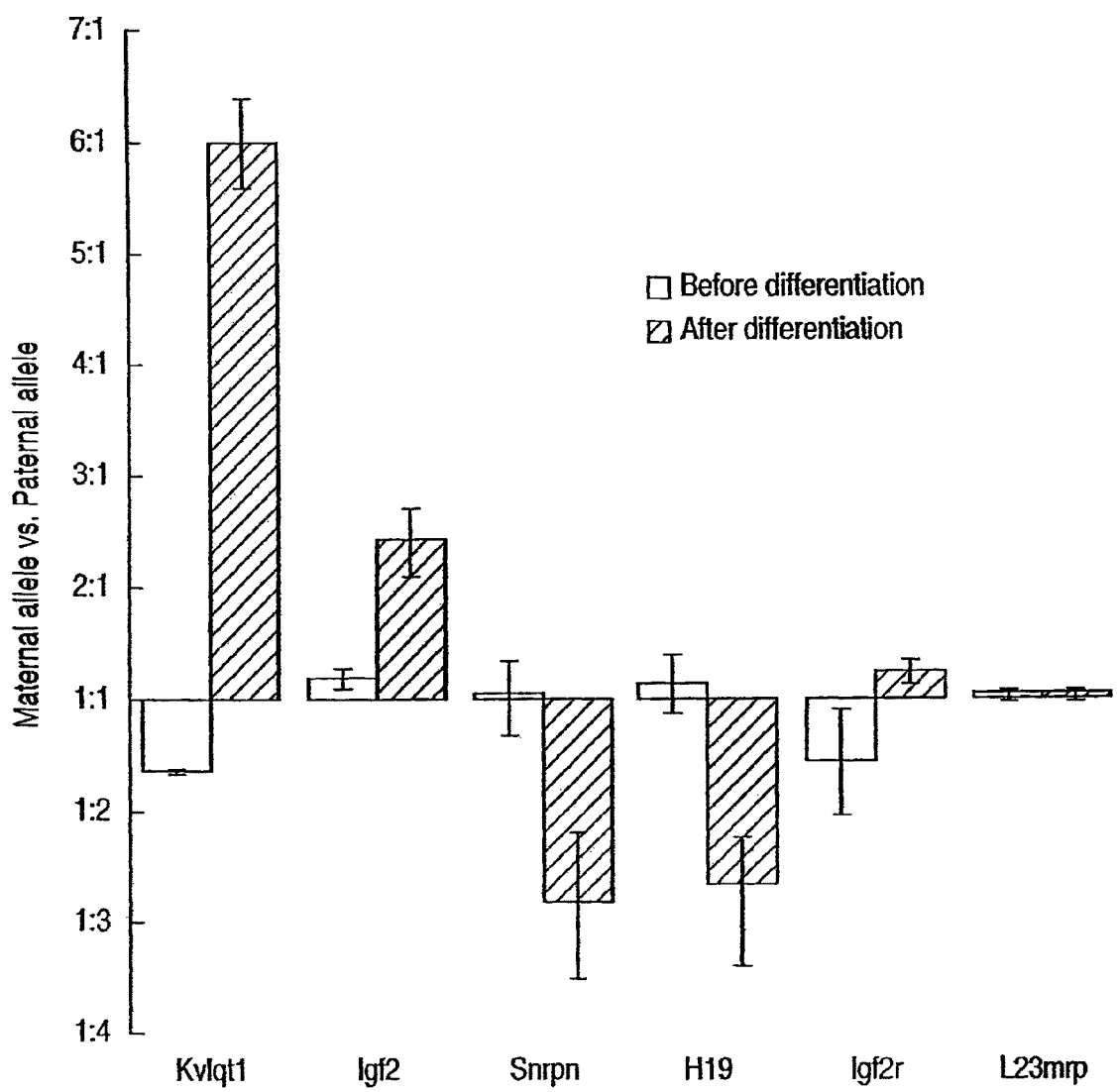

Kvlqt1 shows preferential expression of the maternal allele throughout development in this strain background (6). Prior to somatic differentiation of EG cells in vitro, Kvlqt1 showed approximately equal expression of the two alleles (FIG. 3A). After differentiation by replating on plastic in the absence of a feeder cell layer, Kvlqt1 showed clear preferential expression of the maternal allele, which increased to a 6:1 ratio by day 16 (FIG. 3A), and this result was seen in all three cell lines tested (FIG. 3B). Like Kvlqt1, Igf2 showed approximately equal biallelic expression of the two parental alleles prior to differentiation (FIG. 3A). However, after EG cell differentiation, unlike Kvlqt1, which showed preferential allele-specific expression in the same parental direction as F1 offspring, Igf2 showed allele-specific expression but in opposite direction to the F1 offspring. Thus, differentiated EG cells showed preferential expression of the maternal allele of Igf2 (FIG. 3A). While this was a surprising observation, it was consistent among different cell lines (FIG. 3B). The expression of the maternal allele of IGF2 is also consistent with an observation of allele reversal in embryonic stem (ES) cells (7). This may be a property of pluripotent embryonic stem cells (although note that in contrast to EG cells, imprinting shows little or no change in ES cells (7)).

HI9 normally shows reciprocal allele-specific expression to IGF2, perhaps due to competition for a shared enhancer (8). Consistent with this pattern, H19 exhibited approximately equal expression of the two parental alleles before differentiation, and preferential expression of the paternal allele after differentiation, changing from a ratio of 1:1 to 3:1 after differentiation (FIG. 3B). Snrpn, which is preferentially expressed from the paternal allele in somatic cells (9), also showed equal biallelic expression in undifferentiated EG cells (FIG. 3B). After differentiation, Snrpn showed preferential expression of the normally expressed paternal allele, at a ratio of 3:1 (FIG. 3B). In contrast, Igf2r showed approximately equal biallelic expression both before and after differentiation, suggesting that for this gene, the gametic mark had been completely erased in EG cells (FIG. 3B).

As a negative control, we analyzed the nonimprinted gene L23mrp, which is just outside of a contiguous imprinted gene domain that includes Igf2, 1119, and Kvlqt1 (10). In contrast to Igf2, 1119, and Kvlqt1, L23mrp showed equal biallelic expression of the two parental alleles both before and after in vitro differentiation (FIG. 3A,B). Furthermore, the ratio of allele-specific expression of the imprinted genes after differentiation differed significantly from that of L23mrp ($p<0.01$, two-tailed t-test). In summary, in vitro differentiation partially restored imprinting to EG cells.

Example 3

Figure 4A:
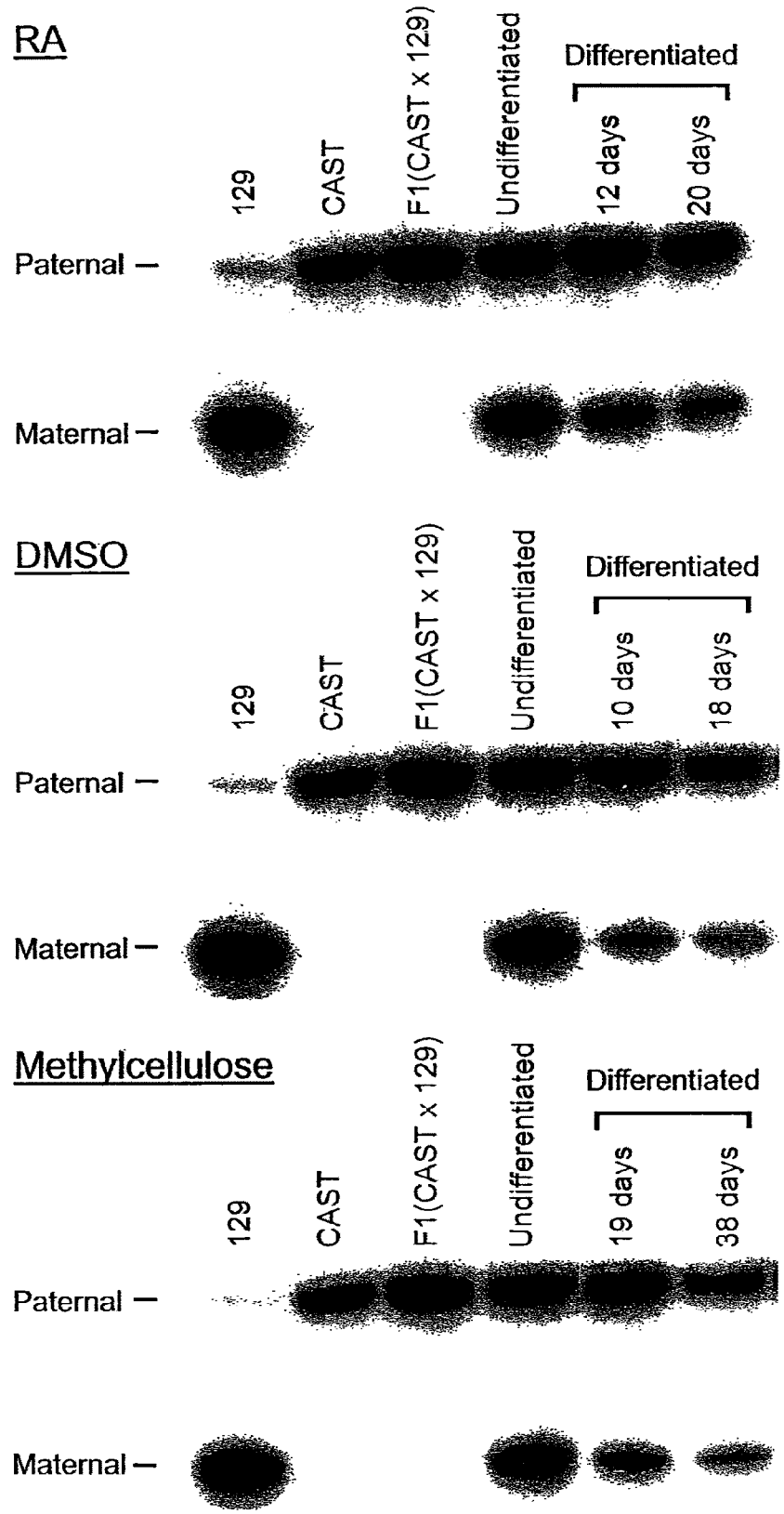

Imprinting was independent of differentiation method. In order to determine whether allele-specific expression in EG cells was caused by differentiation in vitro, or by the specific treatment used to differentiate EG cells, we repeated these experiments by differentiating the cells in 3 other ways (4): differentiation in methylcellulose medium; treatment with retinoic acid; and treatment with dimethyl sulfoxide. In all cases, the results were identical to those seen on spontaneous differentiation on plastic in the absence of a feeder cell layer. For example, Snrpn showed equal biallelic expression of the two parental alleles prior to differentiation, and preferential expression of the paternal allele after differentiation in all cases, but with slight variation in the final ratio of parental alleles (FIG. 4A).

Figure 2D:
Figure 2E:
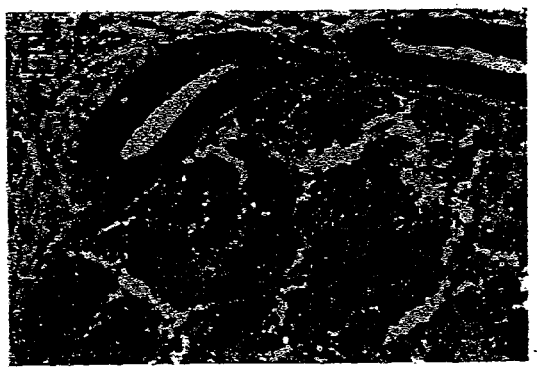
Figure 2F:
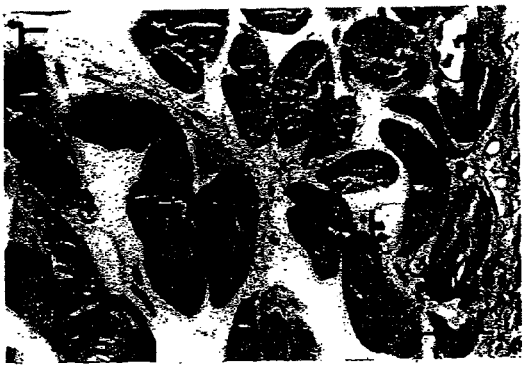

Embryoid bodies that result from in vitro differentiation of EG cells show considerable cellular heterogeneity, and not all of the cells are differentiated. In order to determine whether allele-specific expression would arise during differentiation down a specific cell lineage pathway, we used a genetic selection strategy to obtain lineage-specific EG cell differentiation. We transfected EG cells with a vector containing the neo selectable marker gene under the control of a mouse a-cardiac myosin heavy chain gene promoter (11). Clones of transfected EG cells remained undifferentiated, and showed equal biallelic expression of Kvlqt1, Igf2, H19, Snrpn, Igf2r and L23mrp (FIG. 4B and data not shown). Differentiation of transfected EG cells under G418 selection produced a network of rhythmically contracting myocyte bundles in culture (11) (FIG. 2D). Examination of these cells for allele-specific expression showed preferential allele expression similar to that seen using other differentiation approaches, but with a slightly greater ratio of allele-specific expression. For example, Kvlqt1 achieved a 9:1 ratio of maternal to paternal allele expression after cardiac myocyte-specific differentiation in vitro (FIG. 4B). Thus, establishment of imprinting was due to differentiation itself, and not to the specific methods used to induce it.

Example 4

Figure 5A:
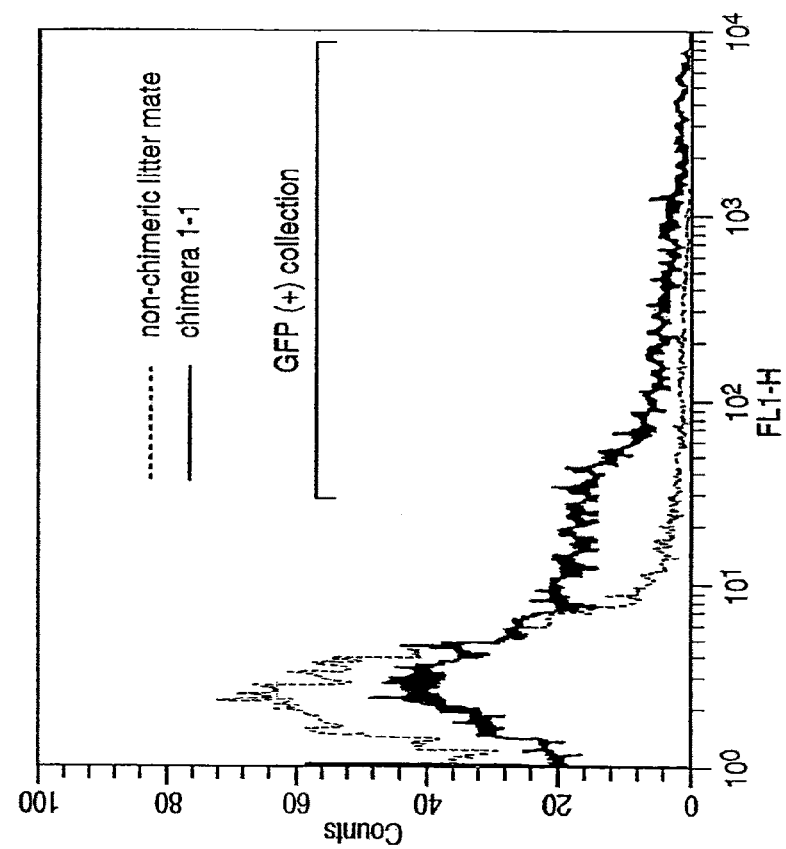
FIG. 5A-5E. Nearly complete imprinting of EG cells after in vivo differentiation.
Figure 5B:
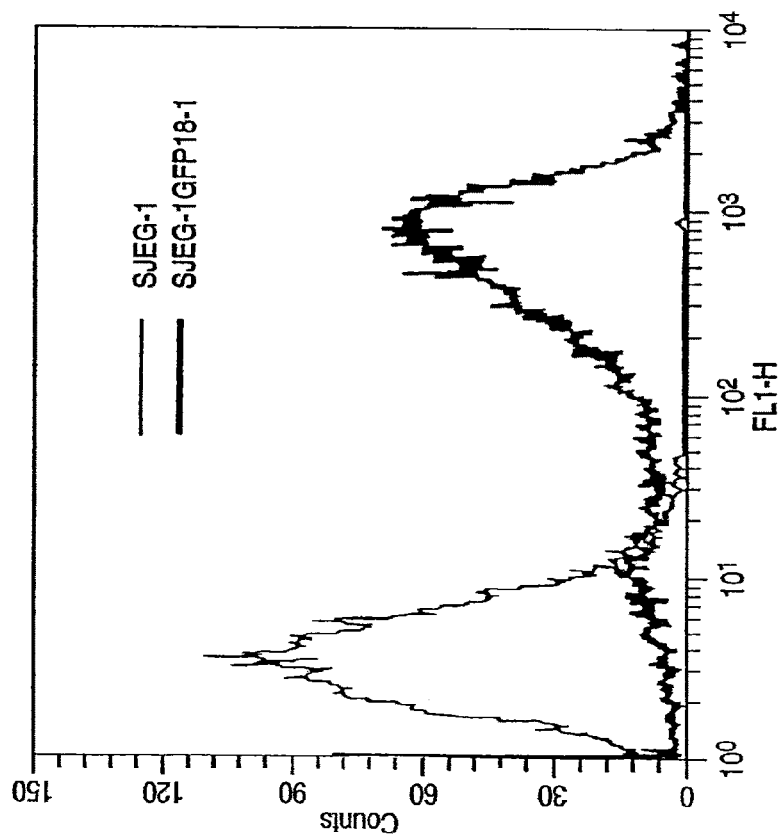

Nearly complete imprinting establishment after differentiation of EG cells in vivo. To verify that the changes in imprinting we observed in vitro also occurred during natural differentiation in vivo, we took advantage of the pluripotency of our EG cell lines to generate mouse chimeras. In order to purify cells derived from these EG cells after in vivo differentiation in chimeric mice, we first transfected EG cells with a vector containing a modified GFP gene under the control of the CMV promoter (5) (FIG. 5A). We then injected the cells into C57BL/6 blastocysts, which were introduced into pseudopregnant mice and allowed to develop to term (5). Spleens were removed from chimeras, and the EG-derived GFP(+) cells were purified by fluorescence-activated cell sorting (FACS) to 99% homogeneity (FIG. 5B). Purity of EG-derived cells isolated from the chimeric mice was confirmed by measuring the allele ratio in genomic DNA for polymorphisms that distinguish the two strains (data not shown).

Figure 5C:
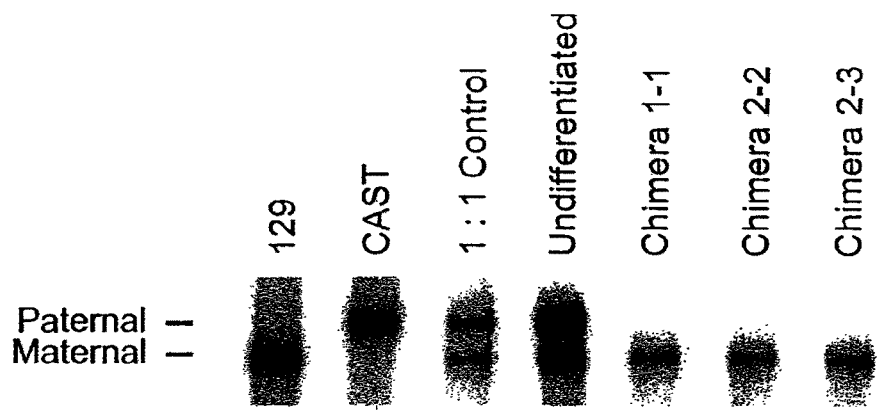
Figure 5D:
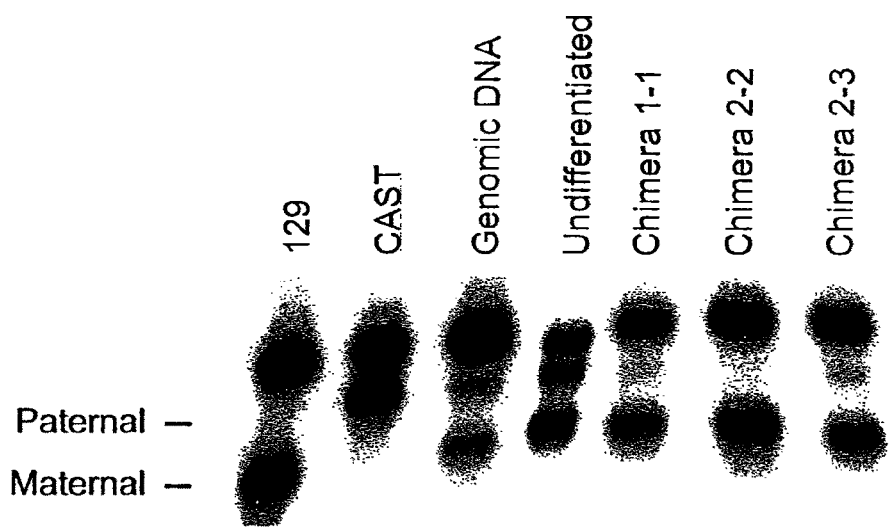
Figure 5E:
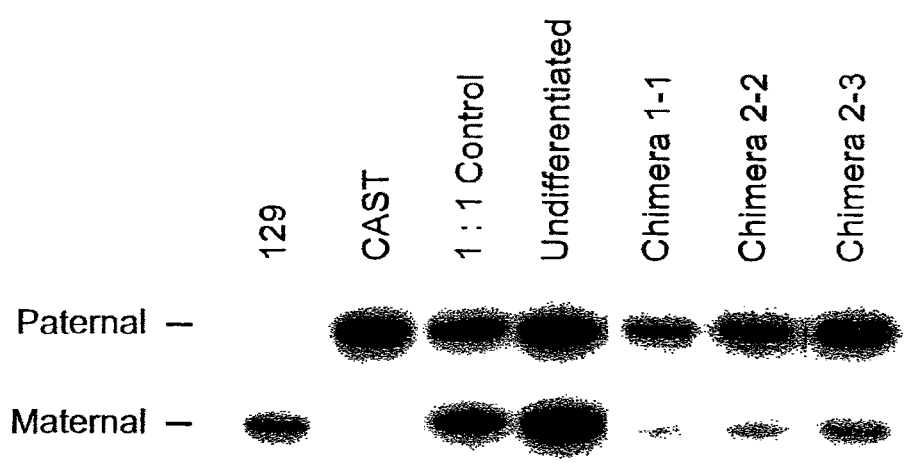

Analysis of imprinting of EG-derived cells isolated after in vivo differentiation in chimeric mice indicated that all of the imprinted genes studied showed the same pattern of allele-specific expression found after in vitro differentiation. However, after in vivo differentiation, the degree of allele-specific expression was nearly complete. Thus, Kvlqt1 showed equal biallelic expression after transfection of the pEGFP-N3 vector and prior to blastocyst injection, and monoallelic expression of the maternal allele after in vivo differentiation in three separate chimeric mice (FIG. 5C). Similarly, Igf2 showed monoallelic expression of the maternal allele in two separate chimeric mice and nearly monoallelic expression (>10:1) in a third (FIG. 5D). H19 also showed monoallelic expression of the paternal allele, the same allele preferentially expressed after in vitro differentiation (data not shown). Finally, Snrpn exhibited predominant expression of the paternal allele (4:1 ratio) after in vivo differentiation. As a control, L23mrp showed equal biallelic expression after in vivo differentiation (data not shown). Thus, in vivo differentiation of EG cells caused nearly complete establishment of imprint-specific expression.

Example 5

Establishment of differential DNA methylation during in vitro differentiation of EG cells. From all of the above experiments, it is clear that these EG cell chromosomes retain some memory of their parental origin, but they do not manifest this memory as allele-specific expression until the cells are differentiated. DNA methylation has been shown previously to play a role in genomic imprinting, because mice deficient in DNA methyltransferase 1 show loss of imprinting (12). In order to determine whether DNA methylation represents the mechanism of the gametic mark, we analyzed the methylation status of two previously well-characterized differentially methylated regions (DMR).

Figure 6B:
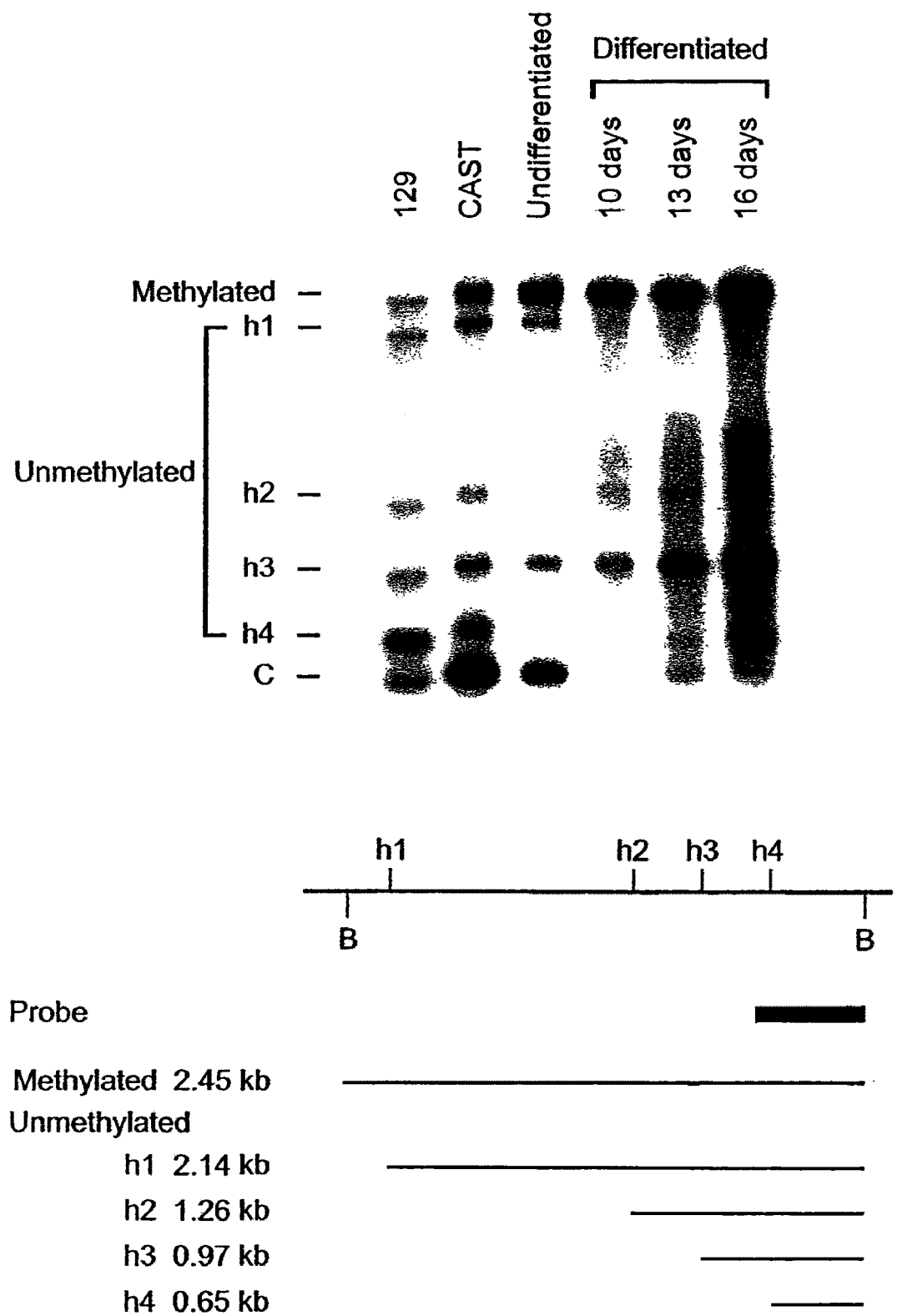

Differential methylation in the H19 gene DMR, located −4 to −2 kb upstream of the transcriptional start site, is established in the gamete and stably maintained during early development (13). Our analysis of undifferentiated EG cells revealed a hypomethylated pattern, at a ratio of 4.3:1 unmethylated to methylated bands (FIG. 6A). This result was consistent with the biallelic pattern of H19 expression in undifferentiated EG cells (FIG. 3B), since methylation of the H19 DMR is associated with allele-specific silencing (14). However, with in vitro differentiation, H19 acquired a typical half-methylated pattern, similar to that seen in the parental and F1 mice, with a 1:1 ratio of unmethylated to methylated bands (FIG. 6A). This change in methylation reflected well the change in expression from approximately biallelic to predominantly monoallelic in these cells after differentiation. To further determine which parental allele of H19 became methylated after in vitro differentiation, we analyzed the allele composition of methylated H19 DMR using a previously described method (13). Our analysis of differentiated EG cells revealed that the half-methylation pattern described above (FIG. 6A) was due to methylation of the non-expressed allele (data not shown). Thus, the methylation was allele-specific and related to silencing of the H19 gene during differentiation.

Igf2 DMR2, within exon 6, is known to be the more closely linked DMR to Igf2 imprinting (15). We analyzed its methylation in EG cells by methods previously described (16). Analysis of undifferentiated EG cells revealed a hypermethylated pattern, at a ratio of 4:1 methylated to unmethylated bands (FIG. 6B), consistent with the biallelic expression of Igf2 in undifferentiated cells (FIG. 3A,B), since the methylation of Igf2 DMR2 is normally associated with the expressed allele (15). With in vitro differentiation, Igf2 acquired a half-methylated pattern, with a 1:1 ratio of methylated to unmethylated bands (FIG. 6B), consistent with the predominantly monoallelic expression of Igf2 after differentiation (FIG. 3A,B). Thus, DNA methylation reflected the pattern of gene expression of both Igf2 and H19, with a nonimprinted pattern of DNA methylation before differentiation, and an imprinted pattern after differentiation.

Example 6

Nearly complete imprinting in differentiated human EG cells. Pluripotent human EG cell cultures have recently been derived (17). The potential therapeutic use of these cells in medicine has received considerable attention, since they can be employed as an unlimited source for a variety of tissues used in human transplantation therapy. However, some recent experiments using late mouse EG cells (e12.5) and PGCs (e14.5-16.5) suggested that genomic imprinting could not be established, and lack of imprinting is associated with developmental abnormalities and embryonic mortality (18). These results have raised widespread public concern over the feasibility of human EG cells for therapeutic use (19).

Figure 7A:
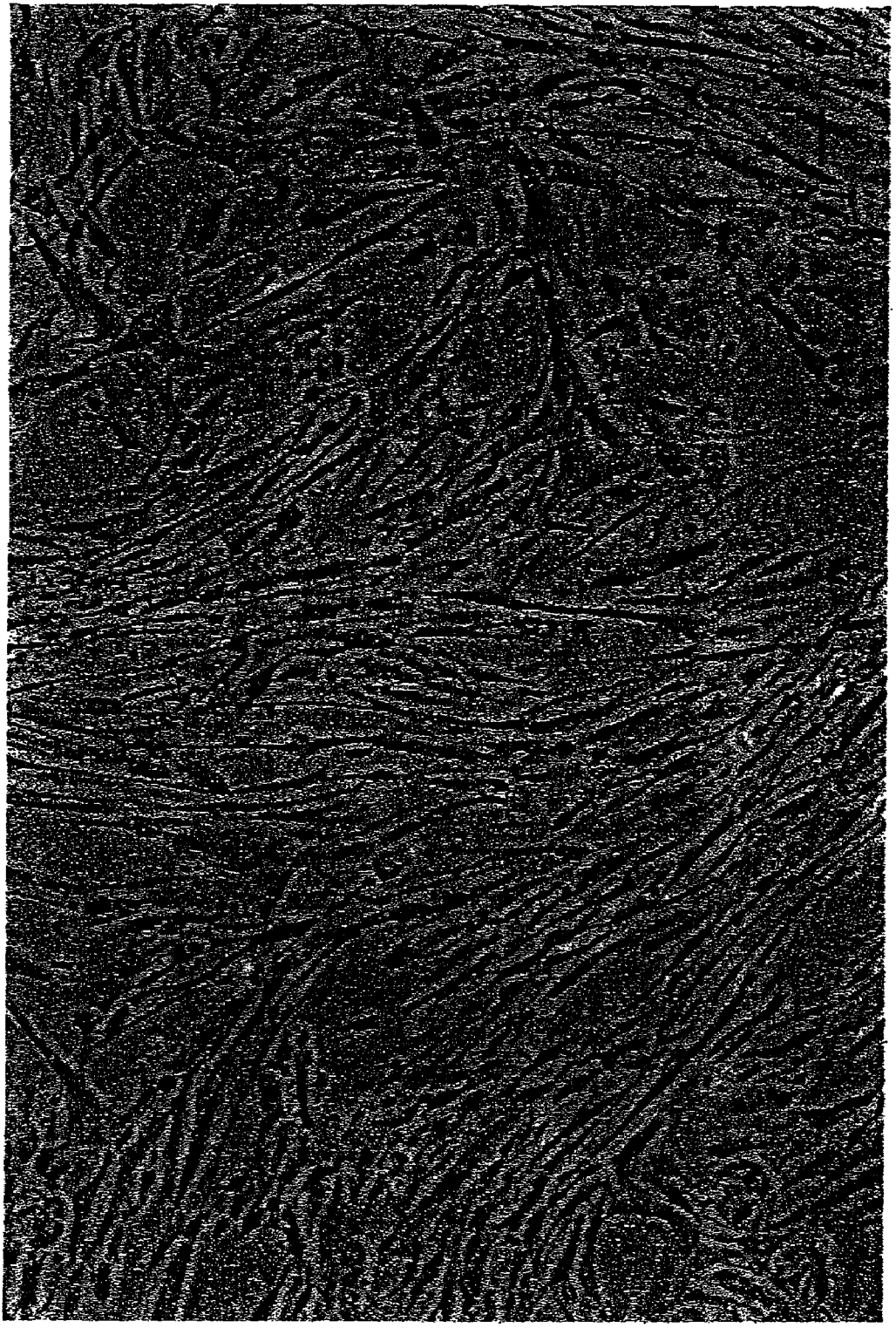
FIG. 7A-7D. Nearly complete imprinting in differentiated human EG cells.
Figure 7B:
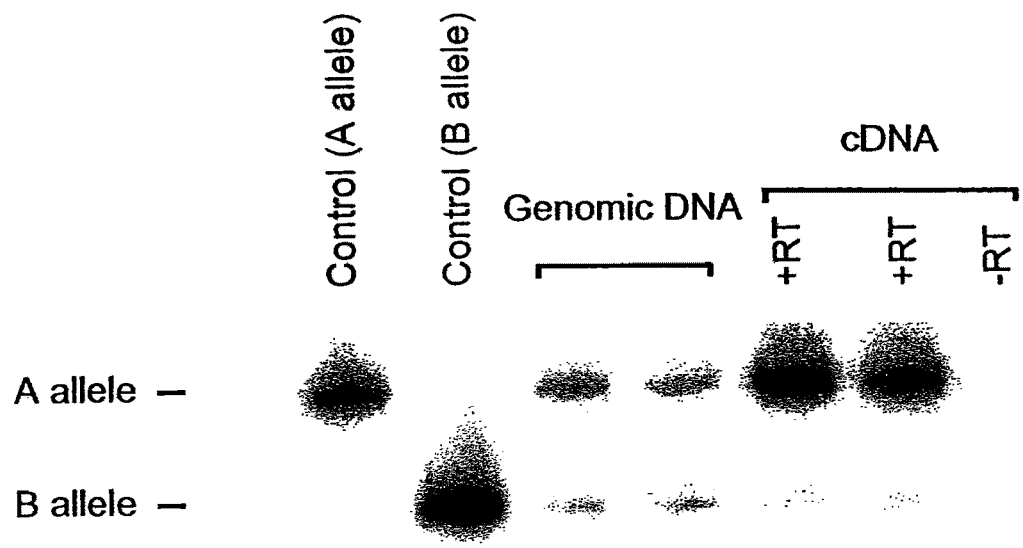
Figure 7C:
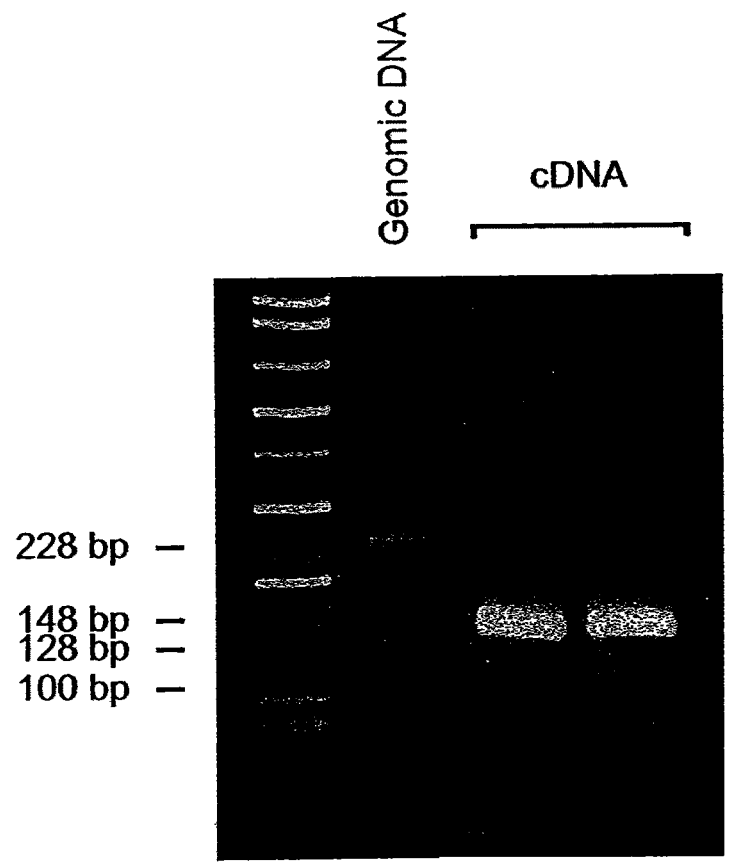

Because of these concerns, we endeavored to determine whether human EG cells can achieve genomic imprinting after differentiation, like mouse EG cells. We examined genomic imprinting in a differentiated monolayer culture of lineage-restricted cell types (20) (FIG. 7A), derived from a human EG culture reported previously (17). IGF2 was examined using an Apa I polymorphism in exon 9 (21). While Apa I digestion revealed two alleles in genomic DNA, analysis of cDNA showed a nearly complete monoallelic expression pattern (FIG. 7B), indicating a nearly complete establishment of imprinting of IGF2 gene after in vitro differentiation of a human EG culture. H19 was then examined using an Alu I polymorphism in exon 5 (22). While Alu I digestion revealed two alleles in genomic DNA, analysis of cDNA showed a complete monoallelic expression pattern (FIG. 7C), indicating complete establishment of imprinting of H19 after in vitro differentiation of human EG culture.

Figure 7D:
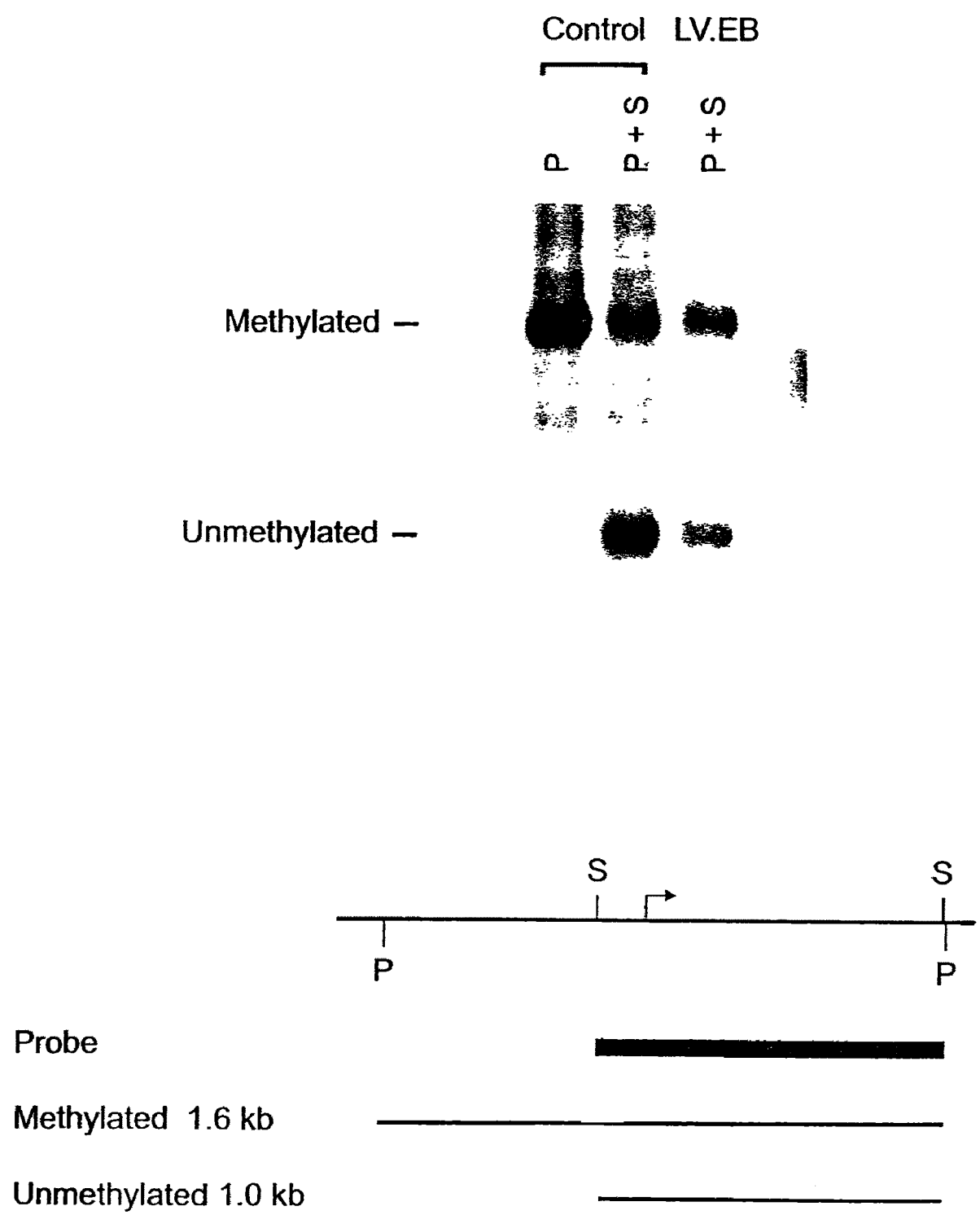

We further examined the methylation pattern of the H19 DMR (23) in differentiated human EG cells. A double digestion of genomic DNA using Pst I and the methylation-sensitive enzyme Sma I revealed a 1.6 kb methylated and a 1.0 kb un-methylated allele in control human tissue samples (FIG. 7D). Analysis of differentiated EG-derived cells showed the same methylation pattern seen in normal human tissues (FIG. 7D), indicating the establishment of a normal imprinting pattern in human EG-derived cells.

Example 7

Experimental Design. We chose a restriction enzyme-based strategy for isolating methylated CpG islands over a PCR-based strategy, to avoid known problems of amplification bias against GC-rich sequences, and in order to obtain larger clone inserts than would be possible by a PCR-based approach. The source of DNA was a Wilms tumor from a male, to avoid cloning methylated CpG islands from the inactive X chromosome, and because this approach would identify either normally methylated CpG islands or those methylated specifically in tumors. The specific enzymes were chosen by an in silico analysis of genomic sequences containing CpG islands. This analysis suggested a two-step approach (described in detail in FIG. 9). The first step involves digestion with Mse I and Hpa II, followed by gel purification of fragments $\geq 1$ kb in length. This step was predicted to enrich approximately 10-fold for CpG islands (enrichment was confirmed by a Southern blot, data not shown), while eliminating all unmethylated CpG islands because of the methylcytosine sensitivity of Hpa II. This "Mse I library" was cloned into the restriction-negative strain XL2-Blue MRF' to avoid bacterial digestion of methylated genomic DNA. CpG islands were further selected by digesting Mse I library DNA with Eag I and subcloning, providing a total expected 800-fold enrichment for CpG islands in this "Eag I" library (see FIG. 9 brief description for details). Taking together the estimated library size and unique clones in it, with the predicted enrichment from the specific enzymatic strategy that was used, we estimated the total number of unique methylated CpG islands throughout the genome to be approximately 800, representing 1-2% of the total number of CpG islands.

Construction of the Mse I library. DNA from a male Wilms' tumor sample was isolated as described (52). 200 µg of DNA were digested overnight with 1000 units of Hpa II (LTI) followed by a five hour digest with 600 units of Mse I (NEB), according to the manufacturer's conditions, and the volume was reduced using a SpeedVac concentrator (Savant). In order to select for fragments $\geq 1$ kb, the digest was passed through a size selection CHROMA-SPIN+TE-400 column (Clontech). Fragments between 1-9 kb were purified from a 0.8% gel by electroelution and passed through an Elutip-D column (S&S). The eluate was ethanol precipitated, cloned into the compatible Nde I site of pGEM-4Z, which was first modified to abolish the Sma I site, transformed into the competent cells of the restriction-deficient strain XL2-Blue MRF' (Stratagene), and plated onto LB-Ampicillin agar plates. Library DNA was prepared directly from plates using a plasmid Maxi kit (Qiagen).

Construction of the Eag I libraries. 100 µg of the Mse I library DNA were digested with 1,000 u of Eag I (NEB) according to the manufacturer's conditions. The digest was ethanol precipitated, and 100 to 1500 by fragments were size-selected by purification from a 1.5% agarose gel, cloned into the Eag I site of pBC (Stratagene), and transformed into XL1-Blue MRF' (Stratagene). DNA from individual colonies was prepared using a Perfect Prep kit (Eppendorf). In order to eliminate MCI-R sequences (Methylated CpG Island-Repetitive, see results) from the final Eag I library, 3.5 µg of the Mse I library was purified, and half was digested with Ace I and half with Tth III1, pooled and digested with Dra III, Sal I, and Asc I, then re-transformed into XL2-Blue MRF'. This step eliminated >90% of the MCI-R sequences, while retaining approximately 30% of the MCI-S and MCI-D sequences (MCI-same in uniparental tissues, MCI-different in uniparental tissues, respectively, see results). Eag I libraries were prepared as described above, after gel purification from three overlapping fractions, 100-700 bp, 400-1000 bp, 700-1500 bp, termed ES-1,2, and 3, respectively.

DNA Sequencing. DNA sequencing was performed using an ABI 377 automated sequencer following protocols recommended by the manufacturer (Perkin-Elmer). The sequences were analyzed by a BLAST search (53) of the NR, dbEST, dbGSS, dbHTGS, and dbSTS databases, and by GRAIL analysis. Chromosomal localization was performed by electronic PCR (ePCR, NCBI), or in some cases without matches using the GeneBridge 4 radiation hybrids panel (Research Genetics).

Southern hybridization. Genomic DNA was digested with Mse I alone or Mse I together with a methylcytosine-sensitive (Hpa II, LTI, or Sma I, NEB) or methyl-insensitive (Msp I or Xma I, NEB) restriction endonuclease according to the manufacturer's conditions. Southern hybridization was performed as described (54).

Example 8

Figure 10:
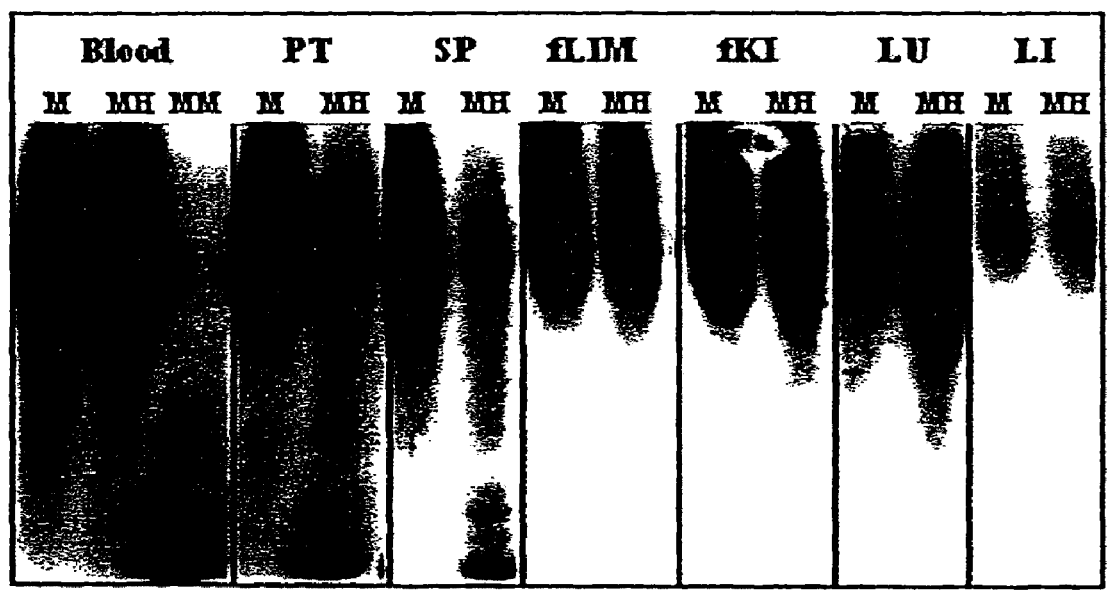
FIG. 10. Methylation of SVA retroposons. DNA was digested with Mse I (M), Mse I+Hpa II (MH), or Mse I+Msp I (MM), electrophoresed on a 1.5% agarose gel, transferred to a nylon membrane and hybridized to a probe unique to the SVA element, SVA-U. LI: liver; LU: lung; fKI: fetal kidney; fLIM: fetal limb; SP: sperm; PT: parthenogenetic tumor (dysgerminoma).

A class of high copy number methylated CpG islands. Our primary goal was to identify unique methylated CpG islands throughout the genome. However, it quickly became apparent that most of the clones in the Eag I library represented high copy number methylated CpG islands. The majority of these were derived from a sequence termed SVA, which constituted 70% of the Eag I library, and that was not previously known to be methylated. The little-known SVA retroposon contains a GC-rich VNTR region, which embodies a CpG island, between an Alu-derived region and an LTR-derived region, only three such elements had previously been described (55-57), although their methylation has not been characterized. We designed a probe, termed SVA-U, unique to the SVA and present in all of the SVA elements, to analyze copy number and methylation of this sequence in genomic DNA. The copy number was estimated to be 5000 per haploid genome (data not shown, L.S.-A. and A.P.F., in preparation). The SVA elements were found to be completely methylated in all adult somatic tissues examined, including peripheral blood lymphocytes, kidney, adrenal, liver and lung, as well as fetal tissues including kidney, limb, and lung (FIG. 10). However, in germinal tissues SVA elements were hypomethylated but not completely unmethylated. This methylation pattern was consistent with a retroposon methylation pattern, where a group of active elements is unmethylated in the germ line and maintains a high GC content, whereas in somatic tissues the element is methylated and silenced. A somewhat less abundant high copy repeat, representing an additional 20% of the Eag I library corresponded to the nontranscribed intergenic spacer of ribosomal DNA, which was a known methylated repetitive sequence (58). A third high copy methylated sequence was the ribosomal DNA internal transcribed spacer and the 28S gene, comprising an estimated 5% of the Eag I library, suggesting that ribosomal gene methylation may be more extensive than was previously suspected. In summary approximately 25% of the Eag I library was accounted for by ribosomal DNA sequences, and 95% of the Eag I library by ribosomal DNA and SVA together. For convenience, we term this class of methylated CpG islands MCI-R (Methylated CpG Island-Repetitive).

Example 9

Identification of Unique Methylated CpG Islands. One of the advantages of our restriction enzyme-based two-step approach is that we could use it to eliminate the high copy number sequences described above. Toward this end, we again performed an in silico analysis to identify combinations of restriction endonucleases that could be used on the Mse I library, to selectively eliminate the two common high copy number methylated CpG islands, and an Eag I library was re-constructed following this procedure. This approach allowed us to uncover unique methylated CpG islands that might otherwise have been obscured.

After eliminating redundant clones, sixty-two unique clones were characterized in detail. All of the sequences were GC-rich, i.e. with a measured (C+G)/N>50%, and they ranged in GC content from 55 to 79%. Forty-five (73%) of the clones showed an observed to expected CpG ratio>0.6, meeting the formal definitional requirement of a CpG island. Thirty of these CpG islands were then characterized by detailed genomic analysis, including radiation hybrid mapping of clones not within the known database, and analysis of methylation in somatic and germline tissues and in ovarian teratomas (OT) and complete hydatidiform moles (CHM), which are of uniparental maternal and paternal origin, respectively.

Figure 11B:
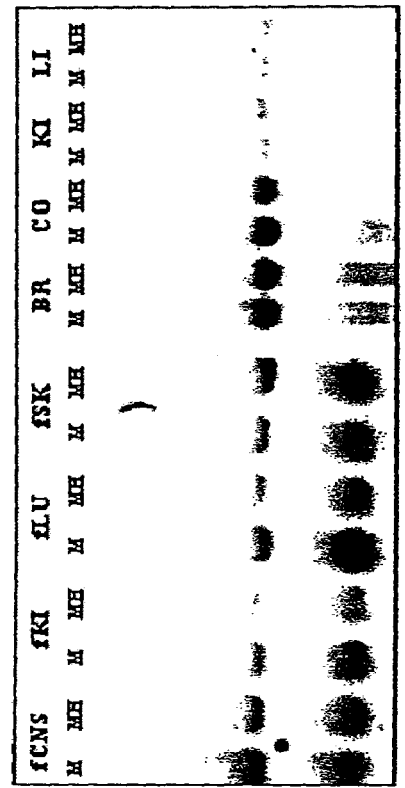
FIGS. 11A-11C. Methylation of MCI-S in normal tissues. DNA from various tissues was digested with Mse I (M), Mse I+Hpa II (MH), or Mse I+Msp I (MM), electrophoresed on a 1.5% agarose gel, transferred to a nylon membrane and hybridized with MCI-S clones.
Figure 11A:
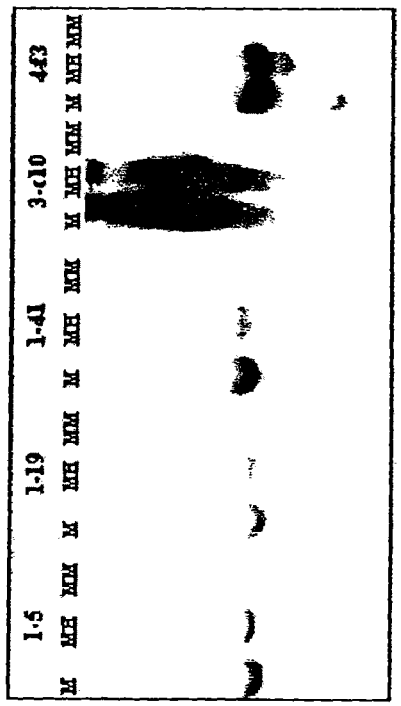
Figure 11C:
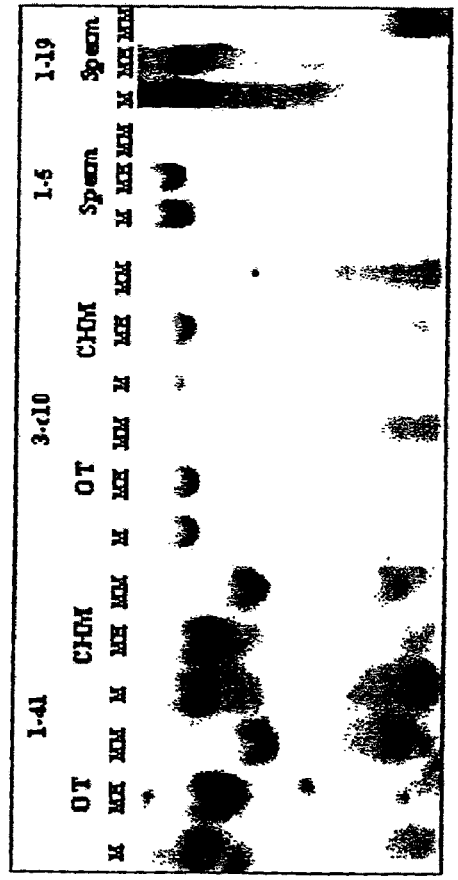

While the sequences recovered in this manner were predicted to be methylated, we confirmed this assumption by direct examination of genomic DNA. Furthermore, as the original source of material was a Wilms tumor DNA sample, we had no a priori knowledge about the methylation of these sequences in normal tissue. Surprisingly, most were methylated normally. More specifically, this analysis revealed that all of the sequences represented methylated CpG islands, and they could be divided into 3 major groups. The largest group consisted of sequences methylated in all tissues examined, including fetal and adult somatic tissues, ovarian teratomas (OT), complete hydatidiform moles (CHM), and sperm. For example, clone 1-41 showed in blood an identical pattern after Mse I+Hpa II digestion, as after Mse I digestion alone, compared to Mse I+Msp I digestion which cut regardless of methylation (FIG. 11A). This was true for other somatic tissues, as well as for ovarian teratoma, hydatidiform mole, and sperm (FIG. 11B,C). Altogether, half of the unique methylated CpG islands fell within this category, which we term MCI-S (Methylated CpG Island-Similar in uniparental tissues).

Figure 12B:
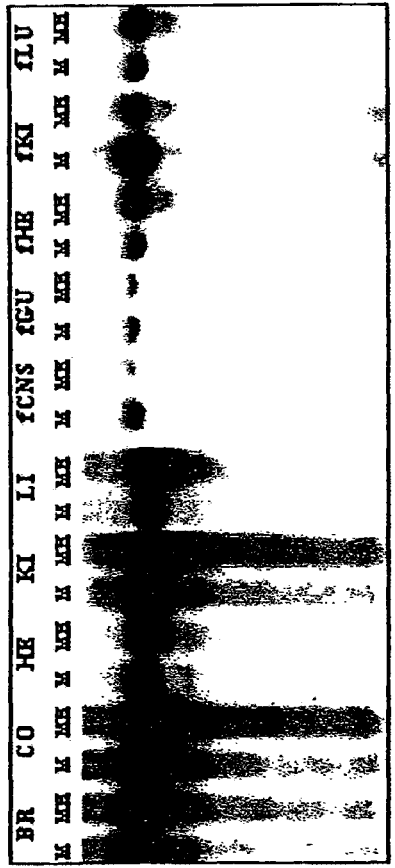
FIG. 12A-12C. Methylation of MCI-D in normal tissues. Tissue DNA was treated as described in FIG. 3 and hybridized with MCI-D clones.
Figure 12A:
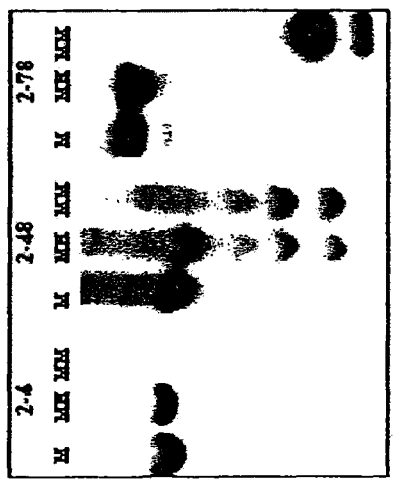
Figure 12C:
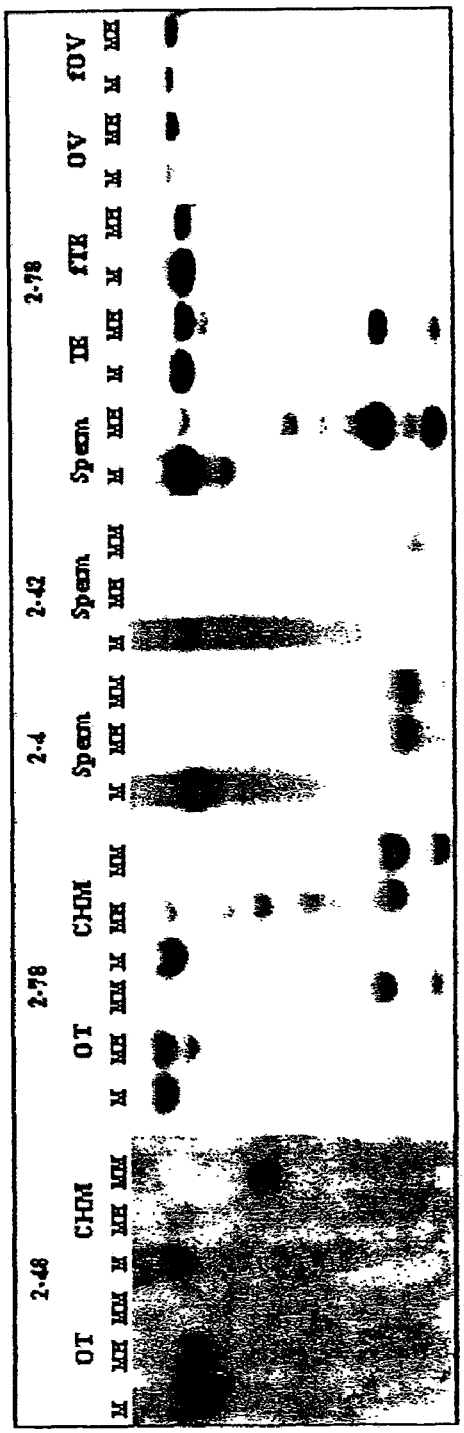

The second largest group, approximately 30% of the unique clones, were methylated in normal somatic tissues, and unmethylated in complete hydatidiform mole (CHM), which are uniparentally derived from the male germline, as well as in sperm. For example, clone 2-78 showed an identical pattern after Mse I+Hpa II digestion, as after Mse I digestion alone, in blood and other somatic tissues (FIG. 12A, B). However, clone 2-78 showed complete digestion after Hpa II treatment of sperm and hydatidiform mole DNA, similar to the pattern seen after Msp I digestion (FIG. 12C). We termed this category MCI-D (Methylated CpG Island-Different in uniparental tissues). All of the MCI-D sequences were methylated in OT and not CHM.

Figure 13:
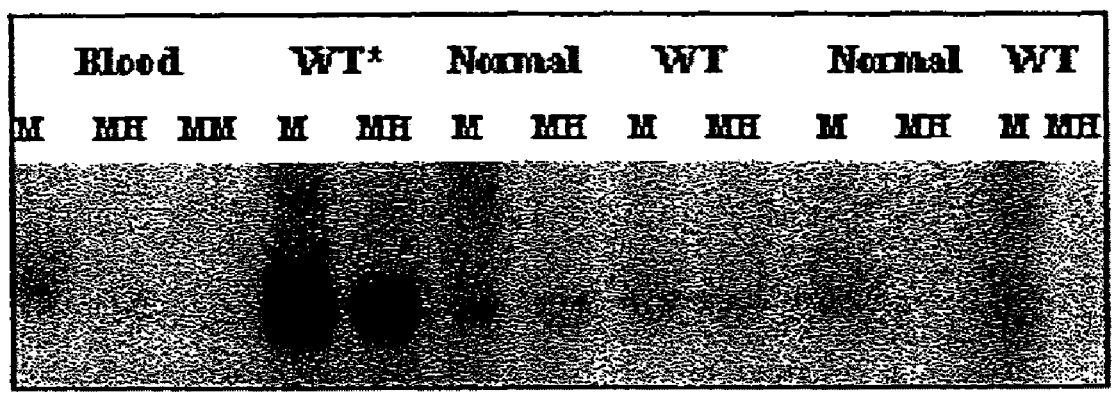
FIG. 13. Variable methylation of MCI-T/2-d10 in normal tissue and Wilms tumor. DNA from normal blood, the tumor that was used to construct the Mse I library (denoted WT*), and two pairs of matched Wilms tumor and normal kidney from the same patients, was treated as described in FIG. 11 and hybridized with MCI-T/2-d10.

The final group, approximately 10% of the unique clones, were unmethylated in normal tissue but methylated in tumors. For example, clone 2-d10 showed an identical methylation pattern in blood DNA after Mse I+Hpa II digestion as was seen after Mse I+Msp I digestion. However, Wilms tumor DNA, from which the Mse I library had been constructed, was fully methylated (FIG. 13). Consistent with our nomenclature, this category is termed MCI-T (Methylated CpG Island-Tumors). Though the MCI-T sequences were identified by virtue of their being methylated in tumor tissue, they may represent sequences of polymorphic methylation in the population, as a second individual showed methylation of 2-d10 in both tumor and normal tissues and a third showed methylation in neither tumor nor normal tissues (FIG. 13).

Example 10

Chromosomal and isochore localization of unique methylated CpG islands. The remainder of the studies described here were performed on the two classes of unique CpG islands that are methylated in normal tissues, namely MCI-S and MCI-D. We first asked whether these sequences were found in a unique location in the genome or were distributed more generally. Surprisingly, there was a striking difference in localization within the genome of the MCI-S and MCI-D sequences. Virtually all of the MCI-S sequences were localized near the ends of chromosomes, either on the last or the penultimate subband of the chromosome on which it resided (Table 2). In contrast, 70% of MCI-D sequences were localized more centromerically. This difference was highly statistically significant (p<0.01, Fisher's exact test). The association of MCI-S sequences near the ends of chromosomes is consistent with an observation of densely methylated GC-rich sequences near telomeres, although that study did not describe methylated CpG islands (51).

TABLE 2

Characteristics of MCI-S and MCI-D Sequences.

| Name | Accession | Gene | Expression | Chromosome | Isochore |
|---|---|---|---|---|---|
| MCI-S/1-5 | AL161774 | — | NA | 13qtel | H2 (54%) |
| MCI-S/1-19 | AF084481 | WFS1 | Br, Bra, Co, Ey, He, Ki, Li, Lu, Ly, Ov, Pa, Pl, Te, Ut | 4p 15 | H2 (52%) |
| MCI-S/1-30 | AC008267 | — | NA | 7qll-21 | H1 (46%) |
| MCI-S/1-41 | NM_018104 | FLJ10474 | Br, Lu, Mu, Pr, Ut | ND | |
| MCI-S 2-e3 | AC010958 | — | NA | ND | H1 (49%) |
| MCI-S 2-h1 | U60110 | N-SGA-b | Br, Bra, Lu, Pa, Pl, Pr, St, Te, Ut | 17q25 | H1 (51%) |
| MCI-S/3-110 | AC023786 | — | NA | ND | H1 (51%) |
| MCI-S/3-12 | AL157939 | — | NA | 10q26 | H2 (56%) |
| MCI-S/3-20 | AA001705 | EST | Retina | ND | |
| MCI-S/3-clO | AK025954 | FLJ22301 | Br, Bra, Co, Ey, Ge, He, Ki, Lu)Ly, Mu, Ov, Pa, Pl, Te | Iq44 | |
| MCI-S/4-f3 | Hs.155647 | EST | Br, Co, Ma, Pr, Te | 19pl3 | H3 (66%) |
| MCI-S/4-g6 | AI361872 | EST | CGAP-CLL | 18q23 | L (43%) |
| MCI-D/1-13 | AP001403 | — | NA | 10q26 | H1 (48%) |
| MCI-D/1-20 | AL161645 | — | NA | 14q21 | L (41%) |
| MCI-D/1-21 | NM 016651 | LOC51339 | infant/fetal brain | 20q13 | H1 (48%) |
| MCI-D/2-4 | U43342 | NFAT | activated T cells | 16p11 | H1 (49%) |
| MCI-D/2-42 | AC026454 | — | NA | 9p11-12 | L (42%) |
| MCI-D/2-48 | Hs.202088 | EST | CGAP-Lung | 18q12 | L (41%) |
| MCI-D/2-78 | AQ090822 | EST | Testis, CGAP-Brain | 8q21 | L (39%) |
| MCI-D/2-e4 | AC012191 | — | NA | I1q24 | H1 (45%) |
| MCI-D 3-30 | Hs.148365 | 5'of EST | fetal Lung/Testis/GCB | 6q24 | L (39%) |
| MCI-D 3-d4 | AF241534 | HYMAI | fetal Heart, CGAP-CLL, Ge | 18q23 | L (43%) |

Expression data was derived from experimental data (not shown) as well as from information in UniGene. Chromosome localization was derived from ePCR and radiation hybrids mapping; Isochore determination was according to the composition of the genomic sequence harboring the clone;
Accession - GenBank accession; NA—not applicable, ND—not done, Br: brain, Bra: breast, Co: colon, Ey: eye, Ge: germ cell, He: heart, Ki: kidney, Li: liver, Lu: lung, Ly: lymph, Mu: muscle, Ov: ovary, Pa: parathyroid, Pl: placenta, Pr: prostate, St: stomach, Te: testis, To: tonsil, Ut: uterus CGAP: Cancer Gene Anatomy Project, CLL: Chronic Lymphocytic Leukemia, GCB: Germinal Center B-Cells.

We also questioned whether, in addition to their apparent chromosomal segregation, the MCI-D and MCI-S sequences localized within compartments of differing genomic composition, i.e. isochores, which are regions of several hundred kb of relatively homogeneous GC composition (59). This analysis showed a striking segregation of MCI-D and MCI-S sequences. Approximately 75% of the MCI-S sequences fell within high isochore regions (G+C$\geq$50%), as might be expected from the high GC content of methylated CpG islands. Surprisingly, however, all of the MCI-D sequences fell within low isochore regions (G+C<50%), i.e. of relatively low GC content, despite the high GC content of the MCI-D sequences themselves (Table 1). This difference, like the chromosomal localization was also highly statistically significant (p<0.01, Fisher's exact test). Taken together, the comparison of MCI-S and MCI-D localization suggest that they may lie within distinct chromosomal and/or isochore compartments.

Example 11

Relationship of unique methylated CpG islands to genes. Most of the MCI-D and MCI-S sequences were localized within or near the coding sequence of known genes or of anonymous ESTs within the GenBank database. These genes serve a wide variety of functions, including the wolframin gene, a transmembrane protein involved in congenital diabetes; sulphamidase, a lysosomal enzyme involved in Sanfilippo syndrome (MPS-IIIA); a cDNA similar to the gene for the extracellular matrix protein tenascin; and an EST adjacent to the Peutz-Jeghers syndrome gene STK11 (Table 2). Half of the MCI-S and one of the MCI-D sequences corresponded to unique or very low copy number variable number tandem repeat (VNTR) sequences. The location of the CpG islands within these genes appeared to differ between the MCI-S and MCI-D sequences, although this difference was not statistically significant. Three of six MCI-D sequences were localized within the promoter or contained the predicted transcriptional start site. For example, MCI-D/2-78 matched EST AW090822, including the start of a 546 amino acid long ORF and a promoter predicted by GENSCAN just upstream of this sequence, and MCI-D/3-d4 was within the promoter and first exon of the HYMAI gene. In contrast, none of 7 MCI-S sequences were found to include the start site of transcription. For example, MCI-S/1-19 was within the last exon of the wolframin gene, and MCI-S/2-hl was within the 5-6 exons of the sulphamidase gene. Finally, some of the MCI-D sequences may lie within or near imprinted genes, consistent with their differential methylation in uniparental tissues. For example, the IGF2R gene, which contains an Eag I site, was identified in the Eag I library (data not shown), consistent with the observation that one allele is methylated in normal cells. In addition, MSI-D/3-d4, which like other MSI-D sequences was methylated differentially in ovarian teratomas and hydatidiform moles, differed from most other MSI-D sequences in that it was only partially methylated in somatic tissues. Interestingly, this sequence was found to lie within the promoter and first exon of the HYMAI gene, which has recently also been demonstrated to be imprinted (60). Thus, a subset of MCI-D sequences may mark the location of imprinted genes.

Example 12

Protocol for EG Cell Line Derivation
Media
1. STO Medium
DMEM supplemented with 10% FBS and Pen-Strep. Used for STO, S1$^4$-m220, S1$^4$-X9D$^3$ culture.
2. EG Medium
DMEM with high glucose (4.5 g/liter) supplemented with 15% FBS (performance tested), non-essential amino acid (0.01 mM), L-glutamine (2 mM), Pen-Strep, and 2-mercaptoethanol (0.1 mM).
Feeder Layer Preparation
1. Gelatin-coated 24-well plate preparation.
Add 0.1% gelatin in dH2O into each wells and incubate for about one hour. Wash the well twice with PBS. Allow the well filled with PBS or dH$_2$O.
2. Prepare feeder layer.
1) STO Culture
STO cells are used as feeder layers for EG derivation and long term culture. Normally STO culture is maintained in 10 cm dish in STO media. Culture must be split before reaching 85% confluence. Irradiation resistance of the maintained culture needs to be tested after a certain period of time. Should cells surviving irradiation found, throw away the culture and thaw a new vial of cells.
2) Prepare Feeder Layer
a. Trypsinize STO from culture the day before dissecting embryo. Suspend cells in culture media in 50 cc tubes. Irradiate cells for 4000 rads. Count the cells and pellet. Resuspend cells in media at $1.5 \times 10^5$ cells/ml. Add 1 ml ($1.5 \times 10^5$ cells) of cell suspension into each well of gelatin-coated 24-well plate. Allow cells settle on the bottom overnight.
b. 2 hours before embryo dissection, change media in the wells into EG media supplemented with LIF (1000 U/ml), bFGF (1 ng/ml), and murine SCF (stem cell factor) (60 ng/ml).
Mice Mating
Natural mating is setup for 129/SvEv female and mus. Castanious male. Male must be older than 7 weeks and female must be between 8-18 weeks.
Put 2-3 females into a male cage in which only one male mouse is kept at the end of the day. Check plug on females next morning. Separate plugged females into new cages (one in each) and label the cage indicating the male partner.
Embryo Dissection
Dissect out the posterior third of the embryo from 8.5 dpc embryo.
Dissect out the genital ridge from 10.5 dpc embryo.
Dissect out the pair of gonads from 12.5 dpc embryo.
Primary Culture
1. Pool all dissected tissue fragments into a 15 cc tube. Rinse with PBS once. Dissociate cells by adding 1 ml of 0.25% tyrosine/1 mM EDTA solution and gently pipetting up and down for 2.5 min. Then add 5 ml of EG media and keep pipetting up and down for about 2 min. Pellet cells at 1000 rpm for 10 min. Resuspend cells into an appropriate volume (for 8.5 dpc, 200 ul/embryo; 10.5 and 12.5 dpc, 1 ml/embryo) of EG media supplemented with LIF (1000 U/ml), bFGF (1 ng/ml), and murine SCF (stem cell factor) (60 ng/ml). Add 100 ul into each feeder layer coated wells of 24-well plate.
2. Plate dissociated cell suspension into at least two separate plates. One with only a few wells plated for monitoring the survival and proliferation of PGCs in culture. Others with most or all of wells plated for EG derivation.
3. After 6 days, some of the wells are stained for alkaline phosphatase each day in order to assess the survival and growth of PGCs.
Secondary Culture and Line Cloning
1. At 9th days, prepare feeder layer plates.
2. After 10 days, cultures are trypsinized and replated: 2 hours before trypsinization, change media for feeder layer plate into EG medium. Wash wells with PBS twice, and add 100 ul of 0.25% trypsin/1 mM EDTA into each well. Incubate plates at 37° C. for 2 min. Add 1 ml of EG media into each well and pipette up and down in the well. Collect trypsinized cultures of all wells into a 15 cc tube, pellet cells and resuspend cells into appropriate volume (1 ml/well) of EG media supplemented with LIF (1000 U/ml). Add 1 ml into each well of prepared feeder layer plate.
3. Monitor the appearance of colonies in culture every day.
4. When most colonies expand into unaided visible sizes, trypsinize the culture with 0.05% trypsin/EDTA and isolate floating colonies form the media. Isolated colonies are subjected to microdrop trepsinization (0.25% trypsin/EDTA) and plated into feeder layer of 24-well plates in EG media supplemented with LIF (1000 U/ml).
5. After two rounds of colony cloning, lines can be passed in 5 cm culture dish without further cloning.

Example 13

EG Cell Staining Protocol
Stage-Specific Mouse Embryonic Antigen-1 Staining
1. Culture EG cells on STO feeder layer on a chamber slide (Nunc).

2. Wash culture twice with PBS containing 2% calf serum and 0.1% sodium azide.

3. Incubate culture with mouse monoclonal antibody (TG-1) against stage-specific mouse embryonic antigen-1 (at least 1:30 dilution) on ice for 30 min. (Ab from Dr. Peter Donovan in NCI)

4. After washed with PBS, culture are incubated for 30 min with FITC-conjugated Fab' fragment of goat anti-mouse IgG (H+L) (Cappell, 1:5 dilution) on ice.

5. Wash culture with PBS. Fix culture in 4% paraformaldehyde before staining for AP.

Alkaline Phosphatase Activity Staining

Use leukocyte alkaline phosphatase kit (catalog No. 85L-3R) from SIGMA and follow the accompanying protocol.

Example 14

Differentiation Essay for EG cells
In vitro differentiation
Protocol I (Natural Differentiation)

1. EG culture on feeder layer is trypsinized (0.05% trypsin EDTA) lightly and pipetted gently to generate small clumps of cells. Separate the EG cells from the irradiated STO cells as written below.

2. Transfer cell clumps into bacteriological plastic dishes and allow cell clumps to grow in suspension for 5 to 7 days. Most of clumps differentiate into simple embryoid bodies, with a single outer layer of extraembryonic ectoderm cells.

3. Return embryoid bodies back to tissue culture plastic dishes. Embryoid bodies will attach and give rise to a variety of cell types over two weeks.

Separate EG Cells from STO Feeder Layer Cells

For all the following protocols, EG cultures are trypsinized (0.25% trypsin/EDTA) and single cell suspension is created. Plate cells into 10 cm tissue culture dish at 37° C. for 1.5 hr to allow feeder layer cells attach the bottom. Replate the media into another plate for an additional 1.5 hr. Then collect media and pellet cells.

Protocol II (DMSO Induced Differentiation as Aggregates)

1. Resuspend cells into RA differentiation medium (DMEM supplemented with 1% dimethyl sulfphoxide (DMSO), 10% FBS, L-Glutamine, Peniciline-Streptomycin) and transfer into bacterialogical dishes.

2. After 4 days, transfer cell aggregates into tissue culture dishes and culture with regular medium.

Protocol III (RA Induced Differentiation as Aggregates)

1. Resuspend cells into RA differentiation medium (DMEM supplemented with 0.3 µM all-trans retinoic acid, 10% FBS, L-Glutamine, Peniciline-Streptomycin) and transfer into bacterialogical dishes.

2. After 4 days, transfer cell aggregates into tissue culture dishes and culture with regular medium.

Protocol IV (Differentiation in Methylcellulaose Medium)

1. Count EG cells and resuspend EG cells in methylcellulose medium* at a concentration of $3.5 \times 10^5$ cells/ml. Transfer 10 ml into each 10 cm bacteriological dish.

2. At day 4, split each dish into 2 dishes and grow for another 10 days with medium replaced daily.

* Methylcellulose medium (500 ml): Weight 3.7 g of $NaHCC_3$ and mix with 10 g of BRL DMEM salt (pack for 1 liter media). Dissolve salts into 86 ml water and pH to 6.9. Mix 20 ml of concentrated salt solution with 268 ml of DMEM, 50 ml FBS, 5 ml each of non-essential a.a., 2.3 ml of L-glutamine, 5 ml of pen-strep, at 100× concentrations, and 4.1 ul of 100% 2-mercaptoethanol. Filter the solution through 0.2 microm filtre. Add 150 ml of 2.2% (w/v) aqueous methylcellulose (Sigma, viscocity of 2% aqueous solution equal to 400 centipoises), mix and store at 4° for 1 hr before use.

Preparation of 2.2% aqueous methylcellulaose: Add 11 g of methylcellulaose power into bottle and add water to 500 ml. Stir the solution in cold room overnight. Put bottle in microwave and boil the solution three times (be careful not to spill the content). Tighten the cap right after the last boiling and leave the bottle in cold room overnight. Store in refrigirator.

Protocol V (DMSO Induced Differentiation as Single Cell Culture)

1. Resuspend cells into EG medium at a concentration of $3 \times 10^4$ cells/ml, and plate into gelatinized tissue culture dishes. Culture for two days allowing cells attach and grow.

2. Change to RA differentiation medium (DMEM supplemented with 1% dimethyl sulfphoxide (DMSO), 10% FBS, L-Glutamine, non-essential a.a., Peniciline-Streptomycin) and replace daily.

3. After 2 days, change to standard medium and replace daily.

Protocol VI (RA Induced Differentiation as Single Cell Culture)

1. Resuspend cells into EG medium at a concentration of $3 \times 10^4$ cells/ml, and plate into gelatinized tissue culture dishes.

2. After two days, change to RA differentiation medium (DMEM supplemented with 0.3 µM all-trans retinoic acid, 10% FBS, L-Glutamine, Peniciline-Streptomycin) and replace daily.

2. After 2 days, change to standard medium and replace daily.

In Vivo Differentiation

1. Harvest EG culture and wash three times with PBS.

2. Count cells and pellet/resuspend them into a concentration of $2 \times 10^6$ cells/ml in PBS.

3. Inject 1 ml cells subcutaneously into nude mice, three mice per cell line.

4. After 3-4 weeks, dissect out tumor and washed with PBS twice. Cut tumor into 2-3 pieces and fix in 4% neutral Formalin more than 1 day. Fixed tissue blocks are processed for histology. Sections are stained with hematoxylin and eosin.

REFERENCES

1. R. D. Nicholls, S. Saitoh S, B. M. Horsthemke, *Trends Genet.* 14, 194-200 (1998); A. P. Feinberg, L. M. Kalikin, L. A. Johnson, J. S. Thompson, *Cold Spring Harb. Symp. Quant. Biol.* 59, 357-364 (1994).

2. A. P. Feinberg, in *Genomic Imprinting: Frontiers in Molecular Biology*, W. Reik and A. Surani, Eds. (Oxford University Press, Oxford, 1998), chap. 9.

3. Y. Kato et al., *Develop.* 126, 1823-1832 (1999); S. Steghaus-Kovac, *Science* 286, 31 (1999).

4. Derivation, maintenance, and in vitro differentiation of EG cell lines: 8.5 d.p.c. embryos, resulted from crosses between male CAST/Ei (Jackson Lab, 7-8 week old) and female 129/SvEv (Taconic Farms, 7-8 week old) mice, were dissected according to Buehr and McLaren (31). To derive EG cell lines, we primarily followed Resnick, J. L. et al. (32) and Matsui, Y. et al. (32) with minor modifications: Primary cultures were carried out in EG culture medium (DMEM with 4.5 g/L glucose, 15% FBS, 100 units/ml penicillin-streptomycin, 2 mM L-glutamine, 0.01 mM non-essential amino acids, and 0.1 mM β-mercaptoethanol) supplemented with leukemia inhibitory factor (LIF, 1000 units/ml), basic fibroblast growth factor (bFGF, 1 ng/ml) and murine stem cell factor (SCF, 60 ng/ml). Cultures were trypsinized after nine days and replated in EG culture medium without bFGF and SCF supplementation. Colonies were picked, and individual EG cell lines were propagated on irradiated STO feeder layers in EG medium with LIF (1000 unit/ml). Spontaneous differentiation of EG cells on plastic was performed according to Matsui, Y. et al. (32). Differentiation using RA, DMSO and methylcellulose medium was carried out as described (33).

5. pEGFP-N3 vector (Clontech) was transfected into SJEG-1 cells by electroporation (250 µF, 0.2 kV). Clones with stable integration, such as SJEG-1/GFP18-1, were obtained by G418 selection (500 µg/ml). 8 to 12 cells were injected into C57BL/6 blastocysts. The injected embryos were transferred to pseudopregnant CD-1/VAF female mice. A total of 87 blastocysts were injected and 4 living male chimeras were obtained. Chimeric mice were identified by the agouti coat color. Chimera 1-1 was mated with 3 female CD-1 mice, resulting in three separate litters of offspring, in which about ⅓ were derived from germline transmitted SJEG-1/GFP18-1 cells.

6. S. Jiang, M. A. Hemann, M. P. Lee, A. P. Feinberg, *Genomics* 53, 395-399 (1998).

7. W. Dean et al., *Develop.* 125, 2273-2282 (1998).

8. P. A. Leighton, R. S. Ingram, J. Eggenschwiler, A. Efstratiadis, S. M. Tilghman, *Nature* 375, 34-39 (1995); L. Thorvaldsen, K. L. Duran, M. S. Bartolomei, *Genes Dev.* 12, 3693-3702 (1998).

9. S. E. Leff et al., *Nat. Genet.* 2, 259-264 (1992).

10. Zubair et al., *Genomics* 45, 290-296 (1997).

11. αmMHCneo vector was kindly provided by Dr. Lauren Field (34). SJEG-1 cells were transfected by electroporation (250 µF, 0.2 kV). Stable transfected lines were obtained by hygromycin selection (200 µg/ml). Transfected EG cells were differentiated on plastic and then on tissue culture surfaces. Upon the appearance of spontaneously contracting cells, G418 (400 µg/ml) was added until the culture fully comprised rhythmically contracting muscle bundles.

12. E. Li, C. Beard, R. Jaenisch, *Nature* 366, 362-365 (1993).

13. K. D. Tremblay, J. R. Saam, R. S. Ingram, S. M. Tilghman, M. S. Bartolomei, *Nat. Genet.* 9, 407-413 (1995).

14. Brandeis et al., *EMBO J.* 12, 3669-3677 (1993); S. Bartolomei, A. L. Webber, M. E. Brunkow, S. M. Tilghman, *Genes Dev.* 7, 1663-1673 (1993).

15. R. Feil, J. Walter, N. D. Allen, W. Reik, *Develop.* 120, 2933-2943 (1994).

16. T. Forne et al., *Proc. Natl. Acad. Sci. USA* 94, 10243-10248 (1997).

17. M. J. Shamblott et al., *Proc. Natl. Acad. Sci. USA* 95, 13726-13731 (1998).

18. T. Tada et al., *Dev. Genes Evol.* 207, 551-561 (1998); Y. Kato et al., *Develop.* 126, 1823-1832 (1999).

19. S. Steghaus-Kovac, *Science* 286, 31 (1999).

20. A pluripotent human stem cell culture was derived from primordial germ cells obtained from the gonadal ridges and attached mesenteries of a 7-week post fertilization female embryo as described (17). Embryoid bodies that formed spontaneously in the presence of LIF were harvested then disaggregated by incubation in 1 mg/ml collagenase/dispase (Boehringer Mannheim) at 37° C. for 30 min. Monolayer cell cultures derived from these embryoid bodies were routinely grown in RPMI 1640 and passaged weekly by using 0.05% trypsin/0.53 mM EDTA.

21. Analysis of IGF2 polymorphism and allele-specific expression was performed essentially as described (30). PCR was performed using [$^{32}$P]-ATP end-labeled primer, and the products were resolved on 5% denaturing polyacrylamide gels following Apa I digestion.

22. K. Hashimoto et al., *Nat. Genet.* 9, 109-110 (1995).

23. W. Reik et al., *Hum. Mol. Genet.* 3, 1297-1301 (1995).

24. K. Latham, *Curr. Topics Dev. Biol.* 43, 1-49 (1999); P. E. Szabo, J. R. Mann, *Genes Dev.* 9, 3097-3108 (1995).

25. J. M. Barletta, S. Rainier, A. P. Feinberg, *Cancer Res.* 57, 48-50 (1997).

26. K. Mitsuya et al., *Genes to Cells* 3, 245-255 (1998).

SSCP assays were developed for each gene: Kvlqt1: PCR was performed using primer set mLQT1-108/208 crossing multiple introns. 2 µl of the PCR products was used for subsequent SSCP carried out in a 20-µl volume containing 1×PCR buffer (BRL), 1 mM MgCl$^2$, 0.2 mM dNTP, 0.5 mM unlabeled primer, 0.1 mM end-labeled primer, and 0.5 units of Taq polymerase. Primer set mLQT1-U/L2 spanning two introns was used for SSCP in which mLQT1-U was end-labeled with [$^{32}$P]-ATP. Reaction products were electrophoresed on 8% SSCP gels (8% bis-acrylamide, 5% glycerol, 0.25×TBE buffer, 4° C.) at 40 W for 6 hr. Igf2: PCR was performed using primer set Igf2-U/L spanning an intron. 10 ng of gel-purified PCR product was used as the template for subsequent SSCP reactions conducted as described for Kvlqt1. Reaction products were electrophoresed on 5% SSCP gels at 6 watts for 10 hr. L23mrp: PCR was performed using primer set L23mrp-101/201 spanning an intron. SSCP were performed using primer pair L23mrp-102/201 with 2 µCi of [α-$^{32}$P]-dATP added to each reaction. SSCP gels were run in the same manner as for Kvlqt1. Sequences of primers used were as follows: mLQT1-108, 5'-CCA CCA TCA AGG TCA TCA GGC GCA TGC-3' (SEQ ID NO: 1); mLQT1-208, 5'-GAG CTC CTT CAG GAA CCC TCA TCA GGG-3'(SEQ ID NO:2); mLQT1-U, 5'-TTT GTT CAT CCC CAT CTC AG-3'(SEQ ID NO:3); mLQT1-L2, 5'-TTG TTC GAT GGT GGG CAG G-3'(SEQ ID NO: 4); Igf2-U, 5'-GAC GTG TCT ACC TCT CAG GCC GTA CTT-3'(SEQ ID NO:5); Igf2-L: 5'-GGG TGT CAA TTG GGT TGT TTA GAG CCA-3'(SEQ ID NO: 6); Igf2-U1, 5'-GAT CTC TCT GCT CCA CTT CC-3'(SEQ ID NO: 7); Igf2-L1, 5'-TTG TTT AGA GCC AAT CAA AT-3'(SEQ ID NO: 8); Igf2r-U, 5'-CTG GAG GTG ATG AGT GTA GCT CTG GC-3'(SEQ ID NO: 9); Igf2r-L, 5'-GAG TGA CGA GCC AAC ACA GAC AGG TC-3'(SEQ ID NO: 10); Igf2r-I2, 5'-CTC CTC TGC GGG GCC ATC-3' (SEQ ID NO: 11); H19-U, 5'-CCA CTA CAC TAC CTG CCT CAG AAT CTG C-3'(SEQ ID NO: 12); H19-L2, 5'-GGA ACT GCT TCC AGA CTA GG-3' (SEQ ID NO: 13); H19-L1, 5'-ACG GAG ATG GAC GAC AGG TG-3'(SEQ ID NO: 14); Snrpn-U, 5'-TGC TGC TGT TGC TGC TAC TG-3'(SEQ ID NO: 15); Snrpn-L, 5'-GCA GTA AGA GGG GTC AAA AGC-3'(SEQ ID NO: 16); Snrpn-I2, 5'-GCA GGT ACA CAA TTT CAC AAG AAG CAT T-3'(SEQ ID NO: 17).

27. Quantitative sequencing assay: PCR was performed with primer set H19-U/L2 crossing an intron. Gel-purified PCR products were used in the subsequent sequencing reaction with primer H19-L1. Two methods of sequencing were used and shown to be concordant: (1) fluorescence-based automatic sequencing; (2) cycle sequencing reactions using the AmpliCycle sequencing kit and the provided protocol (Perkin Elmer). Reaction products were run on 7% sequencing gels at 90 W for 80 min and quantified on a PhosphorImager, with genomic DNA as a control for allele intensity.

28. SNuPE assays: Single nucleotide primer extension was performed as described (35) with minor modifications. Snrpn: PCR was performed with primer set Snrpn-U/L crossing an intron. SNuPE were performed using primer Snrpn-I2, and reaction products were resolved on 15% denaturing polyacrylamide gels. Igf2r: PCR was performed with primer set Igf2r-U/L crossing an intron. SNuPE was performed using primer Igf2r-I2 as described above.

29. S. Rainier, C. J. Dobry, A. P. Feinberg, *Hum. Mol. Genet.* 3, 386-386 (1994).

30. M. Buehr and A. McLaren, in *Guide to Techniques in Mouse Development*, P. M. Wassarman and M. L. DePamphilis, Eds. (Academic Press, Inc., San Diego, 1993), vol. 225, chap. 4.

31. J. L. Resnick, L. S. Bixler, L. Cheng, P. J. Donovan, *Nature* 359, 550-551 (1992); Y. Matsui, K. Zsebo, B. L. M. Hogan, *Cell* 70, 841-847 (1992).

32. P. Szabo and J. R. Mann, *Develop.* 120, 1651-1660 (1994); N. D. Allen, S. C. Barton, K. Hilton, M. L. Norris, M. A. Surani, *Develop.* 120, 1473-1482 (1994).

33. M. G. Klug, M. H. Soonpaa, G. Y. Koh, L. J. Field, *J. Clin. Invest.* 98, 216-224 (1996).

34. J. Singer-Sam, PCR Methods Appl. 3, S48-S50 (1994); J. Singer-Sam and A. D. Riggs, in *Guide to Techniques in Mouse Development*, P. M. Wassarman and M. L. DePamphilis, Eds. (Academic Press, Inc., San Diego, 1993), vol. 225, chap. 20; E. Szabo and J. R. Mann, *Genes Dev.* 9, 1857-1868 (1995).

35. Bird, A. P. (1986) *Nature* 321, 209-213.

36. Bird, A. P., Taggart, M., Frommer, M., Miller, O. J., & Macleod, D. (1985) *Cell* 40, 91-99.

37. Gardiner-Garden, M., & Frommer, M. (1987) *J. Mol. Biol.* 196, 261-282.

38. Antequera, F., and Bird, A. P. (1993). *Proc. Natl. Acad. Sci. USA* 90, 11995-11999.

39. Larsen, F., Gundersen, G., Lopez, R., & Prydz, H. (1992) *Genomics* 13, 1095-1107.

40. Cross, S. H., & Bird, A. P. (1995) *Curr. Opin. Genet. Dev.* 5, 309-314.

41. Yen, P. H., Patel, P., Chinault, A. C, Mohandas, T., & Shapiro, L. (1984) *Proc. Natl. Acad. Sci. USA* 81, 1759-1763.

42. Razin, A. & Cedar, H. (1994) *Cell* 77, 473-476.

43. Barlow, D. P. (1995) *Science* 270, 1610-1613.

44. Merlo, A., Herman, J. G., Mao, L., Lee, D., Gabrielson, E., Burger, P. C, Baylin, S. B., & Sidransky, D. (1995) *Nat. Med.* 1, 686-692.

45. Herman, J. G., Latif, F., Weng, Y., Lerman, M. L., Zbar, B., Liu, S., Samid, D., Duan, D. R., Gnarra, G. R., et al. (1994) *Proc. Natl. Acad. Sci. USA* 91, 9700-9704.

46. Toyota, M., Ho, C, Ahuja, N., Jair, K.-W., Li, Q., Ohe-Toyota, M., Baylin, S. B., & Issa, J.-P. J. (1999) *Cancer Res.* 59, 2307-2312.

47. Huang, T. H.-M., Perry, M. R., & Laux, D. E. (1999) *Hum. Mol. Genet.* 8, 459-470.

48. Shiraishi, Chuu, Y. H., & Sekiya, T. (1999) *Proc. Natl. Acad. Sci. USA* 96, 2913-2918.

49. Hayashizaki, Y., Shibata, H., Hirotsune S., Sugino, H., Okazaki, Y., Sasaki, N., Hirose, K., Imoto, H., Okuizumi, H., et al. (1994) *Nat. Genet.* 6, 33-40.

50. Plass, C, Shibata, H., Kalcheva, I., Mullins, L., Kotelevtseva, N., Mullins, J., Kato, R., Sasaki, H., Hirotsune, S., et al. (1996) *Nat. Genet.* 14, 106-109.

51. Brock, G. J. R., Charlton, J., & Bird, A. P. (1999) *Gene* 240, 269-277.

52. Gross-Bellard, M., Oudet, P., & Chambon, P. (1973) *Eur. J. Biochem.* 36, 32-38.

53. Altschul, S. F., Gish, W., Miller, W., Myers, E. W., & Lipman, D. J. (1990). *J. Mol. Biol.* 215, 403-410.

54. Dyson, N. J. (1991) in *Essential Molecular Biology: A Practical Approach, Vol* 2, ed. Brown, T. A. (IRL Press, Oxford), pp. 111-156.

55. Kawajiri, K., Watanabe, J., Gotoh, O., Tagashira, Y., Sogawa, K., & Fujii-Kuriyama, Y. (1986) *Eur. J. Biochem.* 159, 219-225.

56. Zhu, Z. B., Hsieh, S., Bently, D. R., Campbell, D. R., & Volanakis, J. E. (1992) *J. Exp. Med.* 175, 1783-1787.

57. Shen, L, Wu, L. C, Sanlioglu, S., Chen, R., Mendoza, A. R., Dangel, A. W., Carroll, M. C, Zipf, W. B., & Yu, C. Y. (1994) J. Biol. Chem. 269, 8466-8476.

58. Brock, G. J. R., & Bird, A. P. (1997) *Hum. Mol. Genet.* 6, 451-456.

59. Bernardi, G. (1995) *Ann. Rev. Genet.* 29, 445-476.

60. Arima, T., Drewell, R. A., Oshimura, M., Wake, N., & Surani, A. (2000) *Genomics* 67, 248-255.

61. Brandeis, M., Frank, D., Keshet, I., Siegfried, Z., Mendelsohn, M., Nemes, A., Temper, V., Razin, A. & Cedar, H. (1994) *Nature* 371, 435-438.

62. Bird, A. P. (1980) *Nucl. Acids. Res.* 8, 1499-1504.

63. Yoder, J. A., Walsh, C. P., & Bestor, T. H. (1997) *Trends Genetics* 13, 335-340.

64. Cubas, P., Vincent, C, & Coen, E. (1999) *Nature* 401, 157-16.

---

What is claimed is:

1. A method for isolating methylated CpG islands comprising the steps of
   (a) digesting eukaryotic genomic DNA with a first restriction endonuclease which recognizes a recognition sequence found in A/T rich regions of DNA or found in CpG island-poor regions of DNA;
   (b) digesting the eukaryotic genomic DNA with a second restriction endonuclease which recognizes a 4 base-pair sequence in unmethylated C/G rich regions;
   (c) isolating DNA fragments of at least 1 kb formed by the steps of digesting and inserting the fragments into bacterial vectors;
   (d) transforming non-methylating, non-restricting bacteria with the bacterial vectors to propagate the vectors and render the fragments' progeny unmethylated;
   (e) digesting the unmethylated fragments with a third restriction endonuclease which recognizes a sequence of at least 6 base pair in G/C rich regions; and
   (f) isolating the resulting fragments and inserting said fragments into bacterial vectors to form a library of sequences which are enriched for sequences derived from methylated CpG islands in the eukaryotic genome.

2. The method of claim 1 further comprising the step of eliminating undesired repetitive elements by digesting the resulting fragments referred to in step (f) with a fourth restriction endonuclease which recognizes a unique site in the repetitive elements.

3. The method of claim 1 wherein the first restriction endonuclease is Mse I.

4. The method of claim 1 wherein the second restriction endonuclease is Hpa II.

5. The method of claim 1 wherein the third restriction endonuclease is Eag I.

6. The method of claim 1 wherein the fourth restriction endonuclease recognizes a site in element SVA.

7. The method of claim 1 wherein the eukaryotic genomic DNA is isolated from a male.

8. The method of claim 1 wherein the eukaryotic genomic DNA is isolated from a tumor.

9. The method of claim 1 wherein the eukaryotic genomic DNA is isolated from a Wilm's tumor.

10. The method of claim 1 further comprising the step of:
    testing one or more members of the library of sequences which are enriched for sequences derived from methylated CpG islands to identify sequences which are differentially methylated between maternal and paternal chromosomes.

11. The method of claim 1 further comprising the step of:
    testing one or more members of the library of sequences which are enriched for sequences derived from methylated CpG islands to identify sequences which are differentially methylated between hydatidiform moles and teratomas.

12. The method of claim 1 further comprising the step of:
    mapping one or more members of the library of sequences to a genomic region, whereby location of a methylated CpG island is determined.

13. The method of claim 12 further comprising the steps of:
    identifying an imprinted gene adjacent to the methylated CpG island; and
    identifying a disease which is preferentially transmitted by one parent and which is genetically linked to region of genomic DNA which contains the imprinted gene, whereby the imprinted gene is thereby indicated as a candidate gene involved in transmitting the disease.

* * * * *

SEQUENCE LISTING

```
<160> NUMBER OF SEQ ID NOS: 77

<210> SEQ ID NO 1
<211> LENGTH: 27
<212> TYPE: DNA
<213> ORGANISM: Homo sapiens

<400> SEQUENCE: 1
ccaccatcaa ggtcatcagg cgcatgc                                         27

<210> SEQ ID NO 2
<211> LENGTH: 27
<212> TYPE: DNA
<213> ORGANISM: Homo sapiens

<400> SEQUENCE: 2
gagctccttc aggaaccctc atcaggg                                         27

<210> SEQ ID NO 3
<211> LENGTH: 20
```

```
<212> TYPE: DNA
<213> ORGANISM: Homo sapiens

<400> SEQUENCE: 3
tttgttcatc cccatctcag                                              20

<210> SEQ ID NO 4
<211> LENGTH: 19
<212> TYPE: DNA
<213> ORGANISM: Homo sapiens

<400> SEQUENCE: 4
ttgttcgatg gtgggcagg                                               19

<210> SEQ ID NO 5
<211> LENGTH: 27
<212> TYPE: DNA
<213> ORGANISM: Homo sapiens

<400> SEQUENCE: 5
gacgtgtcta cctctcaggc cgtactt                                      27

<210> SEQ ID NO 6
<211> LENGTH: 27
<212> TYPE: DNA
<213> ORGANISM: Homo sapiens

<400> SEQUENCE: 6
gggtgtcaat tgggttgttt agagcca                                      27

<210> SEQ ID NO 7
<211> LENGTH: 20
<212> TYPE: DNA
<213> ORGANISM: Homo sapiens

<400> SEQUENCE: 7
gatctctctg ctccacttcc                                              20

<210> SEQ ID NO 8
<211> LENGTH: 20
<212> TYPE: DNA
<213> ORGANISM: Homo sapiens

<400> SEQUENCE: 8
ttgtttagag ccaatcaaat                                              20

<210> SEQ ID NO 9
<211> LENGTH: 26
<212> TYPE: DNA
<213> ORGANISM: Homo sapiens

<400> SEQUENCE: 9
ctggaggtga tgagtgtagc tctggc                                       26

<210> SEQ ID NO 10
<211> LENGTH: 26
<212> TYPE: DNA
<213> ORGANISM: Homo sapiens

<400> SEQUENCE: 10
gagtgacgag ccaacacaga caggtc                                       26

<210> SEQ ID NO 11
<211> LENGTH: 18
```

```
<212> TYPE: DNA
<213> ORGANISM: Homo sapiens

<400> SEQUENCE: 11
ctcctctgcg gggccatc                                                    18

<210> SEQ ID NO 12
<211> LENGTH: 28
<212> TYPE: DNA
<213> ORGANISM: Homo sapiens

<400> SEQUENCE: 12
ccactacact acctgcctca gaatctgc                                         28

<210> SEQ ID NO 13
<211> LENGTH: 20
<212> TYPE: DNA
<213> ORGANISM: Homo sapiens

<400> SEQUENCE: 13
ggaactgctt ccagactagg                                                  20

<210> SEQ ID NO 14
<211> LENGTH: 20
<212> TYPE: DNA
<213> ORGANISM: Homo sapiens

<400> SEQUENCE: 14
acggagatgg acgacaggtg                                                  20

<210> SEQ ID NO 15
<211> LENGTH: 20
<212> TYPE: DNA
<213> ORGANISM: Homo sapiens

<400> SEQUENCE: 15
tgctgctgtt gctgctactg                                                  20

<210> SEQ ID NO 16
<211> LENGTH: 21
<212> TYPE: DNA
<213> ORGANISM: Homo sapiens

<400> SEQUENCE: 16
gcagtaagag gggtcaaaag c                                                21

<210> SEQ ID NO 17
<211> LENGTH: 28
<212> TYPE: DNA
<213> ORGANISM: Homo sapiens

<400> SEQUENCE: 17
gcaggtacac aatttcacaa gaagcatt                                         28

<210> SEQ ID NO 18
<211> LENGTH: 229
<212> TYPE: DNA
<213> ORGANISM: Homo sapiens

<400> SEQUENCE: 18
cgggctcggg gtcagggtgg gcagtggaca ctcacgcaac atggaggacc tacagccgcg      60
ggctcggggt cagggcaggc agtggacgct cacacacaga ggacctacag ccgcgggctc     120
agggtcaggg cggacagtgg atgcccacac aacacagagg acctacggcc acaggctcgg     180
```

```
ggtcagggcg gcagtggat gcccacacaa cacggaggac ctgcggccg            229
```

<210> SEQ ID NO 19
<211> LENGTH: 114
<212> TYPE: DNA
<213> ORGANISM: Homo sapiens
<220> FEATURE:
<221> NAME/KEY: misc_feature
<222> LOCATION: (1)...(114)
<223> OTHER INFORMATION: n = A,T,C or G

<400> SEQUENCE: 19

```
cggccgacna ggtgtgcggc acggggccnc gccagactgc aaatgtcatt atctgttatt    60
taccacaaca gaggacgaga ggctgcacaa aattaccgca cttggcaacg gccg         114
```

<210> SEQ ID NO 20
<211> LENGTH: 147
<212> TYPE: DNA
<213> ORGANISM: Homo sapiens

<400> SEQUENCE: 20

```
cggccgccgc gcacctggcc cagggccccc tgcctggcct cggcttcgcc ccgggcctgg    60
cgggccaaca gttcttcaac gggcacccgc tcttcctgca ccccagccag tttgccatgg   120
ggggcgcctt ctccagcatg gcggccg                                       147
```

<210> SEQ ID NO 21
<211> LENGTH: 110
<212> TYPE: DNA
<213> ORGANISM: Homo sapiens

<400> SEQUENCE: 21

```
cggccgtgtg ggcatccgtg tcagagtgct gtgtgccggg cgacgctcag ggcggctgtg    60
cgggcatctg tgtcagagtg ctgtgtgccg ggcgacgctc agggcggccg              110
```

<210> SEQ ID NO 22
<211> LENGTH: 157
<212> TYPE: DNA
<213> ORGANISM: Homo sapiens

<400> SEQUENCE: 22

```
cggccgtggc ttctaccgtg ctgcggggct gcgggtcccg ggtgggccca ttgcccggtc    60
acactcggat cttggaataa aatgtgggcg tccatgtgag gccgaagcag tggctgtgac   120
gccccacgcg gggtgcgatc tctgcgggag ccggccg                            157
```

<210> SEQ ID NO 23
<211> LENGTH: 149
<212> TYPE: DNA
<213> ORGANISM: Homo sapiens

<400> SEQUENCE: 23

```
cggccgcttc aagtacgtcc gcgtgactga catcgacaac agcgccgagt ctgccatcaa    60
catgctcccg ttcttcatcg cgactggat gcgctgcctc tacggcgagg cctaccctgc    120
ctgcagccct ggcaacacct ccacggccg                                     149
```

<210> SEQ ID NO 24
<211> LENGTH: 107
<212> TYPE: DNA
<213> ORGANISM: Homo sapiens

<400> SEQUENCE: 24

```
cggccgcagc cacgcgcagg gaggagcccg gggcaccata gcacagcgcc ggcctcacac    60
acaccctcga ggcccctctc gagccccgc ggagccctcc gcggccg                   107

<210> SEQ ID NO 25
<211> LENGTH: 141
<212> TYPE: DNA
<213> ORGANISM: Homo sapiens

<400> SEQUENCE: 25
cggccgagat ttcctacgaa gaggccctga ggagggcccg gcgcggtcgc cgggagaatg    60
tggggctgta ccccgcgcct gtgcctctgc cctacgccag ccccctacgcc tacgtggcta  120 gcgactccga gtactcggcc g                                              141

<210> SEQ ID NO 26
<211> LENGTH: 125
<212> TYPE: DNA
<213> ORGANISM: Homo sapiens

<400> SEQUENCE: 26
cggccgtggg aagtacgcga ggcagggggg tggccgtggg agggacgcga ggcaggggc    60 ggctgtggga gggacttgag gcagggaggt ggccctggga gggacttgag gcaggggtc   120 ggccg                                                                125

<210> SEQ ID NO 27
<211> LENGTH: 126
<212> TYPE: DNA
<213> ORGANISM: Homo sapiens

<400> SEQUENCE: 27
cggccgccac agccgccgcc atcttcttcc tgcccttgcc ttggtgggtg gcggtttcct    60
gcgccgtgtc tggcttggcc agccggagca ccgcgctggg ctccatgcag ccgggctgcg  120
cggccg                                                               126

<210> SEQ ID NO 28
<211> LENGTH: 194
<212> TYPE: DNA
<213> ORGANISM: Homo sapiens

<400> SEQUENCE: 28
cggccgggcc cacgcccgac agttgcagca gttgcggcga ttgcagcgcg ccggcgcaca    60
ggatcacctc gcggcgggcg cgcagggtgc gcacctggcc gtcctggcga tagcgcacgc  120
cgcaggcgcg gctgccctcg aacaggatcg ccatggcgtg cgcgccggtc tccacccgca  180
ggttggcgcg gccg                                                      194

<210> SEQ ID NO 29
<211> LENGTH: 399
<212> TYPE: DNA
<213> ORGANISM: Homo sapiens

<400> SEQUENCE: 29
cggccgcctc tgacgcgccc cctcttttgt ttcgcccgca gcccatcttc ggagtccagc    60
agcaagtggc gcggcaggcc aaggccttcc tgtcgctggg gaagatggcc gaggtgcagg  120
tgagccggcg ccgggccggc ggcgcgcagt cctggctgtg ttcgccacgg tcaagtcgct  180
gatcggcaag ggcgtcatgc tggccgtcag ccagggccgc gtgcagacca acgtgctcaa  240
catcgccaac gaggactgca tcaaggtggc ggccgtgctc aacaacgcct tctacctgga  300
```

```
gaacctgcac ttcaccatcg agggcaagga cacgcactac ttcatcaaga ccaccacgcc    360
cgagagcgac ctgggcacgc tgcggttgac cagcggccg                           399

<210> SEQ ID NO 30
<211> LENGTH: 183
<212> TYPE: DNA
<213> ORGANISM: Homo sapiens

<400> SEQUENCE: 30
cggccgcggc acatagaact ggagacgcac tgcccgggcc attgtctctg taggaaaggc    60
agacatggca catagaaccg agatgcact gcccgggcca ttgtctctgt aggaaaggca    120
gacatggcac atagaaccgg agatgcactg cccgggccat tgtctctgta ggaaaggcgg   180
ccg                                                                 183

<210> SEQ ID NO 31
<211> LENGTH: 67
<212> TYPE: DNA
<213> ORGANISM: Homo sapiens

<400> SEQUENCE: 31
cggccggggg cacttcaggg ccctcttgtt cacggtgtca tggccttgcg cccctgctg    60 gcggccg                                                             67

<210> SEQ ID NO 32
<211> LENGTH: 110
<212> TYPE: DNA
<213> ORGANISM: Homo sapiens
<220> FEATURE:
<221> NAME/KEY: misc_feature
<222> LOCATION: (1)...(110)
<223> OTHER INFORMATION: n = A,T,C or G

<400> SEQUENCE: 32
cggccgctga gcagcttctg gagcagctgc agcttgccgt cacgggcggc gttgtncacg    60
gcggtgcggg ggtctttggt tcgggcctgc gccaggccat gagccggccg              110

<210> SEQ ID NO 33
<211> LENGTH: 220
<212> TYPE: DNA
<213> ORGANISM: Homo sapiens
<220> FEATURE:
<221> NAME/KEY: misc_feature
<222> LOCATION: (1)...(220)
<223> OTHER INFORMATION: n = A,T,C or G

<400> SEQUENCE: 33
cggccgccan ngggccgncc atgccggccc cggtgagcgc ggcatcgccc tgctggagtt    60
cgcgggcggn acaagctttn gttccngagc accaggccgc gnttcgtcgg gnaccttgng   120
cgcnttannt ggttaggggc ttnncnngag gnggcccngg tnccagncng tnntttcatc   180
tctgntnngg tnanccggct ctntccttgg gacgggncgn                         220

<210> SEQ ID NO 34
<211> LENGTH: 734
<212> TYPE: DNA
<213> ORGANISM: Homo sapiens
<220> FEATURE:
<221> NAME/KEY: misc_feature
<222> LOCATION: (1)...(734)
<223> OTHER INFORMATION: n = A,T,C or G

<400> SEQUENCE: 34
```

```
cggccgntgt ggccaccacg ctcaatggga actctgtgtt cggaggcgcg ggggccgnct      60
cggctcccac cgggacgccc tcgggacagc cgctggcggt ggccccaagc ctnggctcgt     120
cnccactggt cccggcgccc aacgtgatcc tgcatcgcac acccacgccc attcagccca     180
agcccgcggg ggtgctgccc gcccaanctc taccagctga cgcccaagcc gtttgcgccc     240
gcgggcgcca cgctcaccat ccagggcgag ccggggcgc tcccgcaagc ancccaaggc      300
cccgcanaac ctgacgttca tggcggcggg gaaggcggnc caagaacgtg gtgctgtcgg     360
ggcttccccg cncctgcgct gcaaagcgaa cntnttcaan cagccaccgg gcaccancac     420
cggagcggcc ccgccgcaag cccccgcggg gcccttgaan anaacccatg atcnttccac     480
ctttcttgaa cccaaggnaa gcagnatttg tcattccccc gcccaannaa catncctgtc     540
cgggccaaaa cncaattttn ctactgntct tgggcacccc cnggcggntg cagcttttcct    600 gcagnattct tttaancnct tncccgggnc aacnntgggg ccgggnaana acctnggcgg     660
gcngcttttt aaaaantaag tnggattccc ccggggcctg gtaaggaaat nntnaaattn     720 nanagnlctt attn                                                       734
```

```
<210> SEQ ID NO 35
<211> LENGTH: 689
<212> TYPE: DNA
<213> ORGANISM: Homo sapiens
<220> FEATURE:
<221> NAME/KEY: misc_feature
<222> LOCATION: (1)...(689)
<223> OTHER INFORMATION: n = A,T,C or G

<400> SEQUENCE: 35
cggccgccat ctcgccgtcg tcccgcgggg tgcccggggc gttgctcagg ccggccacgg      60
cgccggggga gctcttcggc aacccgtcca tgtcgcccga gcccagggat ccgcttacgt     120
ggtgaggctc catcgcgctc atggcggcca tgggcccctc cggggcaggg ccgagcggga     180
aattagccct gccggcaccc ggcccgatgg ggttcatgat agtgtacatg ttttcactgg     240
agttggtaga atctccaggg ctaggcatga tgaggtgttc cagggggccc acctcctcct     300
gggggtcccg tgtagctgcc aggggatgag gaggagtagg ggatcgagtt ccactgggg      360 ctggcccacg ggccacgaac tcctgggccc atgttcatgg caggcaggcc tgggccggca     420
agggagttgg gtgggggtcg catgccgctc atagctntgg ggccccacgc tggcatgccg     480
cgaggaggcg tcaccctncg cattgggccg ccatgcttcg gatgcccctt gggttcgtgg     540
ggagggctcc atggcgccag ggaggaaggg atgggaaccc gggaggcctg cnggagctga     600
cttaacatnc gcagggnggg nccgggaccc cctgggaagc gccgtnacat taaaggctnn     660
cccgtgaagg cccatnacgg ggcatttgg                                       689
```

```
<210> SEQ ID NO 36
<211> LENGTH: 791
<212> TYPE: DNA
<213> ORGANISM: Homo sapiens

<400> SEQUENCE: 36
cggccgattc ggagagccgg ataggtagg gccgcagaag tttctgagcg cggccaagcc      60 agcagggc tcgggcctga gccctcggat cgagatcact ccgtcccacg aactgatcca      120
ggcagtgggg cccctccgca tgagagacgc gggcctcctg gtggagcagc cgccccctggc  180 cggggtggcc gccagcccga ggttcaccct gcccgtgccc ggcttcgagg ctaccgcga     240 gccgctttgc ttgagccccg ctagcagcgg ctcctctgcc agcttcattt ctgacacctt     300
```

```
ctcccctac acctcgccct gcgtctcgcc caataacggc gggcccgacg acctgtgtcc   360
gcagtttcaa acatccctg ctcattattc ccccagaacc tcgccaataa tgtcacctcg   420
aaccagcctc gccgaggaca gctgcctggg ccgccactcg cccgtgcccc gtccggcctc   480
ccgctcctca tcgcctggtg ccaagcggag gcattcgtgc gccgaggcct tggttgccct   540
gccgccggga gcctcacccc agcgctcccg gagcccctcg ccgcagccct catctcacgt   600
ggcaccccag gaccacggct ccccggctgg gtaccccct  gtggctggct ctgccgtgat   660
catggatgcc ctgaacagcc tcgcaccgga ctcgccttgt gggatccccc ccaagatgtg   720
gaagaccagc cctgacccct cgccggtgtc tgccgcccca tccaaggccg gcctgcctcg   780
ccacatctac c                                                        791

<210> SEQ ID NO 37
<211> LENGTH: 65
<212> TYPE: DNA
<213> ORGANISM: Homo sapiens

<400> SEQUENCE: 37
cggccgttca cacacactca ggacccgcac ggcctttcca cacacagtca ggacccgcac   60
ggccg                                                               65

<210> SEQ ID NO 38
<211> LENGTH: 788
<212> TYPE: DNA
<213> ORGANISM: Homo sapiens

<400> SEQUENCE: 38
cggccggggg gcccctgggg agctaggccg ggctcgggca caggcaccgg cacgggcact   60
ggcaccggca ccggcacggg caagggcacc gacccgacgg cggtgggcgc gggccgggag   120
ccgctgccgc tctcggtcag caccgtccgc ttgagcggcc caggcgcctc gaggcgcagt   180
ggcccggcgg cgggcgggcg gtccccgggg gcttgcgcg  cgcggtgcga gggccggcgg   240
cgcagctcgg acgtgagctc gtgcttgagg aagcggaaca cctccttggc tgggccgcgg   300
cgctcgggct ccagggccag taagcgctgg aacatgcgca gcgcgggctc ggtgaagcgg   360
cgccactgcg aaggcagccc cggcaggcgg ccccgctgcc agcgcacgaa ctcctcgaag   420
aaggcgtcgg cgcccgacgc cgcctcccac ggaagttgcc ggtgagcacg cagaagatga   480
gcacgccgaa ggcccacacg tccacgcccg tgtccaccgc cagcccgtcg gcgcggcccg   540
cctggcacac ctcaggcgcc gtgtaaggga tggtgccgct cacgcgcttg acgcggcagc   600
ccacgcggcg cgtcatgccg aagtcggcca gctttacgcg gcggcactcg cggtcgaaca   660
gcagcacgtt ctcgggcttg atgtcgcggt gcaccagctg ccgcccgtgc atgaagtcca   720
gcgccaggcc cagctgctgc acacagcgct tcaccgtgtc ctcagggagc cccacctgcg   780
ggcggccg                                                            788

<210> SEQ ID NO 39
<211> LENGTH: 1123
<212> TYPE: DNA
<213> ORGANISM: Homo sapiens

<400> SEQUENCE: 39
taaaccaatt tcacaggcaa gtttcccttg aaaacaact  ccttgccata atcatcacat   60
tcattgagtg accatctacc aaatgcttta ctcccatgat ttcatgtaat attgacattc   120
accctacaaa gtagatggta ttacagtgtc tgttttacaa gtgagaaatc cgaggaacag   180
```

```
gaagtcaatt tgccaagtgt tgcacagcta aatcgagatt ccagagaatg tcacctcaaa      240
gcttctagtg gggctgtcat gtaggttgtg gtcgctttgg ataacaggag acgctaagga      300
aaatcagtac tggttactga ggatggaaga ggcgcarata tttcaccaca ggcgacgaaa      360
accccacttt taggctggcc acacaggagc cccgaggaaa ctatgcgtcc ccttcctccc      420
cgcccccaca ctgccctggc ctggcggagc agcggccgca agtgtaactg ttgttgccca      480
gatcgaacca agcccggtcc cagtgacgag cagcggcctg cggggccaga gcgtctggga      540
gcctttcatg accccaaagc ccaggggaggt ccccgcacca tcgggccccg cgccctagct      600
cggtccgccg tcgagggtgc ctgaagtccc ctgcgggcgc cggggagaaa gcccggggct      660
tagcctcctc catccccagc catctgtcac cgcctcctag gccccggctg gagcccatg       720 ggcgcctccc gcgcctacca aggagccagg gagacaagga tccggagac ctctggggcg       780 ccctccagct gaggattccg ccgcggctcc cgcagccgct tctccccatt cggtgcagcc      840
cacctggccc agctctcggc cggtctccct cggaggtccg aaaagggaga gggcgggcca      900
gggctccccg ctggccggag ccgcagcccc tttccccctc ccccacccag gaccccttcc      960 cggacccctcc tgggcgcagc cctcacctgc tgcccgcacc gcctccgagg aaggccctcg     1020
ggctccacct ggcctcatca ccgcttccct tatccgggag gaggaggaaa ctcaaccctc     1080
taggccaggc cctgtgctca ctttagatac tttatttcgt tta                       1123

<210> SEQ ID NO 40
<211> LENGTH: 384
<212> TYPE: DNA
<213> ORGANISM: Homo sapiens

<400> SEQUENCE: 40
cggccgaaga tcgtgaccga cacgcgcacc ttggatttgt cgtagttgac ttcctcgacc       60
gagccgttga agtcggtgaa ggggccttcc ttgacgcgca cgacctcgcc gaccgtccac      120
tcgaccttgg gccggggctt ctcgacgccc tcctgcatct ggttgacgat cttcatgacc      180
tccgcctccg agatcggggc cgggcggttc ttggcgccgc cgacaaagcc cgtcaccttg      240
gaggtgtgct tcaccagatg ccaggactcg tcgtccatga acatctcgac cagcacgtag      300
ccggggaaga agcggcgctc ggtaacggcc ttcttgccgt tcttcagctc gacgacctct      360
tcggtaggca ccaggatgcg gccg                                             384

<210> SEQ ID NO 41
<211> LENGTH: 100
<212> TYPE: DNA
<213> ORGANISM: Homo sapiens

<400> SEQUENCE: 41
cggccgccag cccgcccaga agccacagac aagacatagg tagccgtagt tggactgacg       60
ggcagggccg gcggggcagc cccctccgcg tccccggccg                            100

<210> SEQ ID NO 42
<211> LENGTH: 1578
<212> TYPE: DNA
<213> ORGANISM: Homo sapiens
<220> FEATURE:
<221> NAME/KEY: misc_feature
<222> LOCATION: (1)...(1578)
<223> OTHER INFORMATION: n = A,T,C or G

<400> SEQUENCE: 42
cggccgctgg gtttgttttc acgtgcggat cggattttcg tggtcactac tcgcagncgc       60
```

```
tgctctcggg cgtcccgaag ccgcaggtac agctcccgcc aagactcgtg ctcctgtggc    120
tttccttcct tgaagtcctg gaggcaatga atcctccata attcatctgt ctctcgagcg    180
agtgcggcat tgtctttctc tgtgcggtac ggctgatcgg gcgtccaccc ttccagaacg    240
ggttcaagaa ccgagtaggg gacccccttcc acgtcgccga gggcgtccgg attgttccta    300
ggcacccgga ggcactgctg gcgcagcgtc ggcacctgga gctggcaggc aggcctggag    360
cccgagtaca ccggcatctt agcgttcact ctgcgtccag ggaaagcagc ttcctcctgg    420
agcgttggcg cggagagtgc ttctgggttt gcctgggagg tcatggcctc aaaagcggac    480
agcagatcgt agttggcctg catccaggcc tctgaggggt cccagagctc cgagaagaca    540
tggctgggca ccgttttcgg cccggcggaa tcaagcgccg gccgcctgca gcctctctga    600
ctggctttcc tggacaggag gcgatttctg agccgaagcc ccgcgggacg atttgtgccc    660
cttgctgtgg ctccccaccg cttcccctg gggttggccc tggcagcctt gaccagcag    720 aggcccgccc tgagcggcgt gagcgtggcc tcttccgggt tgctcccgg gcacagcggg    780 ctcaggcccc tcgggcatcg ggaggggagc ggtgcgcgtt ggagggtccc gatggggcc    840 ggaatcagct ggggccattc tggggcgctt tctctcggct ctgggctcgc gactgggaga    900
cctcgggtga ggtctctgtt gccccggagg tgttctgcgt gctgtccgtc tgtgctcagg    960
gctgtgagat gggctcctgg gggccgtcgc gttttctggg aagccccagg ccttttcccg   1020
ctcctgaaga gcctccccga agcgctgtcg ggaagcgctc tcctcagggt cctgcgggtc   1080
aggcccggtg tttcggtcca cgagcaccag cttcttccac cgggccgcta agtctctggc   1140
aaagtcgccc acgtgctggt gcttccgcag gcgcttcacc gtctttctga ttccagtctc   1200
cgccaggatg tctgcggtca tgggcaaggc ggagagtttc tgcaaatatt tctctagctt   1260
tttcggctcc gtcttagtgg ccagacgcac ctgcagcttc cccactgcgc gcagcgtagt   1320
ggaccctgcc gccatctcgc cagagctgtg caggcgtcgc tgtcctcgcg gtcgcggctc   1380
tgtccgagct cggggcggcg gcacaggcag tctggggtgg ccggtcctcg ctgcccggtc   1440
gccaggcggc gacctcggga tgtggagtca cagcctggag cgagctgggt cctcggagca   1500
gcgggccact tggtctggaa cgccggtcct tgcagacagc tgagcaggcc cgcttctgtt   1560
cctcgggatg tgcggccg                                                 1578
```

<210> SEQ ID NO 43
<211> LENGTH: 102
<212> TYPE: DNA
<213> ORGANISM: Homo sapiens

<400> SEQUENCE: 43

```
cggccgcccg ctccggaaca cggcggcagc tcatctgaat tcaaattacc ccgggagccg     60
cgcgatgcca gccataactc agcctgcgga ggagtgcggc cg                       102
```

<210> SEQ ID NO 44
<211> LENGTH: 243
<212> TYPE: DNA
<213> ORGANISM: Homo sapiens

<400> SEQUENCE: 44

```
cggccgatgt cggcatcgcg atcggcaccg gcaccgacgt ggccgtggaa gccgccgacg     60
tggtgctgat gtccggcagc ctgcagggcg tgccgaatgc gattgcgctg tccaaggcca    120
ccatgggcaa catccggcag aacctgttct gggcctttgc ctacaacacg gcgctgatcc    180
ccgtggccgc cggcgcgctc tatcccgcgt atggtgtcct gctgtcgccg attttgcgg    240
```

```
ccg                                                                      243

<210> SEQ ID NO 45
<211> LENGTH: 342
<212> TYPE: DNA
<213> ORGANISM: Homo sapiens
<220> FEATURE:
<221> NAME/KEY: misc_feature
<222> LOCATION: (1)...(342)
<223> OTHER INFORMATION: n = A,T,C or G

<400> SEQUENCE: 45
cggccgggct ntttgattgg ctgccgcgtc ggcgatccac gccacaattg ttccctaaga        60
ccgtctgccg ccagcgagcg ccaggtgcgg agcgggcgtt agaagttgct ggcagtcaga       120
ggcaggggag ctgtcactcg cggcgagccg ggcggcggcc agggcgcaaa gttgagagca       180
gtctctagtc tgagcctttc agtcgccttc cagtatcatc agtaccacgg gctccacctt       240
gctgcggccc ctcagcaacc cagtgcacct gccactcgac caggtaggta ggccgaggca       300
cccgggcgtc ggtcatcgcg ccttcgccgc cctttgcggc cg                         342

<210> SEQ ID NO 46
<211> LENGTH: 443
<212> TYPE: DNA
<213> ORGANISM: Homo sapiens
<220> FEATURE:
<221> NAME/KEY: misc_feature
<222> LOCATION: (1)...(443)
<223> OTHER INFORMATION: n = A,T,C or G

<400> SEQUENCE: 46
cggccggcaa ggctcaggac ctgcaggcca tggagtggcg aggctgccat ggagtggcga        60
ggctgccgtg gagcgcggag gccgggtacg cctgcgcgtg gagcgcgaag gccgggtaca       120
cctgcgcgtg gagcgcggag gccgggtaca cctgcgcgtg gagcgcggag gccgggtaca       180
cctgcgcgtg gagcgcggag gccgggtaca cctgcgcgtg gagcgcggag gccgggtaca       240
cctgcgcgtg gagcgcggag gccgggtaca cctgcgcgtg gagcgcggag gccgggtaca       300
cctgcgcgtg gagcgcggag gccgggtaca tctgcgcgtg gcacgcggag gccgggtaca       300
cctgcgctca tcgcacacca gcgcccacgc ccagacgtac tcgcgggaag gacagcnttt       360
tntancnaaa aancgaatgg tcaacccgnt ttanttaaca cgggccancc cggaaacagc       420
ccgacacgga ccgngacggg ccg                                               443

<210> SEQ ID NO 47
<211> LENGTH: 383
<212> TYPE: DNA
<213> ORGANISM: Homo sapiens
<220> FEATURE:
<221> NAME/KEY: misc_feature
<222> LOCATION: (1)...(383)
<223> OTHER INFORMATION: n = A,T,C or G

<400> SEQUENCE: 47
cggccgcaag gagagcctcg atggcttcgt ggagaccttc aagaaagagt tgtccagaga        60
cgcttatcca ggaatctacg ccttggactg tgagatgtgc tacaccacgc atggcctana       120
gctgacccgc gtcaccgtgg tggacgccga catgcgagtg gtgtacgaca ccttcgtcaa       180
gcccgacaac gagatcgtgg actacaacac caggttttcc ggagtcaccg aggccgacgt       240
cgccaagacg agcatcacgt tgccccaagt caagccatc ctgctgagct ttttcagcgc       300
ccaaaccatc ctcatcgggc acagcctgga gagcgacctg ctggccctga agctcatcca       360
cagcaccgtg gtggacacgg ccg                                               383
```

<210> SEQ ID NO 48
<211> LENGTH: 598
<212> TYPE: DNA
<213> ORGANISM: Homo sapiens
<220> FEATURE:
<221> NAME/KEY: misc_feature
<222> LOCATION: (1)...(598)
<223> OTHER INFORMATION: n = A,T,C or G

<400> SEQUENCE: 48

```
cggccgaggt ggtcggagtc gcagggcccg tggaaggcct cggggaggag gagggtgagc      60
aggcggcagg cctggccgca gtcccccagg gcgggagcgc cgaggaggac tcagatatcg     120
ggcccgcgac ggaggaagag gaggaggagg aagaggggaa cgaggcggcc aacttcgact     180
tggcggtggc cacccgtcgg tacccggcgg cgggcattgg cttcgtgttc ctgtacctgg     240
tccactccct tctccgccgc ctctatcaca acgaccacat ccagatagcg aaccgtcacc     300
tcagccgcct gatggtgggg ccccacgctg ctgtgcccaa cctctgggac aaccctcccc     360
tgctgctgct gtcccagagg ctgggtgcag ggctgcagc cccagaaggc gagggcctcg      420
gcctgatcca ggaggcttgc gtcggtccag gaggccgcgt cggtcccaga gcctgcagtg     480
ccagctgacc tggccgagat ggccagggag cccgcggagg aaggccgcaa atgaaaaacc     540
cccaaaagaa ggccgcagag gaagaactca cagaggaggc cacagangaa ccggcccg      598
```

<210> SEQ ID NO 49
<211> LENGTH: 677
<212> TYPE: DNA
<213> ORGANISM: Homo sapiens
<220> FEATURE:
<221> NAME/KEY: misc_feature
<222> LOCATION: (1)...(677)
<223> OTHER INFORMATION: n = A,T,C or G

<400> SEQUENCE: 49

```
cggccgacgg tggtgtactg agcggccagg tcggctcggg ctgccggggt gttggggacg      60
aagtaaggca cctggggcag gcggtgggga gccaggctta aacaggcac cggggagcg      120
gtgtccagcc ttctccccgg ggcctcctgc aaatgggtta gcccanaaca gcctcactcc     180
ggaccacccc gtctctctac ggttctctct gtgccccga ggttgggaac ctgaatccga      240
tttggtcaga gcctctttct tcatcatcta gggccagggc tgcaagctcg taggaggcca     300
gggtccccga cccagggctg acgggcgtcc tgaaacacgg gaggggccgt cctaccagca     360
cgtccagtgg gtcgtaggcc tgggggggtcc agtctgggat acgacccatg ccgctctctt     420
cgtttgcaaa cttctcacaa aangttncct actggggctg ggantgccca cagcggtggg      480
ggtcgtggga aagccaccta aaagaaanaa aggccttcac nggaagangt tnattgncaa      540
ggctgcgggg ccacttgcca cgtggcacaa gaaancectc nggttttgcc tcttcttttg     600
ttttggaant naacctgtga ncctaattgc tnaagtttcc cattttcctt tttccctttg      660
accaagctta acttaat                                                    677
```

<210> SEQ ID NO 50
<211> LENGTH: 669
<212> TYPE: DNA
<213> ORGANISM: Homo sapiens
<220> FEATURE:
<221> NAME/KEY: misc_feature
<222> LOCATION: (1)...(669)
<223> OTHER INFORMATION: n = A,T,C or G

<400> SEQUENCE: 50

```
cccacaccc tcctcagcat ttgccgtctg tgtccacgcg actgcccac gccctcctta      60 gcatttgcca tccatgccca tgtggccgcc ccacgccctc ctcagcattt gccctctgtg    120
tccctgcggc tagccaatgc cctcctcagc atttgccctc tgtgtccacg tggccgcccc   180
acaccctcct cagcatttgc cctctgtgtc catgcagccg gcccacgccc tcctcagcat   240
ttgccctctg tgtccacgca gccggcccac gcctcctca gcatttgccc tctgtgtcca    300
tgcagccggc ccacgccctc ctcagcattt gccctctgtg tccacgcagc cggcccacgc   360
cctcctcagc atttgccctc tgtgtccacg cagccggccc acgccctcct cagcatttgc   420
cctctgtgtc cacatggtcg ccccacgccc tcctcagcat ttgctgtctg tgtccacgtg   480
gccgccaagc cctcctcagc atttgcctgt gtccacgcag ccggccacgc cctcctcagc   540
atttgccctc tatgtcacgt ggccgcccac gccctctcag aatttgctgc tgngacacgt   600
ggcaccccat gccctcttaa gatttgcatn catgcccacg tggcacccca cgcccttctt   660
aagatttgc                                                            669

<210> SEQ ID NO 51
<211> LENGTH: 91
<212> TYPE: DNA
<213> ORGANISM: Homo sapiens

<400> SEQUENCE: 51
cggccggccc agccctgcca tgcccgcctc ctcaggggag tacgcccgcg catcggtgcc    60
ggagagggga gccaggctgg cctgccggcc g                                    91

<210> SEQ ID NO 52
<211> LENGTH: 154
<212> TYPE: DNA
<213> ORGANISM: Homo sapiens

<400> SEQUENCE: 52
cggccgcatt ttatagtcag acacaaccac aacatggttg tgaccgggca gtcgaaccct    60
caggatcgac ccaagagaca tgaaactacc cacacaaagg ctgctatggg aacatgcacg   120
acactcctcc ttcctaatag ccaaaacacg gccg                                154

<210> SEQ ID NO 53
<211> LENGTH: 89
<212> TYPE: DNA
<213> ORGANISM: Homo sapiens

<400> SEQUENCE: 53
gcggccgggg acccacgcca tggtgccggg ctatgggtgt ggggtcagcc agggacccac    60
aacatcgcac tggcctgtgg ggtcggccg                                       89

<210> SEQ ID NO 54
<211> LENGTH: 113
<212> TYPE: DNA
<213> ORGANISM: Homo sapiens

<400> SEQUENCE: 54
cggcccgcgt tatatgacat tccacgttat gtgacattcc ggtgtgccgg cgtgtggccg    60
cgttatatga cattccacgt tatgtgacat tccggtgtgc tggcgtgcgg ccg           113

<210> SEQ ID NO 55
<211> LENGTH: 914
<212> TYPE: DNA
<213> ORGANISM: Homo sapiens
```

<400> SEQUENCE: 55

```
cggccgttct ctgttacctc tctctggaga ccccggcttc tcccctgaag gcctgggagc      60
ctcacccacg gcctggcccg gagagcggtc gtgatgagga tcaaaagaag caaggctgtg     120
gctgggacag ggcactgctc ggaggcccgc cctggaggca ggcggccacc agccttctct     180
ctccttcccg cactttctcc gggccccggt cgcagggacc agcgggcagc cttggctctg     240
gggcgccctc ctttctccct gcagcccag gcgggcttcc ggggctgcg cttcctcccc       300
agccaaggac agcgctcacc cgcgcccag tccccacgca ccagctgtgc agccgccgcc      360
gcctctctcg tctccgtcca gtgagttctc cgcactgcag agggcgagat cccgaaggcc     420
tggatccgcg cagaagcagg gagcaccttc catggccgcc gccatcctca gcaccgtccc     480
gcggctgccg ccatcctcag caccggaagg aaaaccaggc cgccgccatc ctcagcaccg     540
gaaggaaaac caggccgccg ccatcctcag caccggaagg aaaaccgggc cgcagcacgg     600
ccttgttggg ctccctccga gctctctgcc gccttcatga tccagcccg gtctgacccc      660
cgcctccttt ctggcctttg ttccaccccc tgtctgagcc ttccccagtc cggactcgag     720
gccgctctgt gcaatgccac ccttcgctac cccgcctggt ccagcggatc cgcccccagc    780
ctctccaggc cggcgcctcc tctaccggga ctcagctgcg cgctcctcaa cgggcctccc    840
cggcggcgtc tgcgctgctg gagtcggcgt ccggctcctc ccgagcaccg gggctcctgc   900
gggctccgcg gccg                                                      914
```

<210> SEQ ID NO 56
<211> LENGTH: 641
<212> TYPE: DNA
<213> ORGANISM: Homo sapiens
<220> FEATURE:
<221> NAME/KEY: misc_feature
<222> LOCATION: (1)...(641)
<223> OTHER INFORMATION: n = A,T,C or G

<400> SEQUENCE: 56

```
cggccggcgc ttcccgcacc tcccggcgct gctgctacac cggcgccgcc agcatctgcc      60
agagcggccc cgccgctgcc cgctgtgcgc ccgcaccttc cggcagagcg cgctgctctt     120
ccaccaggcg cgggcgcacc ccttgggac aacctctgac cctgctgccc caccccaccg      180
ctgcgcgcag tgcccgcgag ccttccgaag cggcgccggg ctgcggagtc acgcgcgcat     240
ccacgtgtcc cggagcccca cgcgacccg tgtctcagac gcccaccagt gtggcgtgtg      300
cggcaagtgc tttggcaaga gctctacgct gacgcgacac ctgcaacgca ctcgggggan    360
aaaccctnna gnngcccgan tgnggnaagg gcttctggag agcccacgct ggtgcgccac    420
cagcgcacac acacnggcga aaagccgtac gcatgtggcg actgtggacg ctgttnagcg    480
agagttccac gcttnttgcg ccatcggcgc anccataaag ggcgagcggn cacatgcgtg     540
cgccacttgc ggnaagggtt tcgggcagcg ctccacctgg tggtgcacca gcgcattcac     600
acnggcgaag aagcctttgc gtgccccgna gtggcgggcg g                        641
```

<210> SEQ ID NO 57
<211> LENGTH: 428
<212> TYPE: DNA
<213> ORGANISM: Homo sapiens
<220> FEATURE:
<221> NAME/KEY: misc_feature
<222> LOCATION: (1)...(428)
<223> OTHER INFORMATION: n = A,T,C or G

<400> SEQUENCE: 57

```
cggccgcgcc gttccggctc ccgagccccg cctgcgcgcg gcctcctcgg cgcagccatc      60
ctcttggctg ccgcgggcgg caaagcccac ggcatctgcc atttgtcatt cagcccgtcg     120
gtaccgcccc gagccttgat ttagacacgg ctggggcgtg ctctggcctc actctccggg     180
cgggtgctgg acggacggac ggacggggca gccgtgctca cagctcanca gcgcgggggcc    240 ttggcgcgcg gggcgctttc ccgggtcgcc gtcatggccg cggaggtgga cgcccgagcg     300
gnctcgcctg agctccgggg gtcgtcgccc cgcaaggtag nttttgggtg ctcccgcttc     360
ggcgggccgg cttgggggca acggtggccn ggcattgccc gctgcgaaga cngccttggt     420
tccggccg                                                              428

<210> SEQ ID NO 58
<211> LENGTH: 362
<212> TYPE: DNA
<213> ORGANISM: Homo sapiens
<220> FEATURE:
<221> NAME/KEY: misc_feature
<222> LOCATION: (1)...(362)
<223> OTHER INFORMATION: n = A,T,C or G

<400> SEQUENCE: 58
cggccgccaa gaaggccgcg cccgcgaaga agggcgtcag ccgcgtcgtt ggcagcaaga      60
caccggccac caagaccatc aaggncggcg cggccaagcc ggtggcgaag aaggcggctc     120
cggccaagaa ggctgctccg gccaanaagg cggcgcccgc caagaaggtc gtcgccacga     180 aagcccggc caagaaggct gcagccaaga agggctgatg cgtctccttc tagtcgccgt      240
gggccagcgc cagccggcct gggccgacac ggcctatgaa gacttcgcca gcgctttcc     300 gcccgagctg aggctggagc tgaaggccgt caaggccgag acacgcggca gcaagacggc     360
cg                                                                    362

<210> SEQ ID NO 59
<211> LENGTH: 691
<212> TYPE: DNA
<213> ORGANISM: Homo sapiens
<220> FEATURE:
<221> NAME/KEY: misc_feature
<222> LOCATION: (1)...(691)
<223> OTHER INFORMATION: n = A,T,C or G

<400> SEQUENCE: 59
cggccgctta gtcgcagggc ccgccacccg agggtcgcgc agcccactgg gcccgatgga      60
gccgccgcgt gccgggcgcg tgcgcnanct cnccccgggcg ggggccgngg ggcgctaacg     120
gtcgcaaaca anttcgccgc cctgggccgg gaggcggctc aacaccntga ctgccnacct    180
acgagacccg tttacctcan tgcggngtgt gctggcggna ncccgcgccg ctnnaagcaa     240
taaccgngcc gccaccgctg ctgccgcggc cctgagggag ccggcccctg ccctcccgcg     300
ccccgagtcc ccactgcnct ccgnatgtca anggngcccg ccccggtncc gcccatnca      360 cgttgagacg cnaacaaaac ccanacggcc aggtncaagc ttnccaagct ttatttattg    420
gcaaatttgg gcggcccnnc cgcacggcan ccttcgagnc anccgccnag tgtgcaccaa    480
tcccgcgatg gngntttaat cgtgtttttt cttttctgga tgatataaat attgaccgna    540
cacttcntgn ttgntccagg gnttttntt ggggcccca aaagccgcat ttggcctttg     600
ggggaanagg ngaaggttcc tgccntnccg nccnanatta naaaaaatng ggantccccc    660
gggccngcag gaattttttnt tncaaactta n                                    691
```

```
<210> SEQ ID NO 60
<211> LENGTH: 120
<212> TYPE: DNA
<213> ORGANISM: Homo sapiens
<220> FEATURE:
<221> NAME/KEY: misc_feature
<222> LOCATION: (1)...(120)
<223> OTHER INFORMATION: n = A,T,C or G

<400> SEQUENCE: 60
cggccgtgag gatgttggtg cccacgtgcg ctgtcctccg ncagtgcggc aggatggtgg      60
tgatcaacgt gcccaccatg cccaggaagc tgagcaggaa gcccanaagc tgcacggccg     120

<210> SEQ ID NO 61
<211> LENGTH: 229
<212> TYPE: DNA
<213> ORGANISM: Homo sapiens

<400> SEQUENCE: 61
cggccgtcag ccatcgtaat gacatgtctg tgggttgccc tgtgccgcca ggctgggctg      60
tcggaagcac ccagcgacgt gtctgtgggt ccgccccgtg ccgccaggcc gggccatcgg     120
aaacacctgc agtaaccgga gtgccctcgc tgatagccct tgttccgggg cctcgtcctg     180
ggctgtgcag agctccagcc ctagcccag ccccagctgc aggcggccg                 229

<210> SEQ ID NO 62
<211> LENGTH: 400
<212> TYPE: DNA
<213> ORGANISM: Homo sapiens
<220> FEATURE:
<221> NAME/KEY: misc_feature
<222> LOCATION: (1)...(400)
<223> OTHER INFORMATION: n = A,T,C or G

<400> SEQUENCE: 62
tggactcacc gcggtggcng ctgacgccag cgtcacgggc tccgaggggc cagcccgccc      60
gaggccaggt agccgctgac gggcacctgc ttggccagga gctgggaggt gggcgtgttg     120
agcgccatga cgggctggcc caccacctgg atgggcgcca ggcccagcgt ggccgccgtg     180
gcacccccag ggctgccatt gggcaggcct tggaggcccg ggatgggctg cagtgtcaca     240
ttgcccaggc ccacaggctg caggaagggc tgcacactca gggccttgtt gaccacgtcc     300
tggggcggca ccagggcctg gtgggtcagc acggtgggcg ggccctgcag ccccagcagg     360
tcggtgctgc tgggaagagg gcttggggcc ccgcagccac                          400

<210> SEQ ID NO 63
<211> LENGTH: 123
<212> TYPE: DNA
<213> ORGANISM: Homo sapiens

<400> SEQUENCE: 63
ccgcggtggc ggccgccccg tctgggaggt ggggagtgcc tctgcccagc cgccacaccg      60
tctgggaggt gaggagcgcc tctacctggc agcccatct gggaactgag gagcgcctct     120
gca                                                                   123

<210> SEQ ID NO 64
<211> LENGTH: 110
<212> TYPE: DNA
<213> ORGANISM: Homo sapiens

<400> SEQUENCE: 64
cggccgggca gaggcgccca cttcccagac ggggcggcca ggcagaggcg ctccccacct      60
```

```
cccagatgaa gggcggctgg gcagaggtgc tcccacctc ccaggcgggg            110

<210> SEQ ID NO 65
<211> LENGTH: 332
<212> TYPE: DNA
<213> ORGANISM: Homo sapiens

<400> SEQUENCE: 65
cggccgagat gcactcagat ttatgttgtg aatttgttat gttcaggtaa tttgatggtg    60
tattcttatg caatgagatc tggatgtcat ttctggttct gctaattaga acatctgtga   120
ccttgatcaa gcaagaactt tctctcttgt ggacctcaca tcctacaatt gtatattgtc   180
ctgcatgtcc ctcagacact tttcgttttt cttcagtctt ttttcttttt gtcctttaga   240
ttggataatt tctgatcttc tgagaatttt tttattatct gcaacttgct gggttttttct   300 tagaatttca gtttattttt tgtattttttt ta                                332

<210> SEQ ID NO 66
<211> LENGTH: 204
<212> TYPE: DNA
<213> ORGANISM: Homo sapiens

<400> SEQUENCE: 66
aggggtgcct ctgcgccta aagaaaccgg gggagcccca caaccctcc cccaccagga      60 cactaaaagg caagctttcg gtacagtgag acatcaaagc tcctaggcc ctgagtcaaa    120 ggtatagccg tgtaatatcc cagtgccagc tctccggctg cggggagcct ggcgcaaagc   180
ttccaagcct tccttgttca aaaa                                          204

<210> SEQ ID NO 67
<211> LENGTH: 678
<212> TYPE: DNA
<213> ORGANISM: Homo sapiens
<220> FEATURE:
<221> NAME/KEY: misc_feature
<222> LOCATION: (1)...(678)
<223> OTHER INFORMATION: n = A,T,C or G

<400> SEQUENCE: 67
tggactcccc gcggtggatg ccgccggggc agccgaggcg aggactgcgg ggagctgacg    60
ggtgagtagg gcanggacgg gcagatgcag cgtncgttca tgtccaggct gccaccggct   120
gccagcccac cctgggaccg ctcttgcaga gacagcttgc gaccggagag gtggggccgg   180
gcctgggacc cggaggagtc aaggggggacc tcttggccat cggcctccag gggccggcca   240
cctgcagttt tggggcccag ctggaggtca gcagggtgga ctcacaaccc ctgagttca    300 ggtacaggga gctgtggaga caggcccacc caggctgacc ttccccanag ccttgctgtc   360
acggagagga gggggcgttg gaggaaanggc cacaaatgcn ngagaggggg caatggcctg   420
ngacaagatg gagaacagcc acccgttccc cagtacagcc aggtcangac acggatccca   480
ncaagccctt tggatgggga gactgaggta cagctgatga ctcacccctat gtgataccag   540 ctgtgagagc cggagtgggg atgcanacac ggaggtggcc agtggncacc tncnaagact   600
caacatccan ggcgatgacg ccaaacagtc aaggcgtnag aaccccccnan annaagagtg   660 agtgncattc acctaata                                                 678

<210> SEQ ID NO 68
<211> LENGTH: 113
<212> TYPE: DNA
<213> ORGANISM: Homo sapiens
```

```
<400> SEQUENCE: 68
cggccgggcg gaggggctcc tcacttctca gacagggcat tcggtcagag atgctcctca        60
caccccagac ggggcggtgg ggcagaggcg ctccccacat cccagacgat ggg              113

<210> SEQ ID NO 69
<211> LENGTH: 179
<212> TYPE: DNA
<213> ORGANISM: Homo sapiens
<220> FEATURE:
<221> NAME/KEY: misc_feature
<222> LOCATION: (1)...(179)
<223> OTHER INFORMATION: n = A,T,C or G

<400> SEQUENCE: 69
cggccgcgga cccccgacct cgacccaaac tgcatgcggc tgaggacccc caagccaggc        60
agacgccaat ccagacccca cgnnnnnnnn nnaagacgg ttttttttgcc cttttgacgt      120 ttgggagtcc cacgttcttt taatagtggg acctctttgg ttncaaaaan nggnaanat      179

<210> SEQ ID NO 70
<211> LENGTH: 835
<212> TYPE: DNA
<213> ORGANISM: Homo sapiens
<220> FEATURE:
<221> NAME/KEY: misc_feature
<222> LOCATION: (1)...(835)
<223> OTHER INFORMATION: n = A,T,C or G

<400> SEQUENCE: 70
cggccggtgc caaaggtcct gtgtgcccag aagaagtgaa tggtttnggc caggtcaggc        60
agaaggacct ggttgtggca gcgctgacaa gagagcaccc cagatccatc ccttacaaaa       120
tgatcgaggg gcttcttcca gagggcaccg tctggttccc tgaggggagt gcagcagccc       180
tgacatagcc ttcaggagcc gtggcagagc tgcagagggg accccagcag tggggccctg       240
acaaggacga ggtgcaccac catggggctt cccactgaac tctcggcgcc aggacgagcc       300
aagggacggg ggcggcgccc anccanact caagctcagg tcccttgggt ccccgcgggg       360
gacaccttcg acagcaggtt cctggggcca ccttctgccc cacaccatga ganaaaacat       420
tgcaggacga attnctnctt tgccccgcag cccacgccgc ctntttccaa ggtaggccct       480
nggccctggc cccattgaac gaacgggcaa gccnattaag ggcnggnntt tntgggaann       540
cctggggggg ccaancccct ttttggnttt ctttgggggcc tggaaacctt cnaacaatng       600
ggnccccctn ggggggggcct ttttttnaaag ggaacccttt tcgggggggn gggtttggtc       660
ttnggggggg gncccctggg ggggngggg gggaatcaac ttggcaaaaa cttcggggna       720
aaccctnggg gcttttttng ggcccggttt ttaaaaacta agtggggaat cccccnggg       780 cttggaggga attcnatatt caagncttat tgantacccg gtcgancttg gnggg            835

<210> SEQ ID NO 71
<211> LENGTH: 757
<212> TYPE: DNA
<213> ORGANISM: Homo sapiens
<220> FEATURE:
<221> NAME/KEY: misc_feature
<222> LOCATION: (1)...(757)
<223> OTHER INFORMATION: n = A,T,C or G

<400> SEQUENCE: 71
caaaactgga gctccaccgc ggtggcggcc cgtcacgcac tccacattct gcagctcccg        60
cagccgcagg ctccggatgg ctgccgcgta gatgtccttg ttctcccacc tgcccgggtg       120
```

```
aggagcacag gtgagggaga acaccgccga agaggctggg tctggggggcc acacccactc    180 agctggaggt cccggatcct ctcttgggag aggcctgggg cccagccgcc ctggtcatcc    240
cagtcctttc ctgcctctgg tgccgccgcc tcagagctgc tgttttctta gtaaacccct    300
tctgctgagg accctctttc ttggcaccca ccatcctgcc tcatctccct ctcctggtga    360
aatccacctg tcacctgacc taggtcctcg tgtcattgcc caggaacaga tgctgctgtc    420
ataccctggc tggctggccg ggccagcccc tgccagcccc tgacacgcgc acacactcac    480
gccacaagga tgtgccggcc ccggctgaca gctccacctt ctcgcccgtc atggtcaggt    540
aggtgaacct gcagcagggc ttgttggggc tgtcaagggc tcttccgtgg ccaggtgctg    600
ggangcgaat cttancgcac aagggggcctn caagcttcgg gtcttaatna tttgaatctg    660
ggaaggggtg gganggcaag aaaccnaggg ctttatttat gaagggccat ngggaaggng    720
ggaacccttg atccccccaag gtnggggtng ggtaaat                            757
```

<210> SEQ ID NO 72
<211> LENGTH: 558
<212> TYPE: DNA
<213> ORGANISM: Homo sapiens
<400> SEQUENCE: 72

```
cggccgcctt gacccaggct acccttagcc aatatcctct gccctgggt ggctggtggc      60 tgggcctcag ggtgggcaac gttaggggtt tggcgaaagc ccgcccatg ggattgaggg     120 acggggctgc actccaaccg tctgcacctg ctcttccccc acccctgtgg gacctcatct    180
tcacgtgcca tgtgtgctga aggcccaggg cccagcaggg ggcagtggca cctgttgacg    240
gaaaaggccg aggtgcttac cagtggacct tctggcccgc cctcccctg tcacttgtcg     300 ggcatccagg gccccgacct gtgcctagcc gccagggtga cagaaggcag aactgaagcg    360
gggtctgggc cacgggccag gccactgcct tttgtcctca gtgaccatac attcctgctc    420
tcggacttga actctactgt aactgttttc ttgaaatgaa gctgtacagg acgattcact    480
gccatgccag tcaggcgggc ttgccatgtt ctgtgaatct cgagtgagcg gtgccacccg    540
cccccatacc tccgccac                                                  558
```

<210> SEQ ID NO 73
<211> LENGTH: 927
<212> TYPE: DNA
<213> ORGANISM: Homo sapiens
<220> FEATURE:
<221> NAME/KEY: misc_feature
<222> LOCATION: (1)...(927)
<223> OTHER INFORMATION: n = A,T,C or G
<400> SEQUENCE: 73

```
aaanctggnc tccccgcggt ggctgcccgg gcagaggcgc tcctcacttc ccagatgggg     60
tggctgggca gaggcgctcc tcacatctca gacaatgggc ggtcangcag agatgctcct    120
cacttcctat acaggatggc ggccaggcag aggcgctcct cacttcccat tcagggcaag    180
ccgggcagag gcgctcctca cttnctccca natgggcgg cccgctctta taactantgg    240 atccccccggg cttggaggaa attcnatatc aagctnatcg ataccgtcgg acctnaaggg    300
gggggccccg gntaccccaa attcgcccct ataggngagt tcggaattta cgccgccgct    360
taaacttggg cccgnanatn ttttttacca aacggttctt tgnaacctng gggnaaaaaa    420
acccncttgg ggcgggttta acccccccaaa ccttttnaaa ttccccccncc tttgggcaag    480 gcnaaanaat ttccccccccc nttttttttgg ncccaagccc ttggggccgg ttnaaattaa    540
```

| | |
|---|---|
| acccn aaaa aaaaagggcc ccccgccaa cccttnntt ccggccccn ttttccccna | 600 |
| aaacaagant tggccggcca aagcccntgg naaattgggg cgaaaantgg gggaaccncc | 660 |
| ccccccttg ttaagccggg gccgncaatt tnaaanccgc cnggncgggg ttggttggnt | 720 |
| gggttttacc nccgccaanc cgtngaaccc gcttaccaac ctttggncca gcggcccct | 780 |
| taaccggccc ccngnttcct tttccgcntt ttcctttncc cttttccttt tcttnggncc | 840 |
| ncnntttccg cccggctttt ttnccccctt cnaaggcttc ttaaaatcgg ggggcttnc | 900 |
| ccttttaagg ggtttnccga atttaan | 927 |

```
<210> SEQ ID NO 74
<211> LENGTH: 415
<212> TYPE: DNA
<213> ORGANISM: Homo sapiens
<220> FEATURE:
<221> NAME/KEY: misc_feature
<222> LOCATION: (1)...(415)
<223> OTHER INFORMATION: n = A,T,C or G

<400> SEQUENCE: 74
```

| | |
|---|---|
| tggactccac cgcggtggcg gcccgcccat cgtctgagat gtggggagtg cctttgcccc | 60 |
| gccgccccgt ctgggatgtg aggagcgcct ntgcccagtc gcgacccgt ctgggaggtg | 120 |
| aggagcgtcn ctgccance gccccatctg agaaaggagg agaccctccg cctggcaacc | 180 |
| gccccgtctg agaagtgagg agaccctccg cccggcagtc gccccgtctg agaagtgagg | 240 |
| agcccctccg cccagcagcc accccgtctg ggaagtgagg agcgtctccg nccggcagcc | 300 |
| gccccgtccg gganggaggt gggggtcagc ccccgccagg ccagccgccc cgtctgggag | 360 |
| ggaggtgggg gggtcaancc ccttaccggc cngtcntttc gttntgtngg ttagg | 415 |

```
<210> SEQ ID NO 75
<211> LENGTH: 683
<212> TYPE: DNA
<213> ORGANISM: Homo sapiens
<220> FEATURE:
<221> NAME/KEY: misc_feature
<222> LOCATION: (1)...(683)
<223> OTHER INFORMATION: n = A,T,C or G

<400> SEQUENCE: 75
```

| | |
|---|---|
| tgggctccac cgcggtggcn gccgtggctc tgtggagctc tccgtcccag ggaaccttct | 60 |
| cctggctttc gtgtcctgcc ccttcccaga tttccccacc cctctggctg tgccttctgt | 120 |
| gccttccccg ccagccctga tgtgggcacg gntcacgccc aacacttctt aagcgcttcc | 180 |
| ttccttccca attccgccca tgatttcccc cacgcctgct ccgtttctga gtgcaggcca | 240 |
| ctcccaggtt gacacctgcg ttccatgttg cacggctcag catgtgggct tggacagtgg | 300 |
| gagatgcggc tttccatgaa cagccccagt gtgtggtccg gcgagtggcg aggcagctct | 360 |
| gtggtggcca ggaccaaacc cagggtcttg ctgttctacc accctccacc cagatctgaa | 420 |
| gctcagagct aaaagtgaca ttgtgccttc tggccagtgg gaaggagtta ggagagaaga | 480 |
| gggagggacc tgcttcgcgt tgagggcatg ggcaggaagc acaggcttca ctcccctcc | 540 |
| acaagccagg cgtgcgggtg acgtggcgac ctgtggggtg acgtgggcga cctgtgggtg | 600 |
| acgttggcgn cattgcgggt gaacgtgacn accttgtggg tgatgtggtg gcnttccggn | 660 |
| tgacattggc naccttcaag gtg | 683 |

```
<210> SEQ ID NO 76
<211> LENGTH: 464
```

```
<212> TYPE: DNA
<213> ORGANISM: Homo sapiens

<400> SEQUENCE: 76
cagtaaagat tcaatcaaat aaggagatat ctgagagaga cagagagaga gagagagaga      60
gagagaaaca ataataaatg tctccaaata agaagtcatt tatctaaact gtttgaacat     120
caaatagcag ggcttttttt ttttcctttt atctcacaag accactgtct gctacctaaa     180
atttagaagg aataaaaact ctgaacttag attgaggctt cccaaaccac agagccaaac     240
ctcaacttca gaaattcctg gcaaactatg tattagctag tacatgataa aatgaaacct     300
ccatccttgt taattcctta cgtgcagagc tgttcatatt aaataatgtc tcttttgttt     360
ttactcatgc tttgttttta cttatactta cgcatttctg aacaaacgat agcaaagcaa     420
aaaaaacaaa aacaaaaaaa aaacctttat tcagttcatc ctaa                      464

<210> SEQ ID NO 77
<211> LENGTH: 129
<212> TYPE: DNA
<213> ORGANISM: Homo sapiens
<220> FEATURE:
<221> NAME/KEY: misc_feature
<222> LOCATION: (1)...(129)
<223> OTHER INFORMATION: n = A,T,C or G

<400> SEQUENCE: 77
tggactcccc gcggtggcgg ccgggcagag gcgctcgtna nttcccagac ggggcggcca      60 gnaangggg ctcctnacat cccanacgat gggcagncag gcagagacac tnctcacttn     120
ctatacagg                                                             129
```